US007790959B2

(12) United States Patent
Kishore et al.

(10) Patent No.: US 7,790,959 B2
(45) Date of Patent: *Sep. 7, 2010

(54) ALTERED LINOLENIC AND LINOLEIC ACID CONTENT IN PLANTS

(75) Inventors: Ganesh Murthy Kishore, Chesterfield, MO (US); Thomas Gene Ruff, Pacific, MO (US); Vincent Jean-Marie Armel Arondel, Paris (FR); Susan Irma Gibson, Houston, TX (US); Christopher Roland Somerville, Palo Alto, CA (US)

(73) Assignee: Monsanto Technology LLC, St. Louis, MO (US)

( * ) Notice: Subject to any disclaimer, the term of this patent is extended or adjusted under 35 U.S.C. 154(b) by 604 days.

This patent is subject to a terminal disclaimer.

(21) Appl. No.: 11/705,382

(22) Filed: Feb. 12, 2007

(65) Prior Publication Data

US 2008/0201802 A1    Aug. 21, 2008

Related U.S. Application Data

(60) Division of application No. 08/432,147, filed as application No. PCT/US94/01321 on Feb. 4, 1994, now Pat. No. 7,205,457, which is a continuation-in-part of application No. 08/156,551, filed on Nov. 22, 1993, now abandoned, which is a continuation of application No. 08/014,431, filed on Feb. 5, 1993, now abandoned.

(51) Int. Cl.
*A01H 5/00* (2006.01)
*C12N 15/82* (2006.01)
*C07H 21/04* (2006.01)

(52) U.S. Cl. ............... 800/298; 800/281; 536/23.2

(58) Field of Classification Search ............... None
See application file for complete search history.

(56) References Cited

U.S. PATENT DOCUMENTS 5,057,419 A    10/1991   Martin et al. ............... 435/255
7,205,457 B1 *  4/2007   Kishore et al. ............. 800/298

FOREIGN PATENT DOCUMENTS

| EP | 0 120 516 B1 | 10/1991 |
| NL | A-9 002 130 | 4/1992 |
| WO | WO 91/13972 | 9/1991 |
| WO | WO 93/06712 | 4/1993 |
| WO | WO 93/11245 | 6/1993 |

OTHER PUBLICATIONS

Ammirato, P.V., et al., (1984) *Handbook of Plant Cell Culture—Crop Species*, Macmillan Publ. Co.
Arondel, et al., (1992) "Map-Based Cloning of a Gene Controlling Omega-3 Fatty Acid Desaturation in Arabidopsis," *Science*, 258:1353-1355 (1992).
Barlett, S.G., et al., (1982) In Methods in Chloroplast Molecular Biology, Elsevier Biomedical press, New York, pp. 1081-1091.
Beachy, R.N., Chem, Z.L., Horsch, R.B. Rogers, S.G., Hoffmann, N.J., and Fraley, R.T., (1985) *EMBO J*, 4:3047-3053.
Benfey, et al., (1989) "The CaMV 35S Enhancer Contains at Least Two Domains Which Can Confer Difference Developmental and Tissue-Specific Expression Patterns," *EMBO J.*, vol. 8 8:2195-2202.
Bevan, M., (1984) "Binary *Agrobacterium* Vectors for Plant Transformation," *Nucleic Acids Research*, 12:8711-8721, No. 22.
Bird, C.R., and Ray, J.A. (1991) *Biotech. Gen. Engin. Rev.*, 9:207-227.
Bray, E.A., Naito, S., Pan, N.S., Anderson, E., Dube, P., and Beachy, R.H. (1987) *Planta*, 172:364-370.
Browse, et al., (1985) "A Mutant of *Arabidopsis* Lacking a Chloroplast-Specific Lipid," *Science*, 227:763-765.
Browse, J., McCourt, P.J., Somerville, C.R. (1986) *Anal. Biochem.* 152:141-146.
Browse, J. McCourt, P., Somerville, C.R., (1986b) *Plant Physiol.*, 81:859-864.
Browse, et al., (1981) "Catalase Stimulates Linoleate Desaturase Activity in Microsomes From Developing Linseed Cotyledons," *FEBS Letters*, vol. 131:111-114.
Browse, J., McCourt, P.J., Somerville, C.R. (1991) *Ann. Rev. Plant Physiol. Mol. Biol.* 42:467-506.
Browse, J., et al., (1990) "Strategies for Modifying Plant Lipid Composition,"*Plant Gene Transfer*, pp. 301-309.
Chang, et al., (1988) "Restriction Fragment Length Polymorphism Linkage Map for *Arabidopsis thaliana*," *Proc. Natl. Acad. Sci. USA*, 85:6856-6860.
Christou, P., McCabe, D.E., Martinell, B.J., and Swain, W.F. (1990) *Trends Biotechnol.*, 8:145-151.
Church, et al., (1984) "Genomic Sequencing," *Proc. Natl. Acad. Sci. USA*, 81:1991-95.
Doyle, J.J., Schuler, M.A., Godette, W.D., Zenger, V., and Beachy, R.N. (1986),*J Biol. Chem.*, 261:9228-9238.
Farmer, E.E., and Ryan, C.A. (1992) *Plant Cell*, 4:129-134.
Fromm, M., UCLA Symposium on Molecular Strategies for Crop Improvement, Apr. 16-22, 1990. Keystone, CO.
Grill, E., and Somerville, C.R., (1991) *Molec. Gen. Genet.*, 226:484-490.
Harwood, J.L., (1988)) "Fatty Acid Metabolism," *Annu. Rev. Plant Physiol.*, 39:101-38.
Herrera-Estrella, et al., (1983) "Expression of Chimaeric Genes Transferred into Plant Cells Using a Ti-Plasmid-Derived Vector," *Nature*, 303:209-213.
Hinchee, et al., (1988) Production of Transgenic Soybean Plants Using *Agrobacterium*-Mediated DNA Transfer, *Bio/Technology*, 6:915-922.
Horsch, et al., (1986) "Rapid Assay of Foreign Gene Expression in Leaf Discs Transformed by *Agrobacterium tumefaciens*: Role of T-DNA Borders in the Transfer Process," *Proc. Natl. Acad. Sci. U.S.A.*
Hugly, et al., (1991) "Linkage Relationships of Mutations That Affect Fatty Acid Composition in *Arabidopsis*," *J. Hered.*, 82:484-488.

(Continued)

*Primary Examiner*—Elizabeth F McElwain
(74) *Attorney, Agent, or Firm*—Chunping Li; Howrey LLP

(57) ABSTRACT

Transformed plants which have increased or decreased linolenic acid content are disclosed. Also disclosed are plants which express a linoleic acid desaturase gene.

18 Claims, 25 Drawing Sheets

OTHER PUBLICATIONS

Hugly, S., and Somerville, C.R., (1992) *Plant Physiol.*, 99:197-202.

Iba, et al., (1993) "A Gene Encoding a Chloroplast Omega-3 Fatty Acid Desaturase Complements Alterations in Fatty Acid Desaturation and Chloroplast Copy No. of the *fad7* Mutant of *Arabidopsis thaliana*," *J. Biol. Chem.*, 32:24099-24105.

Katagiri, et al., (1989) "Two Tobacco DNA-Binding Proteins with Homology to the Nuclear Factor CREB," *Nature*, 340:727-30.

Kearns, E.V., Hugly, S., Somerville, C.R., (1991) Arch. Biochem. Biophys., 284:431-436.

Klee, et al.,(1985) "Vectors for Transformation of Higher Plants," *Bio/Technology*, 3:637-41.

Knutzon,et al., (1992) "Modification of *Brassica* Seed Oil by Antisense Expression of a Stearoyl-acyl Carrier Protein Desaturase Gene," *Proc. Natl. Acad. Sci. U.S.A.* 89:2624-28.

Lemieux, B.M., Miguel, C.R., Somerville, J. (1990) *Theor. Appl. Genet.*, 80:234-240.

Lipman, D.J., and Pearson, W.R., (1985) "Raid and Ssensitive Protein Similarity Searches," *Science*, 227:1435-1441.

McKeon, T.A., Stumpf, P.K., (1992) "Purification and Characterization of the Stearol-acyl Carrier Protein Desaturase and the Acyl-acyl Carrier Protein Thioesterase from Maturing Seeds of Safflower," *J. Biol. Chem.*, 257:12141-12147.

McCourt, P., Kunst, L., Browse, J., Somerville, C.R., (1987) *Plant Physiol.*, 84:353-361.

McSheffrey, et al., (1992) "Characterization of Transgenic Sulfonylurea-resistant Flax," *Theor. Appl. Genet.*, 84:480-86.

Meinke, D.W., Chen, J., and Beachy, R.N., (1991) *Planta*, 153:130-139.

Mersereau, et al., (1990) "Efficient Transformation of *Agrobacterium tumefaciens* by Electroporation," *Gene* 90:149-141.

Polashock, et al., (1992) "Expression of the Yeast Delta-9 Fatty Acid Desaturase in *Nicotiana tabacuml*," *Plant Physiol.*, 100:894-901.

Rogers, et al., (1987) "Improved Vectors for Plant Transformation: Expression Cassette Vectors and New Selectable Markers," Academic Press, 153:253-277.

Samac, et al., (1990) "Isolation and Characterization of the Genes Encoding Basic and Acidic Chitinase in *Arabidopsis thaiiana*," *Plant Physiol.*, 93:907-14.

Sambrook, et al. (1989) "Molecular Cloning: A Laboratory Manual," Cold Spring Harbor Press, Cold Spring Harbor, NY.

Shanklin, J., Somerville, C.R., (1991) *Proc. Natl, Acad. Sci. USA*, 88:2510-2514.

Schmidhauser, et al., (1985) "Regions of Broad-Host-Range Plasmid RK2 Involved in Replication and Stable Maintenance in Nine Species of Gram-Negative Bacteria," *J. Bacteriol,.* 164:446-455.

Schmidt, et al. (1990) "Involvement of Ferredoxin in Desaturation of Lipid-Bound Oleate in Chloroplasts," *Plant Physiol.*, 94:214-220.

Schmidt, et al., (1990) "Desaturation of Oleoyl Groups in Envelope Membranes From Spinach Chloroplasts," *Botany*, 87:9477-9480.

Sherman, et al., (1986) Laboratory Course Manual for "Methods in Yeast Genetics," Cold Spring Harbor Laboratory Press, Cold Spring Harbor, NY.

Shimamoto, et al., (1989) "Fertile Transgenic Rice Plants Regenerated From Transformed Protoplasts," *Nature*, 338:274-276.

Steponkus, et al., (1990) "The Influence of Cold Acclimation on the Lipid Composition and Cryobehaviour of the Plasma Membrane of Isolated Rye Protoplasts" Soc. Lond. B 326:571-583.

Sukumaran, et al., (1972) "An Excised Leaflet Test for Evaluating Potato Frost Tolerance," *Hort Science*, 7:467-68.

Vasil, et al., (1990) "Regeneration of Plants From Embryogenic Suspension Culture Protoplasts of Wheat," *Bio/Technology*, 8:429-434.

Vollrath, et al., (1987) "Resolution of DNA Molecules Greater Than 5 Megabases by Contour-Clamped Homogeneous Electric Fields," *Nucleic Acids Res.*, 15:7865-7876.

Wada, H., Gombos, Z., Murata, N., (1990) *Nature*, 347:200-203.

Ward, et al., "Isolation of Single-copy-sequence Clones from a Yeast Artificial Chromosome Library of Randomly-sheared *Arabidopsis thaliana* DNA" Plant Mol. Biol. 14:561-568 (1990).

Yadav, et al., "Cloning of Higher Plant ω-3 Fatty Acid Desaturases" Plant Physiol. 103:467-476 (1993).

Yadav, et al., *In Biochemistry and Molecular Biology of Membrane and Storage Lipids of Plants* (N. Murata et al., eds) American Society of Plant Physiologists (publisher) "Genetic Manipulation to Alter Fatty Acid Profiles of Oilseed Crops" pp. 60-66 (1993).

* cited by examiner

```
AATCCATCAA ACCTTTATTC ACCACATTTC ACTGAAAGGC CACACATCTA GAGAGAGAAA        60

CTTCGTCCAA ATCTCTCTCT CCAGCG ATG GTT GTT GCT ATG GAC CAG CGC AGC       113
                            Met Val Val Ala Met Asp Gln Arg Ser
                             1               5

AAT GTT AAC GGA GAT TCC GGT GCC CGG AAG GAA GAA GGG TTT GAT CCA        161
Asn Val Asn Gly Asp Ser Gly Ala Arg Lys Glu Glu Gly Phe Asp Pro
 10              15                  20                  25

AGC GCA CAA CCA CCG TTT AAG ATC GGA GAT ATA AGG GCG GCG ATT CCT        209
Ser Ala Gln Pro Pro Phe Lys Ile Gly Asp Ile Arg Ala Ala Ile Pro
                 30                  35                  40

AAG CAT TGC TGG GTG AAG AGT CCT TTG AGA TCT ATG AGC TAC GTC ACC        257
Lys His Cys Trp Val Lys Ser Pro Leu Arg Ser Met Ser Tyr Val Thr
                 45                  50                  55

AGA GAC ATT TTC GCC GTC GCG GCT CTG GCC ATG GCC GCC GTG TAT TTT        305
Arg Asp Ile Phe Ala Val Ala Ala Leu Ala Met Ala Ala Val Tyr Phe
                 60                  65                  70

GAT AGC TGG TTC CTC TGG CCA CTC TAC TGG GTT GCC CAA GGA ACC CTT        353
Asp Ser Trp Phe Leu Trp Pro Leu Tyr Trp Val Ala Gln Gly Thr Leu
         75                  80                  85

TTC TGG GCC ATC TTC GTT CTT GGC CAC GAC TGT GGA CAT GGG AGT TTC        401
Phe Trp Ala Ile Phe Val Leu Gly His Asp Cys Gly His Gly Ser Phe
 90              95                 100                 105

TCA GAC ATT CCT CTG CTG AAC AGT GTG GTT GGT CAC ATT CTT CAT TCA        449
Ser Asp Ile Pro Leu Leu Asn Ser Val Val Gly His Ile Leu His Ser
                110                 115                 120

TTC ATC CTC GTT CCT TAC CAT GGT TGG AGA ATA AGC CAT CGG ACA CAC        497
Phe Ile Leu Val Pro Tyr His Gly Trp Arg Ile Ser His Arg Thr His
                125                 130                 135

CAC CAG AAC CAT GGC CAT GTT GAA AAC GAC GAG TCT TGG GTT CCG TTG        545
His Gln Asn His Gly His Val Glu Asn Asp Glu Ser Trp Val Pro Leu
                140                 145                 150
```

FIG.3a

| | |
|---|---|
| CCA GAA AAG TTG TAC AAG AAC TTG CCC CAT AGT ACT CGG ATG CTC AGA<br>Pro Glu Lys Leu Tyr Lys Asn Leu Pro His Ser Thr Arg Met Leu Arg<br>    155                       160                      165 | 593 |
| TAC ACT GTC CCT CTG CCC ATG CTC GCT TAC CCG ATC TAT CTG TGG TAC<br>Tyr Thr Val Pro Leu Pro Met Leu Ala Tyr Pro Ile Tyr Leu Trp Tyr<br>170                    175                    180                    185 | 641 |
| AGA AGT CCT GGA AAA GAA GGG TCA CAT TTT AAC CCA TAC AGT AGT TTA<br>Arg Ser Pro Gly Lys Glu Gly Ser His Phe Asn Pro Tyr Ser Ser Leu<br>                   190                   195                    200 | 689 |
| TTT GCT CCA AGC GAG AGG AAG CTT ATT GCA ACT TCA ACT ACT TGC TGG<br>Phe Ala Pro Ser Glu Arg Lys Leu Ile Ala Thr Ser Thr Thr Cys Trp<br>             205                  210                    215 | 737 |
| TCC ATA ATG TTG GCC ACT CTT GTT TAT CTA TCG TTC CTC GTT GAT CCA<br>Ser Ile Met Leu Ala Thr Leu Val Tyr Leu Ser Phe Leu Val Asp Pro<br>          220                    225                  230 | 785 |
| GTC ACA GTT CTC AAA GTC TAT GGC GTT CCT TAC ATT ATC TTT GTG ATG<br>Val Thr Val Leu Lys Val Tyr Gly Val Pro Tyr Ile Ile Phe Val Met<br>         235                    240                  245 | 833 |
| TGG TTG GAC GCT GTC ACG TAC TTG CAT CAT CAT GGT CAC GAT GAG AAG<br>Trp Leu Asp Ala Val Thr Tyr Leu His His His Gly His Asp Glu Lys<br>250                    255                    260                    265 | 881 |
| TTG CCT TGG TAC AGA GGC AAG GAA TGG AGT TAT TTA CGT GGA GGA TTA<br>Leu Pro Trp Tyr Arg Gly Lys Glu Trp Ser Tyr Leu Arg Gly Gly Leu<br>             270                  275                    280 | 929 |
| ACA ACT ATT GAT AGA GAT TAC GGA ATC TTC AAC AAC ATC CAT CAC GAC<br>Thr Thr Ile Asp Arg Asp Tyr Gly Ile Phe Asn Asn Ile His His Asp<br>                  285                    290                    295 | 977 |
| ATT GGA ACT CAC GTG ATC CAT CAT CTT TTC CCA CAA ATC CCT CAC TAT<br>Ile Gly Thr His Val Ile His His Leu Phe Pro Gln Ile Pro His Tyr<br>         300                    305                  310 | 1025 |

FIG.3b

```
CAC TTG GTC GAT GCC ACG AGA GCA GCT AAA CAT GTG TTA GGA AGA TAC        1073
His Leu Val Asp Ala Thr Arg Ala Ala Lys His Val Leu Gly Arg Tyr
    315                 320                 325

TAC AGA GAG CCG AAG ACG TCA GGA GCA ATA CCG ATT CAC TTG GTG GAG        1121
Tyr Arg Glu Pro Lys Thr Ser Gly Ala Ile Pro Ile His Leu Val Glu
330                 335                 340                 345

AGT TTG GTC GCA AGT ATT AAA AAA GAT CAT TAC GTC AGT GAC ACT GGT        1169
Ser Leu Val Ala Ser Ile Lys Lys Asp His Tyr Val Ser Asp Thr Gly
                350                 355                 360

GAT ATT GTC TTC TAC GAG ACA GAT CCA GAT CTC TAC GTT TAT GCT TCT        1217
Asp Ile Val Phe Tyr Glu Thr Asp Pro Asp Leu Tyr Val Tyr Ala Ser
                    365                 370                 375

GAC AAA TCT AAA ATC AAT TAACTTTTCT TCCTAGCTCT ATTAGGAATA               1265
Asp Lys Ser Lys Ile Asn
                380

AACACTCCTT CTCTTTTACT TATTTGTTTC TGCTTTAAGT TTAAAATGTA CTCGTGAAAC      1325

CTTTTTTTTA TTAATGTATT TACGTTAC                                         1353
```

FIG.3c

Met Val Val Ala Met Asp Gln Arg Ser Asn Val Asn Gly Asp Ser Gly
1            5                  10                 15

Ala Arg Lys Glu Glu Gly Phe Asp Pro Ser Ala Gln Pro Pro Phe Lys
            20                  25                 30

Ile Gly Asp Ile Arg Ala Ala Ile Pro Lys His Cys Trp Val Lys Ser
            35                  40                 45

Pro Leu Arg Ser Met Ser Tyr Val Thr Arg Asp Ile Phe Ala Val Ala
50                  55                  60

Ala Leu Ala Met Ala Ala Val Tyr Phe Asp Ser Trp Phe Leu Trp Pro
65                  70                  75                 80

Leu Tyr Trp Val Ala Gln Gly Thr Leu Phe Trp Ala Ile Phe Val Leu
            85                  90                 95

Gly His Asp Cys Gly His Gly Ser Phe Ser Asp Ile Pro Leu Leu Asn
            100                 105                110

Ser Val Val Gly His Ile Leu His Ser Phe Ile Leu Val Pro Tyr His
            115                 120                125

Gly Trp Arg Ile Ser His Arg Thr His His Gln Asn His Gly His Val
            130                 135                140

Glu Asn Asp Glu Ser Trp Val Pro Leu Pro Glu Lys Leu Tyr Lys Asn
145                 150                 155                160

Leu Pro His Ser Thr Arg Met Leu Arg Tyr Thr Val Pro Leu Pro Met
                165                 170                175

Leu Ala Tyr Pro Ile Tyr Leu Trp Tyr Arg Ser Pro Gly Lys Glu Gly
                180                 185                190

Ser His Phe Asn Pro Tyr Ser Ser Leu Phe Ala Pro Ser Glu Arg Lys
        195                 200                 205

Leu Ile Ala Thr Ser Thr Thr Cys Trp Ser Ile Met Leu Ala Thr Leu
    210                 215                 220

Val Tyr Leu Ser Phe Leu Val Asp Pro Val Thr Val Leu Lys Val Tyr
225                 230                 235                240

Gly Val Pro Tyr Ile Ile Phe Val Met Trp Leu Asp Ala Val Thr Tyr
                245                 250                255

FIG.3d

```
Leu His His His Gly His Asp Glu Lys Leu Pro Trp Tyr Arg Gly Lys
            260             265             270

Glu Trp Ser Tyr Leu Arg Gly Gly Leu Thr Thr Ile Asp Arg Asp Tyr
        275             280             285

Gly Ile Phe Asn Asn Ile His His Asp Ile Gly Thr His Val Ile His
        290             295             300

His Leu Phe Pro Gln Ile Pro His Tyr His Leu Val Asp Ala Thr Arg
305             310             315             320

Ala Ala Lys His Val Leu Gly Arg Tyr Tyr Arg Glu Pro Lys Thr Ser
            325             330             335

Gly Ala Ile Pro Ile His Leu Val Glu Ser Leu Val Ala Ser Ile Lys
            340             345             350

Lys Asp His Tyr Val Ser Asp Thr Gly Asp Ile Val Phe Tyr Glu Thr
            355             360             365

Asp Pro Asp Leu Tyr Val Tyr Ala Ser Asp Lys Ser Lys Ile Asn
            370             375             380
```

FIG.3e

```
              10        20        30        40        50        60
BND3.AMI    RSNVNGDSGARKEEGFDPSAQPPFKIGDIRAAIPKHCWVKSPLRSMSYVTRDIFAVAALA
             .: ::  .:.:. :..  ..   :  ..  :.:.
DESA.AMI    MTATIPPLTPTVTPSNPDRPIADLKLQDIIKTLPKECFEKKASKAWASVLITLGAIAVGY
              10        20        30        40        50        60
              70        80        90       100       110       120
BND3.AMI    MAAVYFDSWFLWPLYWVAQGTLFWAIFVLGHDCGHGSFSDIPLLNSVVGHILHSFILVPY
             .. .:.  .X.   : :.   ::  . ::.:::::: ...  .:.::::    . :.
DESA.AMI    LGIIYL-PWYCLPITWIWTGTALTGAFVVGHDCGHRSFAKKRWVNDLVGHIAFAPLIYPF
              70        80        90       100       110
             130       140       150       160       170       180
BND3.AMI    HGWRISHRTHHQNHGHVENDESWVPLPEKLYKNLPHSTRMLRYTVPLPH-LAYPIYLWYR
             :.::. :   ::  . ...: :...  :.  ..  : .::. ... :. .:. :
DESA.AMI    HSWRLLHDHHHLHTNKIEVDNAWDFWSVEAFQASPAIVRLFYRAIRGPFWWTGSIFHW--
            120       130       140       150       160       170
             190       200       210       220       230       240
BND3.AMI    SPGKEGSHFNPYSSLFAPSERKLIATSTTCWSIMLATLVYLSFLVDP-V-TVLKVYGVPY
             .  :::    : :...... :..    ..........  .. :  : . V: .  :.
DESA.AMI    ---SLMHFK--LSNFAQRDRNKVKLSIAV-VFLFAAIAFPALIITTGVWGFVKFWLMPW
                  180       190       200       210       220       230
             250       260       270       280       290       300
BNDS.AMI    IIFVMWLDAVTYLHHHGHDEKLPWYRGKEWSYLRGGL-TTIDRDYGIFNNIH-HDIGTHV
             ... :.::: : :: ..  ..   ..   .. .   :. :::  ::  ... :::...:
DESA.AMI    LVYHFWMSTFTIVHHTIPEIRF---RPAADWSAAEAQLNGTVHCDYPRWVEVLCHDINVHI
                   240       250       260       270       280
             310       320       330       340       350       360
BND3.AMI    IHHLFPQIPHYHLVDATRAAKHVLGRYYREPKTSGAIPIHLVESLVASIKKDHYVSDTGD
             ::: .::.::. .:. :: .  :. 
DESA.AMI    PHHLSVAIPSYNLRLAHGSLKENWGPFLYERTFNWQLMQQISGQCHLYDPEHGYRTFGSL
            290       300       310       320       330       340

BND3.AMI    IVF

DESA.AMI    KKV
            350
```

FIG.4

| | |
|---|---|
| GGAAAACACA AGTTTCTCTC ACACACATTA TCTCTTTCTC TATTACCACC ACTCATTCAT | 60 |
| AACAGAAACC CACCAAAAAA TAAAAAGAGA GACTTTTCAC TCTGGGGAGA GAGCTCAAGT | 120 |

```
TCTA ATG GCG AAC TTG GTC TTA TCA GAA TGT GGT ATA CGA CCT CTC CCC        169
     Met Ala Asn Leu Val Leu Ser Glu Cys Gly Ile Arg Pro Leu Pro
     1           5                  10                 15

AGA ATC TAC ACA ACA CCC AGA TCC AAT TTC CTC TCC AAC AAC AAC AAA         217
Arg Ile Tyr Thr Thr Pro Arg Ser Asn Phe Leu Ser Asn Asn Asn Lys
                20              25                  30

TTC AGA CCA TCA CTT TCT TCT TCT TCT TAC AAA ACA TCA TCA TCT CCT         265
Phe Arg Pro Ser Leu Ser Ser Ser Ser Tyr Lys Thr Ser Ser Ser Pro
             35              40                  45

CTG TCT TTT GGT CTG AAT TCA CGA GAT GGG TTC ACG AGG AAT TGG GCG         313
Leu Ser Phe Gly Leu Asn Ser Arg Asp Gly Phe Thr Arg Asn Trp Ala
             50              55                  60

TTG AAT GTG AGC ACA CCA TTA ACG ACA CCA ATA TTT GAG GAG TCT CCA         361
Leu Asn Val Ser Thr Pro Leu Thr Thr Pro Ile Phe Glu Glu Ser Pro
        65              70                  75

TTG GAG GAA GAT AAT AAA CAG AGA TTC GAT CCA GGT GCG CCT CCT CCG         409
Leu Glu Glu Asp Asn Lys Gln Arg Phe Asp Pro Gly Ala Pro Pro Pro
    80              85                  90                  95

TTC AAT TTA GCT GAT ATT AGA GCA GCT ATA CCT AAG CAT TGT TGG GTT         457
Phe Asn Leu Ala Asp Ile Arg Ala Ala Ile Pro Lys His Cys Trp Val
                100             105                 110

AAG AAT CCA TGG AAG TCT TTG AGT TAT GTC GTC AGA GAC GTC GCT ATC         505
Lys Asn Pro Trp Lys Ser Leu Ser Tyr Val Val Arg Asp Val Ala Ile
             115             120                 125

GTC TTT GCA TTG GCT GCT GGA GCT GCT TAC CTC AAC AAT TGG ATT GTT         553
Val Phe Ala Leu Ala Ala Gly Ala Ala Tyr Leu Asn Asn Trp Ile Val
             130             135                 140
```

FIG.10a

```
TGG CCT CTC TAT TGG CTC GCT CAA GGA ACC ATG TTT TGG GCT CTC TTT          601
Trp Pro Leu Tyr Trp Leu Ala Gln Gly Thr Met Phe Trp Ala Leu Phe
        145                 150                 155

GTT CTT GGT CAT GAC TGT GGA CAT GGT AGT TTC TCA AAT GAT CCG AAG          649
Val Leu Gly His Asp Cys Gly His Gly Ser Phe Ser Asn Asp Pro Lys
160                 165                 170                 175

TTG AAC AGT GTG GTC GGT CAT CTT CTT CAT TCC TCA ATT CTG GTC CCA          697
Leu Asn Ser Val Val Gly His Leu Leu His Ser Ser Ile Leu Val Pro
                180                 185                 190

TAC CAT GGC TGG AGA ATT AGT CAC AGA ACT CAC CAC CAG AAC CAT GGA          745
Tyr His Gly Trp Arg Ile Ser His Arg Thr His His Gln Asn His Gly
                195                 200                 205

CAT GTT GAG AAT GAC GAA TCT TGG CAT CCT ATG TCT GAG AAA ATC TAC          793
His Val Glu Asn Asp Glu Ser Trp His Pro Met Ser Glu Lys Ile Tyr
        210                 215                 220

AAT ACT TTG GAC AAG CCG ACT AGA TTC TTT AGA TTT ACA CTG CCT CTC          841
Asn Thr Leu Asp Lys Pro Thr Arg Phe Phe Arg Phe Thr Leu Pro Leu
        225                 230                 235

GTG ATG CTT GCA TAC CCT TTC TAC TTG TGG GCT CGA AGT CCG GGG AAA          889
Val Met Leu Ala Tyr Pro Phe Tyr Leu Trp Ala Arg Ser Pro Gly Lys
240                 245                 250                 255

AAG GGT TCT CAT TAC CAT CCA GAC AGT GAC TTG TTC CTC CCT AAA GAG          937
Lys Gly Ser His Tyr His Pro Asp Ser Asp Leu Phe Leu Pro Lys Glu
                260                 265                 270

AGA AAG GAT GTC CTC ACT TCT ACT GCT TGT TGG ACT GCA ATG GCT GCT          985
Arg Lys Asp Val Leu Thr Ser Thr Ala Cys Trp Thr Ala Met Ala Ala
                275                 280                 285

CTG CTT GTT TGT CTC AAC TTC ACA ATC GGT CCA ATT CAA ATG CTC AAA         1033
Leu Leu Val Cys Leu Asn Phe Thr Ile Gly Pro Ile Gln Met Leu Lys
                290                 295                 300
```

FIG.10b

```
CTT TAT GGA ATT CCT TAC TGG ATA AAT GTA ATG TGG TTG GAC TTT GTG     1081
Leu Tyr Gly Ile Pro Tyr Trp Ile Asn Val Met Trp Leu Asp Phe Val
    305             310             315

ACT TAC CTG CAT CAC CAT GGT CAT GAA GAT AAG CTT CCT TGG TAC CGT     1129
Thr Tyr Leu His His His Gly His Glu Asp Lys Leu Pro Trp Tyr Arg
320             325             330             335

GGC AAG GAG TGG AGT TAC CTG AGA GGA GGA CTT ACA ACA TTG GAT CGT     1177
Gly Lys Glu Trp Ser Tyr Leu Arg Gly Gly Leu Thr Thr Leu Asp Arg
            340             345             350

GAC TAC GGA TTG ATC AAT AAC ATC CAT CAT GAT ATT GGA ACT CAT GTG     1225
Asp Tyr Gly Leu Ile Asn Asn Ile His His Asp Ile Gly Thr His Val
        355             360             365

ATA CAT CAT CTT TTC CCG CAG ATC CCA CAT TAT CAT CTA GTA GAA GCA     1273
Ile His His Leu Phe Pro Gln Ile Pro His Tyr His Leu Val Glu Ala
    370             375             380

ACA GAA GCA GCT AAA CCA GTA TTA GGG AAG TAT TAC AGG GAG CCT GAT     1321
Thr Glu Ala Ala Lys Pro Val Leu Gly Lys Tyr Tyr Arg Glu Pro Asp
385             390             395

AAG TCT GGA CCG TTG CCA TTA CAT TTA CTG GAA ATT CTA GCG AAA AGT     1369
Lys Ser Gly Pro Leu Pro Leu His Leu Leu Glu Ile Leu Ala Lys Ser
400             405             410             415

ATA AAA GAA GAT CAT TAC GTG AGC GAC GAA GGA GAA GTT GTA TAC TAT     1417
Ile Lys Glu Asp His Tyr Val Ser Asp Glu Gly Glu Val Val Tyr Tyr
            420             425             430

AAA GCA GAT CCA AAT CTC TAT GGA GAG GTC AAA GTA AGA GCA GAT TGAAATGAAG     1472
Lys Ala Asp Pro Asn Leu Tyr Gly Glu Val Lys Val Arg Ala Asp
        435             440             445

CAGGCTTGAG ATTGAAGTTT TTTCTATTTC AGACCAGCTG ATTTTTTGCT TACTGTATCA     1532

ATTTATTGTG TCACCCACCA GAGAGTTAGT ATCTCTGAAT ACGATCGATC AGATGGAAAC     1592

AACAAATTTG TTTGCGATAC TGAAGCTATA TATACCATAA AAAAAAAAAA AAA           1645
```

FIG.10c

```
Met Ala Asn Leu Val Leu Ser Glu Cys Gly Ile Arg Pro Leu Pro Arg
 1               5                  10                 15

Ile Tyr Thr Thr Pro Arg Ser Asn Phe Leu Ser Asn Asn Asn Lys Phe
             20                  25                  30

Arg Pro Ser Leu Ser Ser Ser Tyr Lys Thr Ser Ser Ser Pro Leu
         35                  40                  45

Ser Phe Gly Leu Asn Ser Arg Asp Gly Phe Thr Arg Asn Trp Ala Leu
         50                  55                  60

Asn Val Ser Thr Pro Leu Thr Thr Pro Ile Phe Glu Glu Ser Pro Leu
 65                  70                  75                  80

Glu Glu Asp Asn Lys Gln Arg Phe Asp Pro Gly Ala Pro Pro Pro Phe
                 85                  90                  95

Asn Leu Ala Asp Ile Arg Ala Ala Ile Pro Lys His Cys Trp Val Lys
            100                 105                 110

Asn Pro Trp Lys Ser Leu Ser Tyr Val Val Arg Asp Val Ala Ile Val
            115                 120                 125

Phe Ala Leu Ala Ala Gly Ala Ala Tyr Leu Asn Asn Trp Ile Val Trp
            130                 135                 140

Pro Leu Tyr Trp Leu Ala Gln Gly Thr Met Phe Trp Ala Leu Phe Val
145                 150                 155                 160

Leu Gly His Asp Cys Gly His Gly Ser Phe Ser Asn Asp Pro Lys Leu
                165                 170                 175

Asn Ser Val Val Gly His Leu Leu His Ser Ser Ile Leu Val Pro Tyr
                180                 185                 190

His Gly Trp Arg Ile Ser His Arg Thr His His Gln Asn His Gly His
            195                 200                 205

Val Glu Asn Asp Glu Ser Trp His Pro Met Ser Glu Lys Ile Tyr Asn
            210                 215                 220
```

FIG.11a

```
Thr Leu Asp Lys Pro Thr Arg Phe Phe Arg Phe Thr Leu Pro Leu Val
225                 230                 235                 240

Met Leu Ala Tyr Pro Phe Tyr Leu Trp Ala Arg Ser Pro Gly Lys Lys
            245                 250                 255

Gly Ser His Tyr His Pro Asp Ser Asp Leu Phe Leu Pro Lys Glu Arg
            260                 265                 270

Lys Asp Val Leu Thr Ser Thr Ala Cys Trp Thr Ala Met Ala Ala Leu
            275                 280                 285

Leu Val Cys Leu Asn Phe Thr Ile Gly Pro Ile Gln Met Leu Lys Leu
            290                 295                 300

Tyr Gly Ile Pro Tyr Trp Ile Asn Val Met Trp Leu Asp Phe Val Thr
305                 310                 315                 320

Tyr Leu His His His Gly His Glu Asp Lys Leu Pro Trp Tyr Arg Gly
            325                 330                 335

Lys Glu Trp Ser Tyr Leu Arg Gly Gly Leu Thr Thr Leu Asp Arg Asp
            340                 345                 350

Tyr Gly Leu Ile Asn Asn Ile His His Asp Ile Gly Thr His Val Ile
            355                 360                 365

His His Leu Phe Pro Gln Ile Pro His Tyr His Leu Val Glu Ala Thr
            370                 375                 380

Glu Ala Ala Lys Pro Val Leu Gly Lys Tyr Tyr Arg Glu Pro Asp Lys
385                 390                 395                 400

Ser Gly Pro Leu Pro Leu His Leu Leu Glu Ile Leu Ala Lys Ser Ile
            405                 410                 415

Lys Glu Asp His Tyr Val Ser Asp Glu Gly Glu Val Val Tyr Tyr Lys
            420                 425                 430

Ala Asp Pro Asn Leu Tyr Gly Glu Val Lys Val Arg Ala Asp
            435                 440                 445
```

FIG.11b

```
AGAGAGTGCA AATAGAACGA CAGAGACTTT TTCCTCTTTT CTTCTTGGGA AGAGGCTCCA     60

ATG GCG AGC TCG GTT TTA TCA GAA TGT GGT TTT AGA CCT CTC CCC AGA      108
Met Ala Ser Ser Val Leu Ser Glu Cys Gly Phe Arg Pro Leu Pro Arg
 1           5                  10                 15

TTC TAC CCT AAA CAC ACA ACC TCT TTT GCC TCT AAC CCT AAA CCC ACT      156
Phe Tyr Pro Lys His Thr Thr Ser Phe Ala Ser Asn Pro Lys Pro Thr
             20                  25                 30

TTC AAA TTC AAT CCA CCA CTT AAA CCT CCT TCT TCT CTT CTC AAT TCC      204
Phe Lys Phe Asn Pro Pro Leu Lys Pro Pro Ser Ser Leu Leu Asn Ser
             35                  40                 45

CGA TAT GGA TTC TAC TCT AAA ACC AGG AAC TGG GCA TTG AAT GTG GCA      252
Arg Tyr Gly Phe Tyr Ser Lys Thr Arg Asn Trp Ala Leu Asn Val Ala
 50                  55                  60

ACA CCT TTA ACA ACT CTT CAG TCT CCA TCC GAG GAA GAC ACG GAG AGA      300
Thr Pro Leu Thr Thr Leu Gln Ser Pro Ser Glu Glu Asp Thr Glu Arg
 65                  70                  75                 80

TTC GAC CCA GGT GCG CCT CCT CCC TTC AAT TTG GCG GAT ATA AGA GCA      348
Phe Asp Pro Gly Ala Pro Pro Pro Phe Asn Leu Ala Asp Ile Arg Ala
             85                  90                 95

GCC ATA CCT AAG CAT TGT TGG GTT AAG AAT CCA TGG ATG TCT ATG AGT      396
Ala Ile Pro Lys His Cys Trp Val Lys Asn Pro Trp Met Ser Met Ser
             100                 105                110

TAT GTT GTC AGA GAT GTT GCT ATC GTC TTT GGA TTG GCT GCT GTT GCT      444
Tyr Val Val Arg Asp Val Ala Ile Val Phe Gly Leu Ala Ala Val Ala
             115                 120                125

GCT TAC TTC AAC AAT TGG CTT CTC TGG CCT CTC TAC TGG TTC GCT CAA      492
Ala Tyr Phe Asn Asn Trp Leu Leu Trp Pro Leu Tyr Trp Phe Ala Gln
             130                 135                140

GGA ACC ATG TTC TGG GCT CTC TTT GTC CTT GGC CAT GAC TGC GGA CAT      540
Gly Thr Met Phe Trp Ala Leu Phe Val Leu Gly His Asp Cys Gly His
145                 150                 155                160
```

FIG.12a

```
GGT AGC TTC TCG AAT GAT CCG AGG CTG AAC AGT GTG GCT GGT CAT CTT     588
Gly Ser Phe Ser Asn Asp Pro Arg Leu Asn Ser Val Ala Gly His Leu
                165             170             175

CTT CAT TCC TCA ATT CTG GTC CCT TAC CAT GGC TGG AGG ATT AGC CAC     636
Leu His Ser Ser Ile Leu Val Pro Tyr His Gly Trp Arg Ile Ser His
                180             185             190

AGA ACT CAC CAC CAG AAC CAT GGT CAT GTC GAG AAT GAC GAA TCA TGG     684
Arg Thr His His Gln Asn His Gly His Val Glu Asn Asp Glu Ser Trp
            195             200             205

CAT CCT TTG CCT GAA AGC ATC TAC AAG AAT TTG GAA AAG ACG ACT CAA     732
His Pro Leu Pro Glu Ser Ile Tyr Lys Asn Leu Glu Lys Thr Thr Gln
            210             215             220

ATG TTT AGG TTT ACA CTG CCT TTT CCA ATG CTC GCA TAC CCT TTC TAC     780
Met Phe Arg Phe Thr Leu Pro Phe Pro Met Leu Ala Tyr Pro Phe Tyr
225             230             235             240

TTG TGG AAC AGA AGT CCA GGG AAA CAA GGT TCT CAT TAT CAT CCG GAC     828
Leu Trp Asn Arg Ser Pro Gly Lys Gln Gly Ser His Tyr His Pro Asp
                245             250             255

AGT GAC TTG TTT CTT CCA AAA GAG AAG AAA GAT GTT CTG ACA TCA ACT     876
Ser Asp Leu Phe Leu Pro Lys Glu Lys Lys Asp Val Leu Thr Ser Thr
                260             265             270

GCC TGT TGG ACT GCA ATG GCT GCT TTG CTT GTT TGT CTC AAC TTT GTC     924
Ala Cys Trp Thr Ala Met Ala Ala Leu Leu Val Cys Leu Asn Phe Val
                275             280             285

ATG GGT CCA ATC CAG ATG CTC AAA CTA TAT GGC ATC CCT TAT TGG ATA     972
Met Gly Pro Ile Gln Met Leu Lys Leu Tyr Gly Ile Pro Tyr Trp Ile
            290             295             300

TTT GTA ATG TGG TTG GAC TTC GTC ACT TAC TTG CAC CAC CAT GGA CAT    1020
Phe Val Met Trp Leu Asp Phe Val Thr Tyr Leu His His His Gly His
305             310             315             320
```

FIG.12b

| | |
|---|---|
| GAA GAC AAG CTC CCT TGG TAT CGT GGA AAG GAA TGG AGT TAC CTG AGA<br>Glu Asp Lys Leu Pro Trp Tyr Arg Gly Lys Glu Trp Ser Tyr Leu Arg<br>                  325                           330                      335 | 1068 |
| GGA GGG CTC ACA ACA TTA GAT CGT GAC TAC GGA TGG ATC AAT AAC ATC<br>Gly Gly Leu Thr Thr Leu Asp Arg Asp Tyr Gly Trp Ile Asn Asn Ile<br>                  340                           345                      350 | 1116 |
| CAC CAC GAT ATT GGA ACT CAT GTG ATA CAT CAT CTT TTC CCG CAG ATC<br>His His Asp Ile Gly Thr His Val Ile His His Leu Phe Pro Gln Ile<br>                  355                           360                      365 | 1164 |
| CCA CAT TAT CAT CTA GTA GAA GCA ACA GAA GCA GCT AAA CCA GTA CTA<br>Pro His Tyr His Leu Val Glu Ala Thr Glu Ala Ala Lys Pro Val Leu<br>                  370                           375                      380 | 1212 |
| GGA AAG TAC TAC AGA GAA CCG AAA AAC TCT GGA CCT CTG CCA CTT CAC<br>Gly Lys Tyr Tyr Arg Glu Pro Lys Asn Ser Gly Pro Leu Pro Leu His<br>385                            390                           395                      400 | 1260 |
| TTA CTG GGA AGC CTC ATA AAG AGT ATG AAA CAA GAC CAT TTC GTA AGC<br>Leu Leu Gly Ser Leu Ile Lys Ser Met Lys Gln Asp His Phe Val Ser<br>                  405                           410                      415 | 1308 |
| GAT ACA GGA GAT GTC GTG TAC TAT GAG GCA GAT CCA AAA CTC AAT GGA<br>Asp Thr Gly Asp Val Val Tyr Tyr Glu Ala Asp Pro Lys Leu Asn Gly<br>                  420                           425                      430 | 1356 |
| CAA AGA ACA TGAGGACATA CTGCAGTGAA CCAGGCAGAC AAGTTACATA<br>Gln Arg Thr<br>                  435 | 1405 |
| AATTCATCTT GGCCCATTCA TTATGTTCTT TTTGTTTTGG TGTAAAGCCT TTTCGAGATT | 1465 |
| AAAAAAGCAT TAATTTGTAG AAACCTGTGG TAAAACTCTC GATCAAATGA AATAAGATAT | 1525 |

FIG.12c

```
Met Ala Ser Ser Val Leu Ser Glu Cys Gly Phe Arg Pro Leu Pro Arg
 1               5                  10                 15

Phe Tyr Pro Lys His Thr Thr Ser Phe Ala Ser Asn Pro Lys Pro Thr
            20                  25              30

Phe Lys Phe Asn Pro Pro Leu Lys Pro Pro Ser Ser Leu Leu Asn Ser
        35                  40                  45

Arg Tyr Gly Phe Tyr Ser Lys Thr Arg Asn Trp Ala Leu Asn Val Ala
    50                  55                  60

Thr Pro Leu Thr Thr Leu Gln Ser Pro Ser Glu Glu Asp Thr Glu Arg
65                  70                  75                  80

Phe Asp Pro Gly Ala Pro Pro Phe Asn Leu Ala Asp Ile Arg Ala
                85                  90                  95

Ala Ile Pro Lys His Cys Trp Val Lys Asn Pro Trp Met Ser Met Ser
            100                 105                 110

Tyr Val Val Arg Asp Val Ala Ile Val Phe Gly Leu Ala Ala Val Ala
        115                 120                 125

Ala Tyr Phe Asn Asn Trp Leu Leu Trp Pro Leu Tyr Trp Phe Ala Gln
130                 135                 140

Gly Thr Met Phe Trp Ala Leu Phe Val Leu Gly His Asp Cys Gly His
145                 150                 155                 160

Gly Ser Phe Ser Asn Asp Pro Arg Leu Asn Ser Val Ala Gly His Leu
            165                 170                 175

Leu His Ser Ser Ile Leu Val Pro Tyr His Gly Trp Arg Ile Ser His
            180                 185                 190

Arg Thr His His Gln Asn His Gly His Val Glu Asn Asp Glu Ser Trp
        195                 200                 205

His Pro Leu Pro Glu Ser Ile Tyr Lys Asn Leu Glu Lys Thr Thr Gln
210                 215                 220
```

FIG.13a

Met Phe Arg Phe Thr Leu Pro Phe Pro Met Leu Ala Tyr Pro Phe Tyr
225                230                235                240

Leu Trp Asn Arg Ser Pro Gly Lys Gln Gly Ser His Tyr His Pro Asp
            245                250                255

Ser Asp Leu Phe Leu Pro Lys Glu Lys Lys Asp Val Leu Thr Ser Thr
            260                265                270

Ala Cys Trp Thr Ala Met Ala Ala Leu Leu Val Cys Leu Asn Phe Val
            275                280                285

Met Gly Pro Ile Gln Met Leu Lys Leu Tyr Gly Ile Pro Tyr Trp Ile
            290                295                300

Phe Val Met Trp Leu Asp Phe Val Thr Tyr Leu His His His Gly His
305                310                315                320

Glu Asp Lys Leu Pro Trp Tyr Arg Gly Lys Glu Trp Ser Tyr Leu Arg
                325                330                335

Gly Gly Leu Thr Thr Leu Asp Arg Asp Tyr Gly Trp Ile Asn Asn Ile
            340                345                350

His His Asp Ile Gly Thr His Val Ile His His Leu Phe Pro Gln Ile
            355                360                365

Pro His Tyr His Leu Val Glu Ala Thr Glu Ala Ala Lys Pro Val Leu
            370                375                380

Gly Lys Tyr Tyr Arg Glu Pro Lys Asn Ser Gly Pro Leu Pro Leu His
385                390                395                400

Leu Leu Gly Ser Leu Ile Lys Ser Met Lys Gln Asp His Phe Val Ser
                405                410                415

Asp Thr Gly Asp Val Val Tyr Tyr Glu Ala Asp Pro Lys Leu Asn Gly
            420                425                430

Gln Arg Thr
435

FIG.13b

ALTERED LINOLENIC AND LINOLEIC ACID CONTENT IN PLANTS

This is a divisional application of application Ser. No. 08/432,147 filed May 5, 1995 (now U.S. Pat. No. 7,205,457), which is a §371 national stage of PCT/US94/01321 filed Feb. 4, 1994, which is a continuation-in-part of U.S. Ser. No. 08/156,551 filed Nov. 22, 1993 (now abandoned), which is a continuation of U.S. Ser. No. 08/014,431, filed on Feb. 5, 1993 (now abandoned). The present invention relates to genetically engineered plants. In particular it relates to genetically engineered plants and seeds which have altered linolenic and linoleic acid content compared with naturally occurring plants.

BACKGROUND

Many crop species produce seed oils in which the fatty acid composition is not ideally suited to the intended use. The application of conventional breeding methods, coupled in some cases with mutagenesis, has resulted in the production of new varieties of several species with desirable alterations in the fatty acid composition of seed oil. A notable example is the development of low erucic acid varieties of rapeseed (Stefansson 1983). Similar efforts have resulted in the reduction of the level of polyunsaturated 18-carbon fatty acids in soybean (Wilcox and Cavins 1985; Graef et al. 1988), sunflower (Fick 1989), and linseed oils (Green and Marshal 1984).

Most of the genetic variation in seed lipid fatty acid composition appears to involve the presence of an allele of a gene that disrupts normal fatty acid metabolism and leads to an accumulation of intermediate fatty acid products in the seed storage lipids (Downey 1987). However, it seems likely that, because of the inherent limitations of this approach, many other desirable changes in seed oil fatty acid composition may require the directed application of genetic engineering methods.

α-Linolenic acid ($18:3^{\Delta 9,12,15}$) is an eighteen carbon fatty acid containing three cis double bonds at the 9-10, 12-13 and 15-16 carbons. It is found in the cells of higher plants as a constituent of cell membranes. It is also found in storage organs, such as in seeds. There it is designated oil bodies which are bounded by an electron dense structure that is thought to be a half-unit membrane and dispersed in the cytoplasmic environment of cells. When present as a constituent of cell membranes, linolenic acid is usually esterified to the sn-1 or sn-2 position of the glycerol moiety of a diacylglycerolipid. By contrast, when present in oil bodies, linolenic acid is usually esterified to the sn-1, sn-2 or sn-3 position of a triacylglycerolipid (TAG).

Linolenic acid is extensively used in the paint and varnish industry in view of its rapid oxidation. Flax seed is a predominant source of this oil. Soybean seed, on the other hand, does not have sufficient linolenic acid content to be used in this industry. Thus, increasing the linolenic acid content in a plant such as soybean would permit the use of the soybean oil in the paint and varnish industry.

On the other hand, it is undesirable to have significant levels of linolenic acid in cooking oils and foods. Linolenic acid is unstable during cooking and is rapidly oxidized. The oxidized products impart rancidity to the finished product. A rapeseed or soybean oil with reduced linolenic acid, such as containing 2% or less of linolenic acid, would be ideal for use as a cooking oil.

Linolenic acid is also a precursor in the biosynthesis of jasmonic acid, an important plant growth regulator. Linolenic acid is converted to jasmonic acid by introduction of an oxygen to the carbon chain by a lipoxygenase, followed by dehydration, reduction, and several β-oxidations (Vick and Zimmerman, 1984). The activity of jasmonic acid has been measured in terms of induction of pathogen defense responses. By application of free linolenic acid to plants, plant pathogen defenses can also be induced (Farmer and Ryan, 1992).

A model has been proposed to explain the ability of free linolenic acid to exhibit the effects associated with jasmonic acid (Farmer and Ryan, 1992). It is hypothesized that all of the enzymatic activities which are required for the conversion of linolenic acid to jasmonic acid are constitutively present in the cell and the rate limiting step in the production of jasmonic acid is the availability of free linolenic acid. A likely route for the production of the free linolenic acid is by the activity of a lipase in the plasma membrane.

It has been observed that exogenous jasmonic acid can more powerfully activate defense responses than can wounding. This suggests that wounds cannot generate enough free linolenic acid to support high level production of jasmonic acid. The activity of the lipase or the availability of appropriate substrate for the lipase may be rate limiting upon wounding. Thus, increasing the linolenic acid content of plasma membrane may positively influence "signal transduction" in plants and result in better protection against environment and pathogen stress.

Linolenic acid, as well as oleic and linoleic acids are also important constituents, as well as precursors of volatile carbonyl compounds, whic contribute to the aroma of both fresh and cooked foods. The major fatty acids of tomato fruit pericarp are oleic, linoleic and linolenic acids. As the fruit ripens, the levels of the latter two fatty acids decline resulting in the production of a number of 4-6 carbon containing aldehydees and ketones. One particular metabolite, cis-3-hexanol, has been shown to be present in higher levels in vine-ripened tomatoes compared to supermarket tomatoes or tomatoes stored in refrigerators. It is likely, therefore, that the "aroma" of fresh fruits and vegetables can be "modulated" by regulation of the content of linolenic and linoleic acids, important substrates for the enzyme lipoxygenase and subsequently the hydroperoxide cleaving enzyme, which generates the volatile "aroma" compounds.

From the above, it is clear that the ability to vary the content of linolenic acid in plants would be desirable. However, to achieve this result it is necessary to determine what controls the product of linolenic acid in plants.

A large body of experimental evidence derived from radiochemical tracer studies has indicated that α-linolenic acid is synthesized by the desaturation of linoleic acid ($18:2^{\Delta 9,12}$) (reviewed in Harwood 1988;). However, the actual substrate for desaturation is not known.

In vivo and in vitro labelling studies suggest that there are possibly two distinct pathways for the synthesis of linolenic acid (Browse and Somerville, 1991). One possible pathway is thought to be located in the endoplasmic reticulum where linoleic acid esterified to the sn-2 position of phosphatidylcholine is a substrate for desaturation. However, the available evidence does not exclude the possibility that linoleic acid esterified to other lipids may also be a substrate.

A second possible pathway of linoleic acid desaturation is located in the plastid where the available evidence suggests that linoleic acid esterified to monogalactosyldiacylglycerol and, possibly, other plastid lipids is the substrate for desaturation.

Relatively little direct information is available concerning the enzymes involved in linoleic acid desaturation. Low levels of enzyme activity have been detected in microsomal membrane preparations from developing linseed (Linum ussitatum) (Browse and Slack, 1981) and, more recently, in preparations of gently lysed chloroplasts (Schmidt and Heinz, 1990a,b). The general features of the enzyme may be inferred from information available about other enzymes of this class.

The most thoroughly characterized desaturase is the stearoyl-Coenzyme A (CoA) desaturase from vertebrate liver (reviewed by Holloway, 1983). This enzyme has been shown to be an integral membrane protein which contains non-heme iron. The desaturase reaction requires fatty acyl-CoA, molecular oxygen and reduced cytochrome b5, another membrane protein. In vivo, the reduced cytochrome b5 is produced by the transfer of reducing equivalents from NADH via the activity of cytochrome b5 reductase, a flavin containing membrane protein.

The most thoroughly characterized desaturase from plants is the stearoyl-ACP desaturase (McKeon and Stumpf, 1982; Shanklin and Somerville, 1991). This enzyme also requires molecular oxygen and a high potential reductant. However, in contrast to the animal enzyme, this desaturase is a soluble plastid protein which preferentially acts on a fatty acid esterified to acyl carrier protein (ACP) rather than CoA. This enzyme also differs from the animal enzyme by utilizing reduced ferredoxin as an intermediate electron donor.

Other plant desaturases appear to be membrane proteins. The microsomal Δ12 oleate desaturase from several plant species has been assayed in membrane preparations from several plants (Harwood, 1988). As with the stearoyl-CoA desaturase from animals, this enzyme requires molecular oxygen and reduced cytochrome b5 as an electron donor (Kearns et al., 1991). However, it appears that oleate esterified to a phospholipid is the substrate rather than a CoA ester.

With regard to the activity responsible for the making of linolenic acid, little was known as to its source or origin. However, evidence that the amount of linolenic acid is related to the amount of linoleic acid desaturase activity has been obtained by analysis of the properties of the fad3 mutant of *Arabidopsis thaliana* (Lemieux et al. 1990). This mutant is deficient in linolenic acid in the storage oils of its seed lipids and in the membrane lipids of different tissues to varying degrees. The mutant also had an increase in the amount of linoleic acid. This can be interpreted as evidence that the mutant is defective in the activity of a desaturase which converts linoleic acid to linolenic acid.

There is further evidence to suggest that the activity of this desaturase could be rate limiting for linolenic acid synthesis under normal circumstances. This was discovered by measuring the effects on fatty acid composition in heterozygous plants (i.e., fad3+/fad−) formed by crossing the wild type with the fad3 mutant. In these F1 plants, which have one copy of the normal fad3 gene product instead of the two normally found in the wild type, the amount of linolenic acid was almost exactly intermediate between that found in either parent. This suggests that the amount of linolenic acid is proportional to the amount of functional fad3 gene product (Lemieux et al., 1990).

These results do not shed any light, however, on the nature of the fad3 gene product or whether the observed effects in mutants are related to either a decrease in quantitiy of desaturase protein or desaturase activity due to a defective protein.

Moreover, nothing is known with any degree of certainty about the linoleic acid desaturase from plant microsomes. As noted above, very little is known about the microsomal desaturases except that they probably utilize reduced cytochrome b5 as intermediate electron donor and probably utilize lipids rather than CoA or ACP esters as substrates.

Moreover, as in many other aspects of plant biology, the lack of specific information about the biochemistry and regulation of lipid metabolism makes it difficult to predict how the introduction of one or a few genes might usefully alter seed lipid synthesis.

An additional problem arises from the fact that many of the key enzymes of lipid metabolism are membrane-bound and present in low quantities. Thus, attempts to solubilize and purify them from plant sources have not been successful.

SUMMARY OF THE INVENTION

The present invention provides structural coding sequences encoding linoleic acid desaturase activity which can be used to alter the linoleic and linolenic acid compositions of plants or to isolate other plant linoleic acid desaturases. The present invention further provides a plant capable of expressing a structural coding sequence to control the level of linolenic acid or linoleic acid or both in the plant. The present invention further provides a method for controlling the levels of linoleic and linolenic acid in plants. It is also demonstrated by the present invention that the linoleic acid desaturase enzyme activity in plant cells and tissues is a controlling step in linolenic acid biosynthesis.

The present invention further relates to the engineering of two advantageous traits into plants: increased and decreased α-linolenic acid content in the structural lipids or storage oils of various crop plants.

In accomplishing the foregoing, there is provided, in accordance with one aspect of the present invention, a genetically transformed plant which has an elevated linolenic acid content comprising a recombinant, double-stranded DNA molecule comprising (i) a promoter that functions in plant cells to cause the production of an RNA sequence, said promoter operably linked to;

(ii) a structural coding sequence that causes the production of an RNA sequence that encodes a linoleic acid desaturase activity; and (iii) a 3' non-translated region that functions in plant cells to promote polyadenylation to the 3' end of said RNA sequence.

In accordance with another aspect of the present invention, there is provided a genetically transformed plant which has a reduced linolenic acid content, comprising a recombinant, double-stranded DNA molecule comprising (i) a promoter that functions in plant cells to cause the production of an RNA sequence, said promoter operably linked to;

(ii) a DNA sequence that causes the production of an RNA sequence that is in antisense orientation to at least a portion of a gene that encodes a linoleic acid desaturase activity in said plant; and (iii) a 3' non-translated region that functions in plant cells to promote polyadenylation to the 3' end of said RNA sequence.

There has also been provided, in accordance with another aspect of the present invention a method of producing a genetically transformed plant which has an elevated or reduced linolenic acid content. There has also been provided, in accordance with another aspect of the present invention a recombinant, double-stranded DNA molecule and plant cells containing a recombinant, double-stranded DNA molecule.

BRIEF DESCRIPTION OF THE DRAWINGS

FIG. 3 shows the nucleotide sequence (SEQ ID NO:1) and deduced amino acid sequence (SEQ ID NO:2) for the linoleic acid desaturase cDNA (fad3) from *B. napus.*

FIG. 4 shows a comparison of the deduced amino acid sequence of one linoleic acid desaturase cDNA (fad3) from *B. napus* and the desA gene from *Synechocystis*. Identical residues are indicated by a solid box. Conservative substitutions are indicated by a stippled box.

FIG. 10 shows the nucleotide sequence (SEQ ID NO:9) for the linoleic acid desaturase cDNA (fadD) from *Arabidopsis.*

FIG. 11 shows the deduced amino acid sequence (SEQ ID NO:10) for the linoleic acid desaturase cDNA (fadD) from *Arabidopsis.*

FIG. 12 shows the nucleotide sequence (SEQ ID NO:11) for the linoleic acid desaturase cDNA (fadE) from *Arabidopsis.*

FIG. 13 shows the deduced amino acid sequence (SEQ ID NO:12) for the linoleic acid desaturase cDNA (fadE) from *Arabidopsis.*

DETAILED DESCRIPTION OF THE INVENTION

Figure 1:
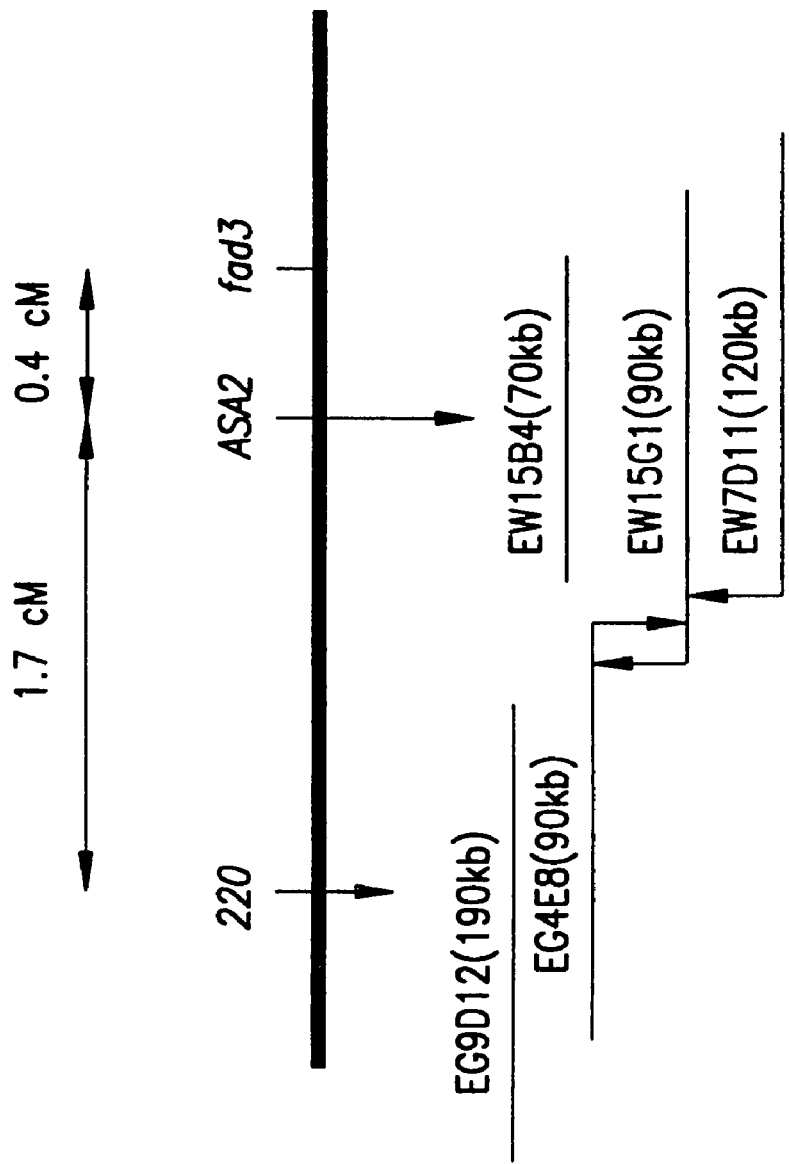
FIG. 1 shows the genetic map of the region of chromosome 2 of *Arabidopsis thaliana* where a linoleic acid desaturase gene is located and the identity of the yeast artificial chromosomes which carry this region of the genome.

A genetically transformed plant of the present invention which has an altered linolenic or linoleic acid content can be obtained by expressing the double-stranded DNA molecules described in this application.

The expression of a double-stranded DNA involves transcription of messenger RNA (mRNA) from one strand of the DNA by RNA polymerase enzyme, and the subsequent processing of the mRNA primary transcript inside the nucleus. This processing involves a 3' non-translated region which adds polyadenylate nucleotides to the 3' end of the RNA.

Promoters

Transcription of DNA into mRNA is regulated by a region of DNA usually referred to as the "promoter." The promoter region contains a sequence of bases that signals RNA polymerase to associate with the DNA, and to initiate the transcription of mRNA using one of the DNA strands as a template to make a corresponding complementary strand of RNA.

Any promoter which is known or is found to cause transcription of RNA in plant cells can be used in the present invention. Promoters which are useful in the present invention include any promoter that functions in a plant cell to cause the production of a RNA sequence. A number of promoters which are active in plant cells and are capable of producing a RNA sequence have been described in the literature. These include the nopaline synthase (NOS) and octopine synthase (OCS) promoters (which are carried on tumor-inducing plasmids of *Agrobacterium tumefaciens*), the caulimovirus promoters such as the cauliflower mosaic virus (CaMV) 19S and 35S and the figwort mosaic virus 35S-promoters, the light-inducible promoter from the small subunit of ribulose-1,5-bisphosphate carboxylase (ssRUBISCO, a very abundant plant polypeptide), and the chlorophyll a/b binding protein gene promoter, etc. All of these promoters have been used to create various types of DNA constructs which have been expressed in plants; see, e.g., PCT publication WO 84/02913 (Rogers et al., Monsanto).

Promoters may be obtained from a variety of sources such as plants and plant viruses. Promoters can be used in the form that they exist as isolated from plant genes such as ssRUBISCO genes, or can be modified to improve their effectiveness, such as with the enhanced CaMV35S promoter.

Those skilled in the art will recognize that the amount of linoleic acid desaturase needed to induce the desired alteration in linolenic acid content may vary with the type of plant. It is also possible that extremes in linoleic acid desaturase activity may be deleterious to the plant. Therefore, in a preferred embodiment, promoter function should be optimized by selecting a promoter with the desired tissue expression capabilities and approximate promoter strength and selecting a transformant which produces the desired linoleic acid desaturase activity in the target tissues.

This selection approach from the pool of transformants is routinely employed in expression of heterologous structural genes in plants since there is variation between transformants containing the same heterologous gene due to the site of gene insertion within the plant genome. (Commonly referred to as "position effect").

In a preferred embodiment, the promoters utilized in the double-stranded DNA molecules should have relatively high expression in tissues where the increased or decreased linolenic acid content is desired, such as the seeds of the plant. In Canola, a particularly preferred promoter in this regard is the seed specific promoter described herein in greater detail in the accompanying examples.

In another preferred embodiment, the promoter used in the expression of the double-stranded DNA molecules of the present invention can be a constitutive promoter, expressing the DNA molecule in all or most of the tissues of the plant. However, the promoter selected for this embodiments should not cause expression at levels which are detrimental to plant health, growth and development.

β-conglycinin (also known as the 7S protein) is one of the major storage proteins in soybean (*Glycine max*) (Meinke et al., 1981). The 7S (β-conglycin) α'-subunit promoter, used in one aspect of this study to express the linoleic acid desaturase gene, has been shown to be both highly active and seed-specific (Doyle et al, 1986 and Beachy et al., 1985). The β-subunit of β-conglycinin has been expressed, using its endogenous promoter, in the seeds of transgenic petunia and tobacco, showing that the promoter functions in a seed-specific manner in other plants (Bray et al., 1987). The promoter for β-conglycinin could be used to in accordance with the present invention. If used, this promoter could express the DNA molecule specifically in seeds, which could lead to an alteration in the linolenic acid content of the seeds.

In addition, the endogenous plant linoleic acid desaturase promoters can be used in the present invention. These promoters should be useful in expressing a linoleic acid desaturase gene in specific tissues, such as leaves, seeds or fruits. A number of other promoters with seed-specific or seed-enhanced expression are known and are likely to be expressed in seeds, which are oil accumulating cells. For illustration, the napin promoter and the acyl carrier protein promoters have been utilized in the modification of seed oil by antisense expression (Knutson et al., 1992).

The linolenic acid content of root tissue can be increased by expressing a linoleic acid desaturase gene behind a promoter which is expressed in roots. The promoter from the acid chitinase gene (Samac et al., 1990) is known to function in root tissue and could be used to express the linoleic acid desaturase in root tissue. Expression in root tissue could also be accomplished by utilizing the root specific subdomains of the CaMV35S promoter that have been identified. (Benfey et al., 1989). The linolenic acid content of leaf tissue can be increased by expressing the linoleic acid desaturase gene using a leaf active promoter such as ssRUBISCO promoter or chlorophyll a/b binding protein gene promoter.

The linolenic acid content of fruits can be increased by expressing a linolenic acid desaturase gene behind a promoter which is functional in fruits. Such promoters could be either expressed at all developmental stages of the fruit or restricted to specific stages, particularly fruit ripening.

The RNA produced by a DNA construct of the present invention can also contain a 5' non-translated leader sequence. This sequence can be derived from the promoter selected to express the gene, and can be specifically modified so as to increase translation of the mRNA. The 5' non-translated regions can also be obtained from viral RNAs, from suitable eukaryotic genes, or from a synthetic gene sequence. The present invention is not limited to constructs, as presented in the following examples, wherein the non-translated region is derived from the 5' non-translated sequence that accompanies the promoter sequence. Rather, the non-translated leader sequence can be derived from an unrelated promoter or coding sequence as discussed above.

Linoleic Acid Desaturase Structural Coding Sequences

The structural coding sequence that causes the production of an RNA sequence that encodes a linoleic acid desaturase activity can be the sequences disclosed in the present application, or any sequence that can be obtained using the sequences disclosed in the present application, or any sequence that can be isolated using the method disclosed in the present application.

The structural coding sequence can also be a part of or from the structural coding sequences disclosed in the present invention. It is possible that the active part of the linoleic acid desaturase is formed using only part of the structural coding sequences disclosed in the present application.

The structural coding sequences can be obtained from a variety of sources, such as algae, bacteria or plants. Preferably, structural coding sequences obtained from plants are used in accordance with the present invention.

Since virtually nothing was known about the properties of the linoleic acid desaturase structural coding sequence prior to the present invention, the method used in the present invention to isolate the structural coding sequence was based on the concept of map based cloning. The essential concept in map based cloning is to use information about the genetic map position of a structural coding sequence to isolate the region of the chromosome surrounding the structural coding sequence, and then to use the isolated DNA to complement a mutation in the structural coding sequence. This strategy has never previously been reported in the isolation of any plant gene.

In order to implement map based cloning of the linoleic acid desaturase, mutants of *Arabidopsis thaliana* (L.) deficient in linoleic acid desaturase activity were isolated by screening randomly chosen individuals from mutagenized populations of plants for individual plants with altered leaf or seed fatty acid composition. (Browse et al. 1985; Lemieux et al. 1990). By screening thousands of plants for altered fatty acid composition, mutants with decreased amounts of linolenic acid and increased amounts of linoleic acid in leaf and seed lipids were isolated. Physiological and genetic analyses of these mutants indicated that they fell into three complementation groups designated fad3, fadD and fadE.

The fad3 mutants had very reduced levels of linolenic acid in seeds and roots but had almost normal levels of linolenic acid in leaves. This effect was interpreted as evidence that the fad3 locus encoded a microsomal desaturase which was responsible for desaturation of linoleic acid to linolenic acid on lipids made by the pathway of lipid biosynthesis in the endoplasmic reticulum, designated the "eukaryotic pathway" (Lemieux et al. 1990). This pathway is mostly responsible for the synthesis of lipids in non-green tissues such as seeds and roots, but plays a secondary role in leaves and other green tissues. Thus, a mutation in the fad3 gene would not be expected to have a major effect on the desaturation of leaf lipids.

In contrast to the fad3 mutant, the fadD mutant had almost normal fatty acid composition of roots and seeds, but had a strong reduction in the amount of linolenic acid in leaf lipids, and a corresponding increase in the amount of linoleic acid. (Browse et al., 1986). Thus, this mutant had the properties expected of a mutant deficient in a linoleic acid desaturase from the prokaryotic pathway which is primarily responsible for the synthesis of lipids in green tissues.

An unusual property of the fadD mutants was that they were very deficient in linoleic acid content when grown at temperatures above about 22° C. but had almost normal fatty acid composition when grown at temperatures below about 18° C. (McCourt et al., 1987). Since it was very unlikely that several independently isolated mutations would all give rise to a temperature conditional phenotype, it was concluded that a second desaturase must be partially responsible for desaturating linoleic acid to linolenic acid in green tissues. Therefore, the fadD mutant was remutagenized with ethylmethane sulfonate, self-fertilized to produce a segregating population of mutagenized plants (designated the M2 generation), and this population was screened for a mutant which was deficient in linolenic acid in green tissues at low temperatures. A mutant with this property was isolated and the mutation responsible for this effect was designated the fadE locus (Somerville and Browse, unpublished).

Isolation of the Linoleic Acid Desaturase Gene from Canola

The following example was used to isolate the structural coding sequence from the fad3 region. The method described herein could equally have been used to isolate either the fadD or fadE region.

In order to approximately locate the fad3 mutation of the genetic map of *Arabidopsis*, a sexual cross was made between the fad3 mutant line BL1 and the multiply marked mutant line W1 (Hugly et al., 1991). The F1 hybrids from this cross were permitted to self-fertilize and the resulting F2 plants were scored for both the segregating genetic markers and the altered fatty acid composition. The results of this analysis indicated that the fad3 mutation was located on chromosome 2 near the marker erecta. In order to obtain a more accurate map position by RFLP mapping, a second sexual cross was made between the fad3 mutant line BL1 and the Niederzenz race of *Arabidopsis*. The F1 progeny were permitted to self-fertilize to produce the F2 generation. 137 F2 plants were grown during 3 weeks at 22° C. (100 µE/m²/s) in order to produce fully expanded rosettes, and a few leaves (representing a total weight of 0.2-0.5 g per plant) were harvested from each plant in order to prepare DNA from them.

The leaves were frozen in liquid nitrogen, and ground in dry ice, using a mortar and a pestle. For each sample, the frozen powder was transferred to a microfuge tube and an equal amount of 2×CTAB buffer (2% cetyltrimethyl ammonium bromide (CTAB), 100 mM Tris-HCl pH 8, mM EDTA, 1.4 M NaCl, 1% polyvinylpolypyrrolidone (PVP) 40,000) was added. The tubes were left at room temperature for 5 min to allow the powder to thaw. The homogenate was extracted once with a mixture of chloroform-isoamyl alcohol (24:1, v/v), and 1/10 vol of 10×CTAB (10% CTAB, 0.7 M NaCl) buffer was added to the aqueous phase, which was then reextracted with an equal volume of chloroform isoamyl alcohol (24:1, v/v). The aqueous phase was transferred to a fresh microfuge tube and 1.5 vol of CTAB precipitation buffer (1% CTAB, 50 mM Tris-HCl pH 8, 10 mM EDTA) was added. The DNA was allowed to precipitate for 12 hr at 4 degrees, and collected by centrifugation (5 min at 10 000 g). The DNA was resuspended in 100 µl of 10 mM Tris-HCl pH 7.5, 1 mM EDTA, 1 M NaCl, and 100 µg/ml RNase A and incubated at 50° C. for 30 min. The DNA was precipitated by adding 2.2 vol of ethanol and incubating on ice for 20 min. The DNA was collected by centrifugation and the pellet was washed once with 1 ml of 70% ethanol, dried under vacuum for 3 min and resuspended in 10 µl of distilled water. The DNA was stored at −20° C. until use.

The 137 plants were grown to maturity and their seeds were collected individually. The fatty acid composition of 10 individual seeds from each of the F2 plants was measured as described by Browse et al (1986) in order to score the fad3 phenotype of each plant. Each seed was incubated in 1 ml of 1N HCl in methanol for 1 h at 80° C. The tubes were cooled to room temperature and 1 ml of 0.9% NaCl plus 0.3 ml of hexane were added. The tubes were agitated by vortexing and the phases separated by centrifugation (300×g for 5 min). The hexane phase was saved, evaporated under a stream of nitrogen, and the fatty acid methyl esters were dissolved in 50 µl hexane. An aliquot (2 µl) was injected onto the gas chromatograph and the fatty acid methyl esters separated and quantitated by flame ionization as described (Browse et al., 1986).

The DNA samples (1 µg) were then cut with the appropriate restriction enzyme (EcoR1 for the marker # 220, Bgl2 for the marker ASA2) using a concentration of 1×KGB buffer (Sambrook et al, 1989), 5 units of the restriction endonuclease and 100 µg/ml BSA. The volume of each sample was 10 µl and the incubation was performed at 37° C. for 4 h. The fragments were resolved by agarose gel electrophoresis (0.8% agarose in 1×TAE buffer; Sambrock et al., 1989) and transferred to nylon filters (hybond N+), using the alkaline transfer method as described by the manufacturer. The nylon filters were probed (according to Church and Gilbert, 1984) with radioactively labelled fragments of DNA (Sambrock et al., 1989) corresponding to known RFLP markers which had previously been mapped in the approximate vicinity of the fad3 locus on chromosome 2. The RFLP markers 220 (Chang et al 1988) and ASA2 were found to map close to the fad3 locus. Analysis of the pattern of recombinants (Table 1) indicated that both ASA2 and 220 were located on the same side of the fad3 locus at distances of 0.4 and 2.2 centimorgans (cM), respectively.

TABLE 1

| # of plants | 220 | ASA2 | fad3 |
| --- | --- | --- | --- |
| 67 | H | H | +/− |
| 30 | L | L | −/− |
| 34 | N | N | +/+ |
| 3 | H | N | +/+ |
| 1 | L | H | +/− |
| 1 | N | H | +/− |
| 1 | H | H | −/− |

Table 1 shows the genotype of the F2 plants used for mapping the fad 3 locus. L is for Landsberg (background of the fad 3 mutant), N is for Niederzenz, H for heterozygous. A total of 137 F2 plants were analyzed. The number of recombinant plants between fad3 and 220 or ASA2 was 6 and 1 respectively.

In order to isolate the region of the chromosome containing the fad3 locus, the RFLP markers 220 and ASA2 were used as hybridization probes to screen several yeast artificial chromosome (YAC) libraries. (Grill and Somerville, 1991; Ward and Jen, 1990). The YAC filters were prepared according to Grill and Somerville (1991). The library was replicated onto nylon filters disposed on petri dishes of SC—(synthetic complete medium minus tryptophan and uracil; Sherman et al., 1986). The cells were allowed to grow for 12 h at 30° C., and the filters were transferred for 15 min on a Whatman 3 MM paper saturated with 1 M sorbitol, 50 mM DTT, 50 mM EDTA (pH 8).

The cell wall of the cells was then digested with lyticase, by incubating the filters on a Whatman paper saturated with 1M sorbitol, 50 mM EDTA and 2 mg/ml lyticase (Sigma Co., St. Louis, Mo.) for 12 h at 30° C. The filters were then transferred on a Whatman 3 MM paper saturated with 0.5 M NaOH, 1.5 M NaCl for 15 min, neutralized with 0.5 M Tris-HCl pH 8 for 15 min and quickly rinsed in 2×SSC (SSC is 10 mM sodium citrate, 150 mM NaCl, pH 7). The filters were allowed to dry, and were transferred to a vacuum oven at 80° C. for 1 h. They were subsequently hybridized according to Church and Gilbert (1984), with probes labelled with $^{32}P$ according to Sambrook et al. (1989).

The DNA of RFLP probe 220 was prepared from 100 ml of liquid culture lysate using the lambdasorb procedure (Promega Corp., Madison, Wis.); the cDNA encoding ASA2 was excised from the original plasmid (pKN140C; obtained from Dr. G. Fink, Whitehead Institute, Cambridge, Mass.) with Hind3 and cloned into the Hind3 site of pBLUESCRIPT. The plasmid DNA was then purified by Cesium chloride gradients according to Sambrook et al (1989), digested with Hind3 and the DNA insert was gel purified twice by electroelution according to Sambrook et al (1989).

In order to probe the libraries, the whole DNA from RFLP220 was used as a hybridization probe. By contrast, only the DNA insert of ASA2 was used as a probe. The RFLP probe 220 hybridized to YAC EG4E8 and EG9D12. The probe ASA2 hybridized to YACs EW15G1, EW15B4 and EW7D11.

In order to determine if these YACs contained all of the DNA between RFLP220 and ASA2, small regions of DNA from the ends of the inserts in EG4E8 and EW15G1 were prepared by inverse PCR (Grill and Somerville, 1991). For that purpose, DNA was prepared from the appropriate YAC clones. The clones (single colonies) were grown to saturation in SC—liquid cultures, and 1 ml of these cultures was used to inoculate 40 ml liquid cultures (in SC—medium) that were allowed to grow for 16 h at 30° C. The cells were collected by centrifugation, washed once in 1 M sorbitol, 50 mM EDTA, resuspended in 200 μl of 1 M sorbitol, 50 mM EDTA, 100 mM sodium citrate pH 5.8, 2 mM β-mercaptoethanol and 2 mg/ml lyticase, and incubated 2 h at 30° C.

Next, 350 μl of 2×CTAB buffer was added and the DNA was purified as described above. DNA (5 μg) of each clone was digested separately with HincII, AluI, EcoRV and RsaI (in 1×KGB buffer, at 37° C. for 4 h; final volume: 50 μl). The reactions were stopped by heating at 65° C. for 15 min, extracted once with one volume of phenol saturated with TE pH 8, followed by an extraction with 1 volume of chloroform-isoamyl alcohol mixture (24:1, vol/vol). The DNA was recovered by ethanol precipitation and resuspended in sterile distilled water. The ligation reactions were performed using 300 ng of DNA in a final volume of 50 μl. The reactions were carried out in 50 mM Tris-HCl pH 7.4, 10 mM MgCl2, 1 mM DTT, 1.2 mM ATP with 1 U of ligase, for 2 h at 20° C., and stopped by heating at 68° C. for 30 min.

The PCR reactions were carried out as follows: The buffers used were the ones indicated by the suppliers except for the Perkin Elmer enzyme for which the reaction was supplemented with an additional 1.4 mM $MgCl_2$ (final concentration 2.9 mM Mg). The dNTP final concentration was 125 μM when the Perkin Elmer enzyme was used and 200 μM with the Taq polymerases from other sources. In all cases, 100 ng of each oligonucleotide was used. The final volume was 100 μl. When no product was obtained, the reactions were carried out again in the same conditions except that formamide was added to a final concentration of 3%.

The left end was amplified from the ligation products of the EcoRV and RsaI digests, using the oligonucleotides EG1 (GGCGATGCTGTCGGAATGGACGATA) (SEQ. ID NO. 3) and EG2 (CTTGGAGCCACTATCGACTACGCGATC) (SEQ. ID NO. 4).

The right end of the clones obtained from the EG library was amplified from the ligation products of the AluI and HincII digests, using the oligonucleotides EG3 (CCGATCT-CAAGATTACGGAAT) (SEQ. ID NO. 5) and EG4 (TTC-CTAATGCAGGAGTCGCATAAG) (SEQ. ID NO. 6).

The right end of the clones obtained from the EW YAC library was amplified using the oligonucleotides H1 (AG-GAGTCGCATAAGGGAG) (SEQ. ID NO. 7) and H2 (GG-GAAGTGAATGGAGAC) (SEQ. ID NO. 8), using the same cycle conditions as above, except that the annealing temperature was reduced to 50° C.

After the reactions were completed, 5 μl of each mixture were electrophoresed on an agarose gel to separate the amplification product from primers. The slice of agarose that contained the amplified band was excised from the gel and melted in 1 ml of distilled water. Large amounts of product could then be produced, by reamplification of 5 μl of the melted slice. The PCR products were then purified by electroelution or by using GeneClean (Bio101) and used as hybridization probes to probe filters containing the isolated YAC DNA restricted by several enzymes. The probe made from the right end of EW15G1 hybridized to EG4E8 and similarly, a probe from the right end of EG4E8 hybridized to EW15G1. Thus, it was concluded that the YACs EG4E8 and EW15G1 contained all of the DNA in the region of the chromosome between RFLP220 and ASA2.

The size of the YAC clones was estimated by field inversion electrophoresis (CHEF, Vollrath and Davis, 1987). High molecular weight DNA was prepared as follows: the yeast cells which contained the YAC clones were grown and treated with lyticase as for preparing DNA as described above. The spheroplasts were then resuspended in an equal volume of 1M sorbitol, 50 mM EDTA, 1% low melt agarose at 37° C. The mixture was poured in a mould (Biorad) which was set on ice to allow the agarose to harden.

The resulting plugs were incubated for 12 h in 0.5 M EDTA pH 9, 1% lauryl sarcosine 1 mg/ml Proteinase K at 50° C. The plugs were subsequently washed twice in 50 mM EDTA and stored at 4° C. until use. The CHEF gel was run in 1×TBE for 16 h at 200 V, with a switching interval of 20 s; the temperature of the buffer was maintained at 14° C. during the run. The sizes of the YACs were determined by comparison with a lambda ladder and the yeast chromosomes, and were as follows: EG4E8, 90 kb; EG9D12, 190 kb; EW15G1, 90 kb; EW15B4, 70 kb, EW7D11, 125 kb. These sizes permitted us to roughly determine a correspondence between physical and genetic distances: the distance that separates 220 from ASA2 cannot exceed 180 kb, the sum of the size of the 2 YACs EG4E8 and EW15G1. Since the corresponding genetic distance is 1.7 cM, one can roughly estimate that, in this particular cross and in this particular region of the genome, the value of 1 cM is close to 100 kb. Thus, since the fad3 gene maps only 0.4 cM away from ASA2, the corresponding physical distance should be close to 40 kb. We then concluded that fad3 was probably located on the YAC EW7D11, which is the largest YAC hybridizing with ASA2. See FIG. 1.

In order to test the possibility that the YAC EW7D11 carried the fad3 gene, the YAC was used to probe a cDNA library made from developing seeds of Canola (*Brassica napus* L.). Even though the YAC was isolated from *Arabidopsis*, the fact that *Arabidopsis* and *B. napus* are both members of the family Cruciferae led us to predict that the homologous genes from these two species would be sufficiently identical at the nucleotide sequence level so that the *Arabidopsis* gene would hybridize to the *B. napus* gene. We also assumed that, because it catalyzes a chemically similar reaction to the stearoyl-ACP desaturase, it would be expressed at similar moderately high levels in developing seeds (Shanklin and Somerville, 1991). Since EW7D11 contained only about 0.2% of the total genome, we expected it to contain only about 2 moderately abundantly expressed genes (i.e., genes in which the mRNA is between 0.1 and 0.01% of total mRNA).

DNA of YAC EW7D11 was isolated as follows: high molecular weight DNA was prepared from the yeast cells that contained the YAC EW7D11 as described above, and several preparative low-melt agarose CHEF gels were run in 1×TBC buffer (same as TBE except that CDTA was substituted for EDTA). The slices that contained the YAC were excised from the gels and pooled. Three slices were melted at 65° C. and extracted with an equal volume of phenol saturated with TE. The aqueous phase was saved and reduced to 0.5 ml by repeated extractions with isobutyl alcohol. The remaining agarose was removed by several phenol extractions, followed by two chloroform-isoamyl alcohol extractions. The DNA was precipitated by adding 2 μg of linear acrylamide as a carrier plus 10 μl of 5M NaCl and 1.1 ml of ethanol, and incubating 20 min at 0° C. The DNA pellet was recovered by centrifugation, washed in 70% ethanol, dried under vacuum and resuspended in 50 μl of distilled water. The DNA (50 ng) was radioactively labelled and used to probe a cDNA library in λgt11.

The nitrocellulose filters were processed as described in Sambrook et al (1989). Duplicate filters were used, and the films were exposed 5-7 days in order to obtain a good signal. From among 200,000 plaques screened in this way, 31 hybridized to EW7D11. Among these 31 clones, 17 were homologous to each other, as checked by cross hybridization in stringent conditions. The size of the inserts in the 17 clones was estimated and the clone with the largest cDNA was retained for further analysis. A small scale preparation of this phage was prepared using the lambdasorb method, and the insert was excised by restricting with EcoR1. This insert was ligated into a pBLUESCRIPT II vector linearized with EcoRI, and the ligation mixture was used to transform *E. coli* strain DH5α.

Figure 2:
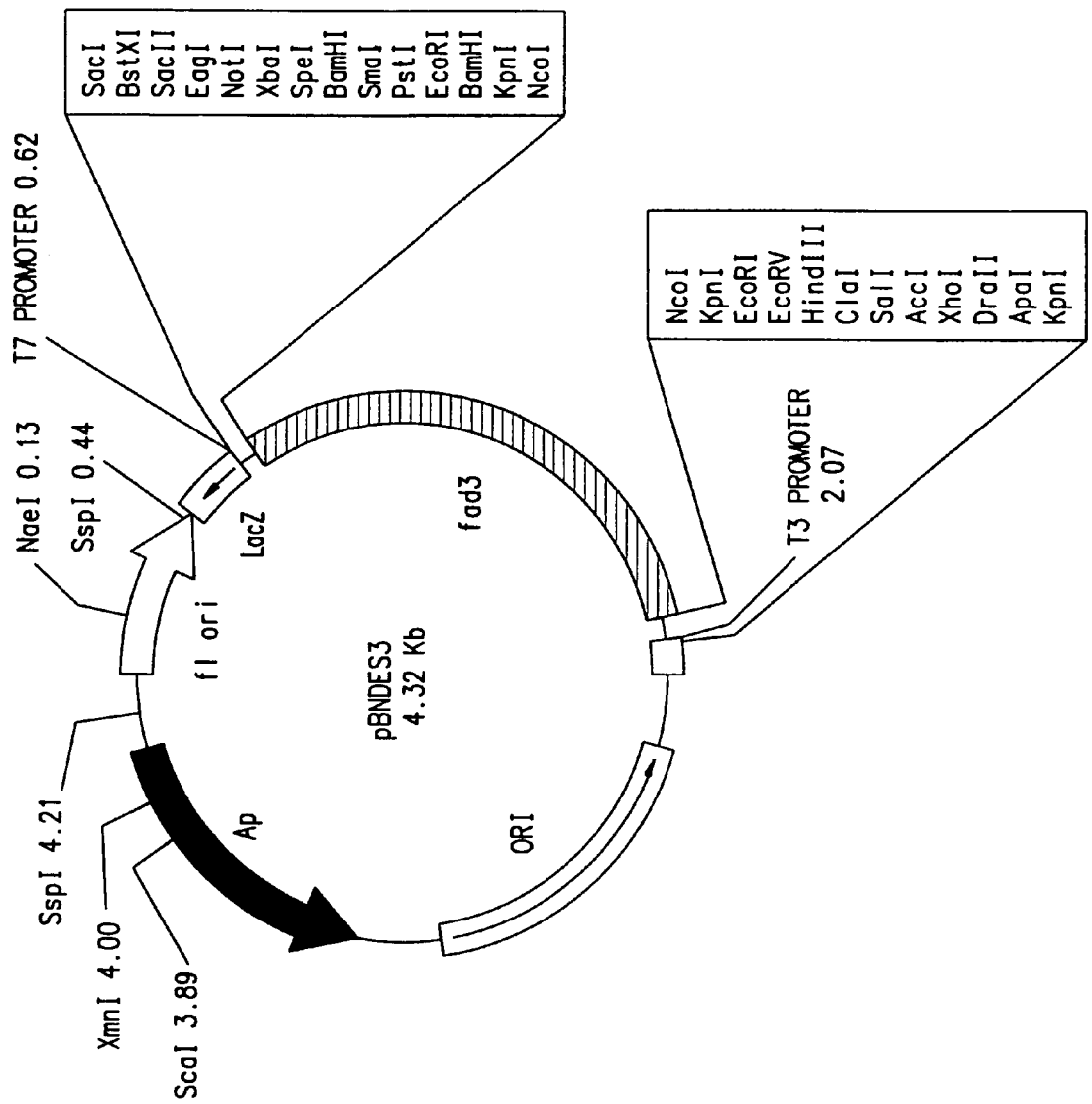
FIG. 2 shows the structure of plasmid pBNDES3 which was obtained by inserting an EcoRI fragment containing the *B. napus* linoleic acid desaturase cDNA (fad3) into pBLUE-SCRIPT.

One of the recombinant clones was designated pBNDES3 (FIG. 2), and retained for sequencing. The sequence was determined on both strands, using the sequenase enzyme, (US Biochemicals, Cleveland, Ohio) according to the instructions provided by the supplier. The nucleotide sequence of the insert in pBNDES3 is presented as FIG. 3. The deduced amino acid sequence of the largest open reading frame in the nucleotide sequence is also shown in FIG. 3.

Comparison of the deduced amino acid sequence of the 383 amino acid open reading frame in clone pBNDES3 against the known sequences in GenBank release 70 was performed using the FASTA program (Lipman and Pearson, 1985). This analysis revealed that the sequence from pBNDES3 had a region of significant homology to a previously characterized desaturase gene from the cyanobacterium *Synechocystis* (FIG. 4). (Wada et al. 1990). This was considered suggestive evidence that the clone pBNDES3 encoded a desaturase which was probably the fad3 structural coding sequence product. This was subsequently confirmed by a genetic complementation experiment.

Figure 5:
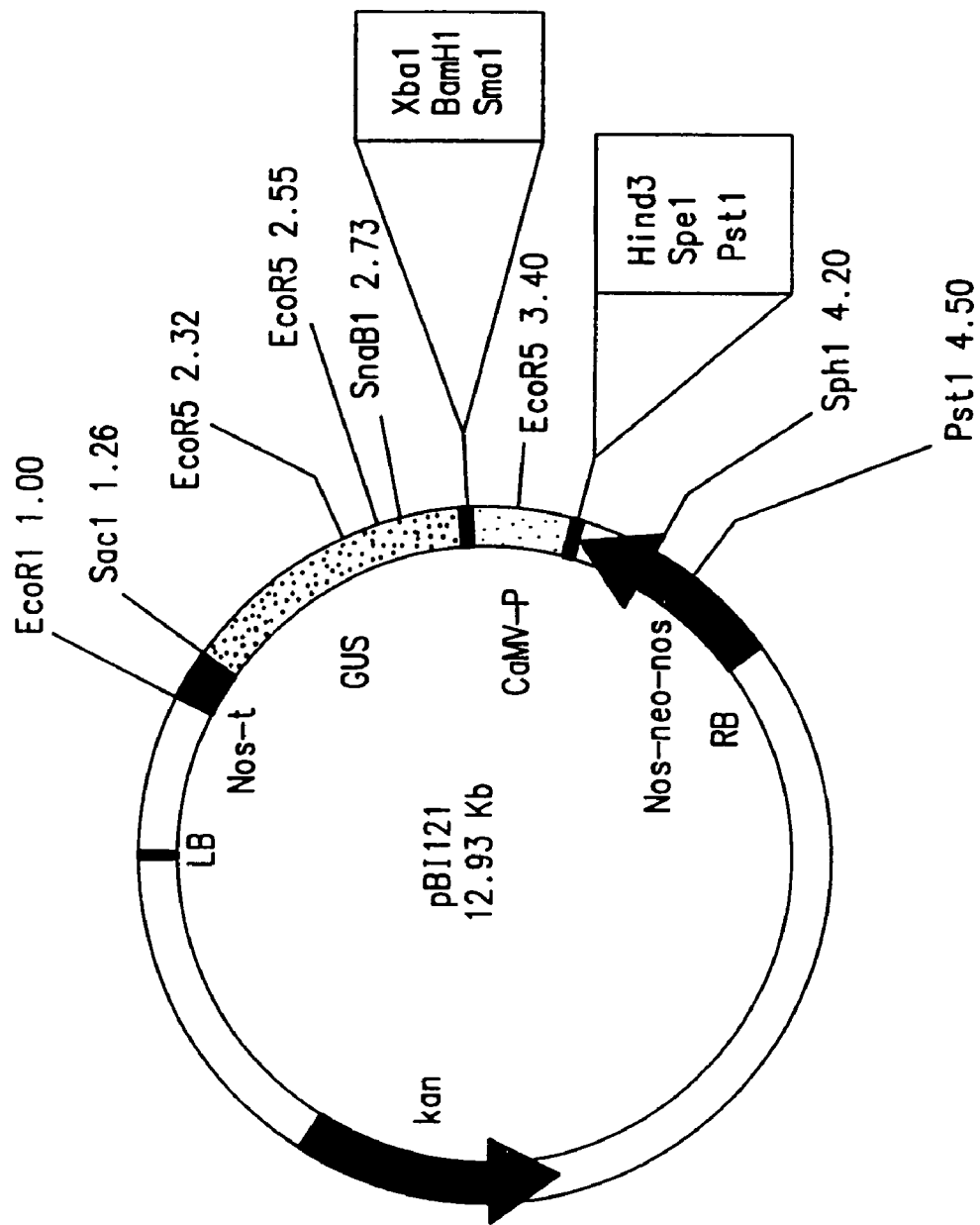
FIG. 5 shows the binary Ti plasmid vector pBI121.
Figure 6:
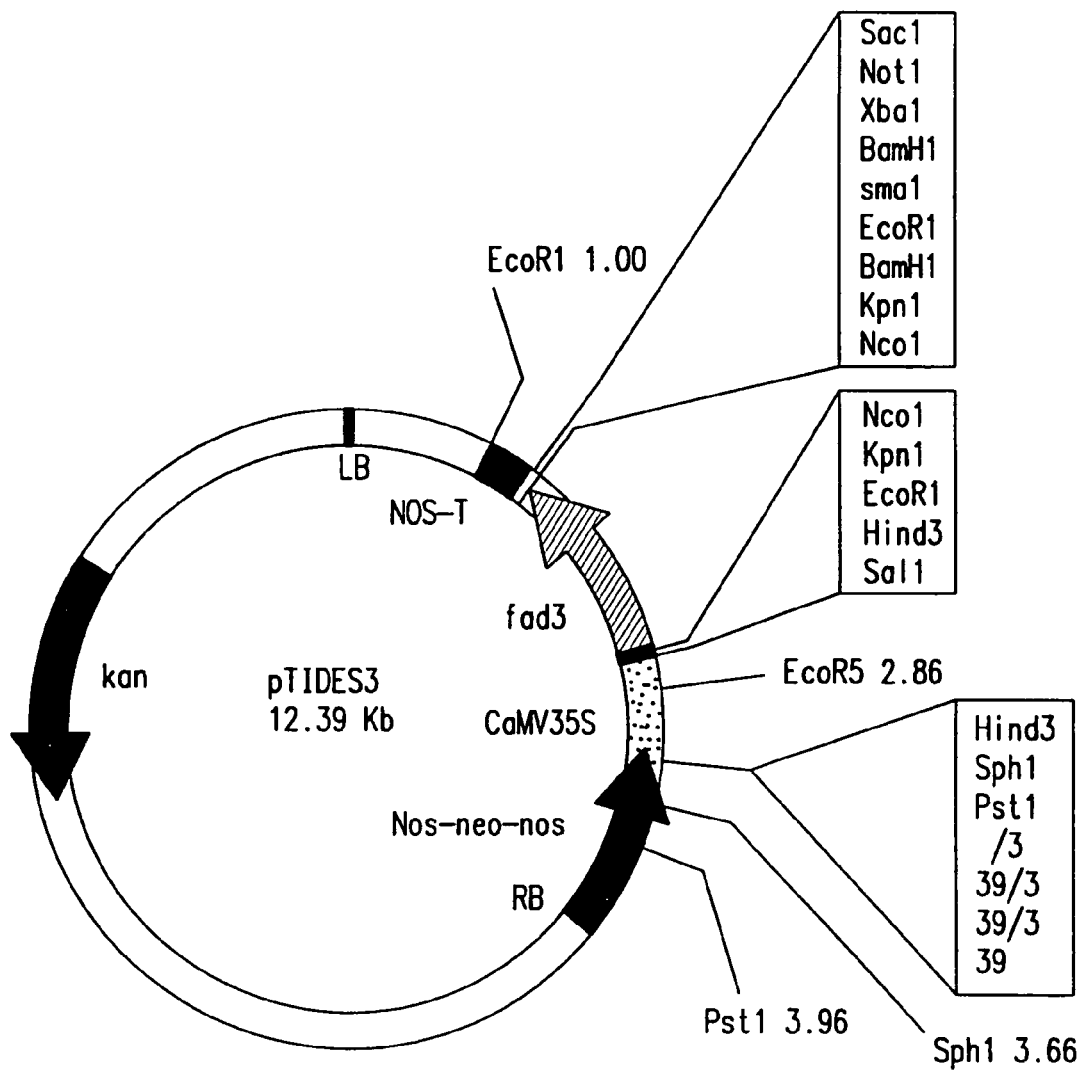
FIG. 6 shows the binary Ti plasmid pTiDES3 which was constructed by insertion of a linoleic acid desaturase cDNA (fad3) into pBI121.

The cDNA was cloned into plant transformation vector pBI121 (FIG. 5) under the control of the CaMV35S promoter to construct pTiDES3 (FIG. 6). Plasmid pTiDES3 was introduced into an *Agrobacterium tumefaciens* strain which also carried an Ri plasmid and this was used to produce transgenic rooty tumors from both wild type *Arabidopsis* and the fad3 mutant. Transgenic tissue was selected for antibiotic resistance to confirm the presence of the pTiDES3. Fatty acid methyl esters were then prepared and examined by gas chromatography to determine the profile of fatty acids being produced in the tissue. The levels of linolenic acid increased, demonstrating that the cDNA on pTiDES3 can complement the fad3 mutation. These results, which are described in detail in Example 1 below, confirm the identity of the cDNA as encoding a linoleic acid desaturase.

The isolation of a plant structural coding sequence provides those skilled in the art with a tool for the manipulation of gene expression by the mechanism of antisense RNA. The technique of antisense RNA is based upon introduction of a chimeric gene which will produce an RNA transcript that is complementary to a target gene (reviewed in Bird and Ray, 1991). The resulting phenotype is a reduction in the gene product from the endogenous gene. The portion of the gene which is sufficient for achieving the antisense effect is variable in that numerous fragments or combinations thereof are likely to be effective. Various portions of the structural coding sequence of linoleic acid desaturase isolated either from cDNA or genomic clones are likely capable of reducing linolenic acid levels in plants by reduction in levels of linoleic acid desaturase levels. An example of using an antisense oriented linoleic acid desaturase structural coding sequence is set out in Example 2.

Polyadenylation Signal

The 3' non-translated region of the double stranded DNA molecule of the present invention contains a region that functions in plant cells to promote polyadenylation to the 3' end of the RNA sequence. Any such regions can be used within the scope of the present invention. Examples of suitable 3' regions are (1) the 3' transcribed, non-translated regions containing the polyadenylated signal of *Agrobacterium* tumor-inducing (Ti) plasmid genes, such as the nopaline synthase (NOS) gene, and (2) 3' regions of plant genes like the soybean storage protein genes and the small subunit of the ribulose-1, 5-bisphosphate carboxylase (ssRUBISCO) gene. An example of a preferred 3' region is that from the NOS gene, described in greater detail in the examples below.

Plant Transformation/Regeneration

Any plant which can be transformed to contain the double-stranded DNA molecule of the present invention are included within the scope of this invention. Preferred plants which can be made to have increased or decreased linolenic acid content by practice of the present invention include, but are not limited to sunflower, safflower, cotton, corn, wheat, rice, peanut, canola/oilseed rape, barley, sorghum, soybean, flax, tomato, almond, cashew and walnut.

A double-stranded DNA molecule of the present invention containing the functional plant linoleic acid desaturase gene can be inserted into the genome of a plant by any suitable method. Suitable plant transformation vectors include those derived from a Ti plasmid of *Agrobacterium tumefaciens*, as well as those disclosed, e.g., by Herrera-Estrella (1983), Bevan (1984), Klee (1985) and EPO publication 120,516 (Schilperoort et al.). In addition to plant transformation vectors derived from the Ti or root-inducing (Ri) plasmids of *Agrobacterium*, alternative methods can be used to insert the DNA constructs of this invention into plant cells. Such methods can involve, for example, the use of liposomes, electroporation, chemicals that increase free DNA uptake, free DNA delivery via microprojectile bombardment, and transformation using bacteria, viruses or pollen.

A plasmid expression vector, suitable for the expression of the linoleic acid desaturase gene in monocots is composed of the following: a promoter that is specific or enhanced for expression in the lipid storage tissues and a 3' polyadenylation sequence such as the nopaline synthase 3' sequence (NOS 3'; Fraley et al., 1983). This expression cassette may be assembled on high copy replicons suitable for the production of large quantities of DNA.

Figure 7:
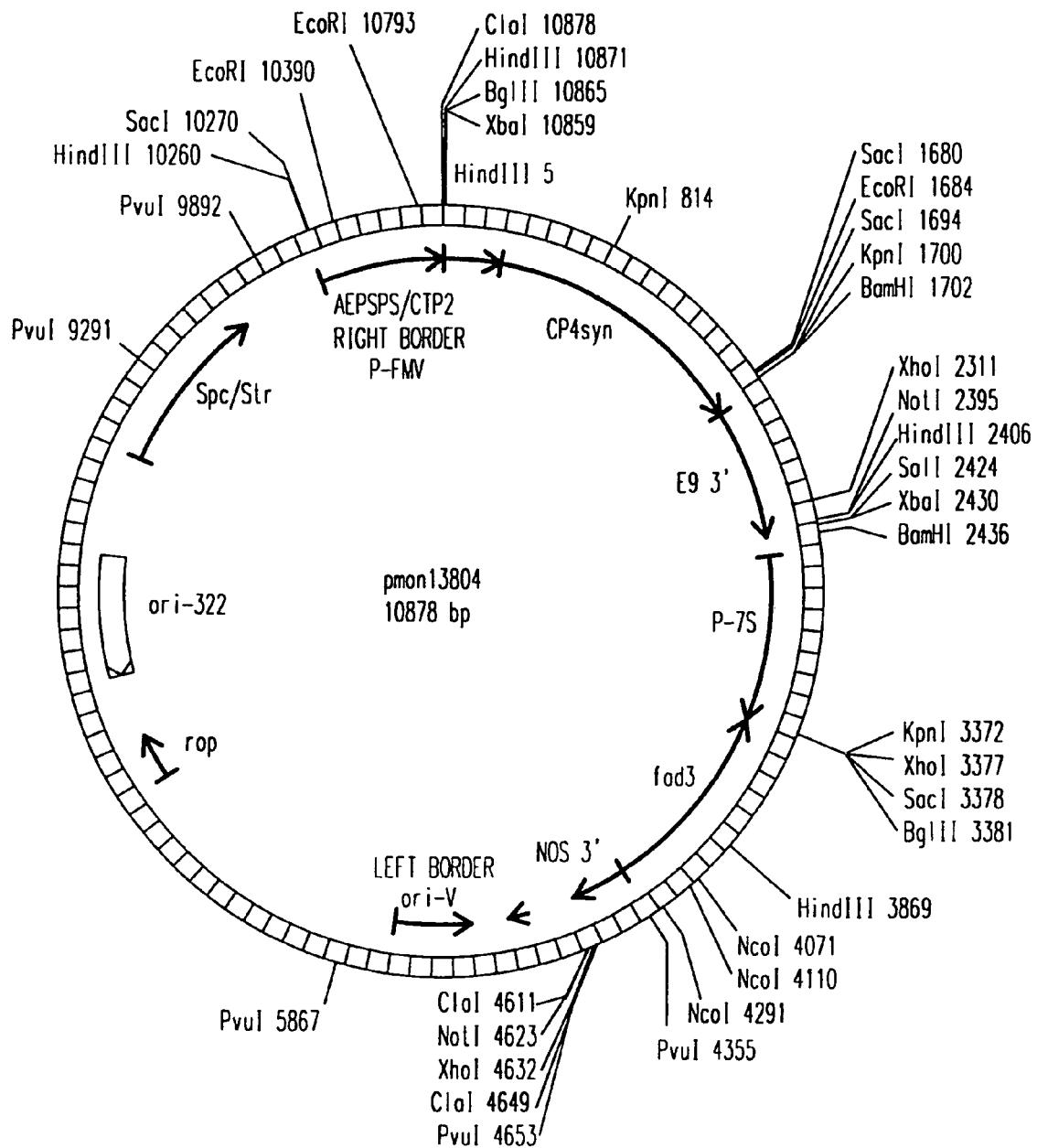
FIG. 7 shows the map of the plant transformation vector pMON13804.

A particularly useful *Agrobacterium*-based plant transformation vector for use in transformation of dicotyledonous plants is plasmid vector pMON530 (Rogers, S. G., 1987). Plasmid pMON530 (see FIG. 7) is a derivative of pMON505 prepared by transferring the 2.3 kb StuI-HindIII fragment of pMON316 (Rogers, S. G., 1987) into pMON526. Plasmid pMON526 is a simple derivative of pMON505 in which the SmaI site is removed by digestion with XmaI, treatment with Klenow polymerase and ligation. Plasmid pMON530 retains all the properties of pMON55 and the CaMV35S-NOS expression cassette and now contains a unique cleavage site for SmaI between the promoter and polyadenylation signal.

Vector pMON505 is a derivative of pMON200 (Rogers, S. G., 1987) in which the Ti plasmid homology region, LIH, has been replaced with a 3.8 kb HindIII to SmaI segment of the mini RK2 plasmid, pTJS75 (Schmidhauser & Helinski, 1985). This segment contains the RK2 origin of replication, oriV, and the origin of transfer, oriT, for conjugation into *Agrobacterium* using the tri-parental mating procedure (Horsch & Klee, 1986). Plasmid pMON505 retains all the important features of pMON200 including the synthetic multi-linker for insertion of desired DNA fragments, the chimeric NOS/NPTII'/NOS gene for kanamycin resistance in plant cells, the spectinomycin/streptomycin resistance determinant for selection in *E. coli* and *A. tumefaciens*, an intact nopaline synthase gene for facile scoring of transformants and inheritance in progeny and a pBR322 origin of replication for ease in making large amounts of the vector in *E. coli*. Plasmid pMON505 contains a single T-DNA border derived from the right end of the pTiT37 nopaline-type T-DNA. Southern analyses have shown that plasmid pMON505 and any DNA that it carries are integrated into the plant genome, that is, the entire plasmid is the T-DNA that is inserted into the plant genome. One end of the integrated DNA is located between the right border sequence and the nopaline synthase gene and the other end is between the border sequence and the pBR322 sequences.

When adequate numbers of cells (or protoplasts) containing the linoleic acid desaturase gene are obtained, the cells (or protoplasts) are regenerated into whole plants. Choice of methodology for the regeneration step is not critical, with suitable protocols being available for hosts from Leguminosae (alfalfa, soybean, clover, etc.), Umbelliferae (carrot, celery, parsnip), Cruciferae (cabbage, radish, rapeseed, etc.), Cucurbitaceae (melons and cucumber), Gramineae (wheat, rice, corn, etc.), Solanaceae (potato, tobacco, tomato, peppers) and various floral crops. See, e.g., Ammirato (1984); Shimamoto, 1989; Fromm, 1990; Vasil and Vasil, 1990.

Uses of Linoleic Acid Desaturase

The present invention can be used for any modification (either increase, decrease, or mere change) of the oil content of a plant or plant tissue. Linolenic acid is an important constituent of several membranes in plant cells.

One preferred method is to modify the oil content of the plant to improve the plant's temperature sensitivity. For instance, plants deficient in linolenic acid display reduced fitness at low temperature (Hugly and Somerville, 1992). Also, increased linoleic acid content in vegetative tissues has been implicated as a factor in freezing tolerance in higher plants (Steponkus et al., 1990 and references therein). In a preferred embodiment, expression of the linoleic acid desaturase structural coding sequence can result in the genetic modification of higher plants to achieve tolerance to low environmental temperatures. Transformation with pTiDES3 demonstrates that linolenic acid levels can be increased by expression of this gene in a constitutive manner. Chilling or freezing injury in crops may be overcome by expression of this gene in vegetative or reproductive tissues by employing an appropriate promoter.

Linolenic acid, a polyunsaturated fatty acid, is also extensively used in the paint and varnish industry in view of its rapid oxidation. Flax seed is a predominant source of this oil. Higher quantities of this fatty acid in rapeseed or soybean will provide opportunities for using vegetable oils from these sources as a replacement for linseed (flax) oil. Expression of a linoleic acid desaturase structural coding sequence in seed tissue can result in a higher proportion of linolenic acid in the storage oil.

Linolenic acid is further a precursor in the biosynthesis of jasmonic acid, an important plant growth regulator. Linolenic acid is converted to jasmonic acid by introduction of an oxygen to the carbon chain by a lipoxygenase, followed by dehydration, reduction, and several β-oxidations (Vick and Zimmerman, 1984). The activity of jasmonic acid has been measured in terms of induction of pathogen defense responses. By application of free linolenic acid to plants, plant pathogen defenses can also be induced (Farmer and Ryan, 1992). A model has been proposed to explain the ability of free linolenic acid to exhibit the effects associated with jasmonic acid (Farmer and Ryan, 1992). It is hypothesized that all of the enzymatic activities which are required for the conversion of linolenic acid to jasmonic acid are constitutively present in the cell and the rate limiting step in the production of jasmonic acid is the availability of free linolenic acid. A likely route for the production of the free linolenic acid is by the activity of a lipase in the plasma membrane.

It further has been observed that exogenous jasmonic acid can more powerfully activate defense responses than can wounding. This suggests that wounds cannot generate enough free linolenic acid to support high level production of jasmonic acid. The activity of the lipase or the availability of appropriate substrate for the lipase may be rate limiting upon wounding. By increasing levels of available substrate, increasing linolenic acid levels in the plasma membrane, it should be possible to enhance a plant's ability to respond to pathogens by allowing for a higher production of jasmonic acid. Expression of a linoleic acid desaturase structural coding sequence can result in a higher molar percent linolenic acid in the plasma membrane of a plant cell therefore enhancing the jasmonic acid signaling pathway. It is our intent to evaluate plants containing high linolenic acid levels in root and foliar tissues for their pathogen resistance.

It is also undesirable to have significant levels of linolenic acid in cooking oils. Linolenic acid is unstable during cooking and is rapidly oxidized. The oxidized products impart rancidity to the finished product. Rapeseed or soybean oil containing less than about 3%, and preferably 2% or less of linolenic acid is ideal for use as a cooking oil. By expression of the antisense of the structural coding sequence for linoleic acid desaturase, it is possible to reduce the linolenic acid content of these oils.

All higher plants have linolenic acid and, therefore, contain genes for linoleic acid desaturases. Because of the many examples in which genes isolated from one plant species have been used to isolate the homologous genes from other plant species, it is apparent to any one skilled in the art, that the results presented here do not only pertain to the use of the B. napus fad3 gene, or to the use of the gene to modify fatty acid composition in B. napus. Obviously, the linoleic acid desaturases from many organisms could be used to increase linolenic acid biosynthesis and accumulation in plants and enzymes from any other higher plant or algae can serve as sources for linoleic acid desaturase genes. For example, since a YAC containing the Arabidopsis gene was used to isolate the B. napus gene, it is apparent that the insert in pBNDES3 could be used as a probe of genomic libraries for isolation of the corresponding full length genes from other plant species. It is also likely that the information contained in the sequence of this gene will be useful to clone other lipid desaturases genes.

Expression of a linoleic acid desaturase in a sense orientation may also allow for the isolation of plants with reduced levels of linolenic acid. This could be accomplished by the mechanism of co-suppression (Bird and Ray, 1991). The molecular mechanism of co-suppression is at this time poorly understood but occurs when plants are transformed with a gene that is identical or highly homologous to an allele found in the plants genome. There are several examples where expression of a chimeric gene in plants can result in a reduction of the gene product from both the chimeric gene and the endogenous gene(s). Those skilled in the art will recognize that the resulting decrease in linolenic acid would be a direct result of expression of the linoleic acid desaturase structural coding sequence and would be correlated to the linoleic acid desaturase activity in the transformed plant.

Linolenic acid levels in plant cells can also be modified by isolating genes encoding transcription factors which interact with the upstream regulatory elements of the plant linoleic acid desaturase gene(s). Enhanced expression of these transcription factors in plant cells can effect the expression of the linoleic acid desaturase gene. Under these conditions, the increased or decreased linolenic acid content would also be caused by a corresponding increase or decrease in the activity of the linoleic acid desaturase enzyme although the mechanism is different. Methods for the isolation of transcription factors have been described (Katagiri, 1989).

The following examples are provided to better elucidate the practice of the present invention and should not be interpreted in any way to limit the scope of the present invention. Those skilled in the art will recognize that various modifications, truncations, etc. can be made to the methods and genes described herein while not departing from the spirit and scope of the present invention.

EXAMPLE 1

Expression of fad3 Gene to Increase Linolenic Acid

To verify the assumption that the cDNA insert in pBNDES3 encodes a linoleic acid desaturase, both wild type and fad3 mutation *Arabidopsis* were transformed to contain the cDNA insert. In order to express the linoleic acid desaturase structural coding sequence (hereafter referred to as the "fad3 gene") in plant cells, the plasmid pBNDES3 was digested with XhoI and the ends were filled in with the Klenow fragment of DNA polymerase (Sambrook et al 1989). The cDNA insert was subsequently excised by digestion with Sac1 and ligated into the Sac1 and Sma1 sites of the binary Ti plasmid vector pBI121 (Clontech Laboratories), thereby replacing the GUS reading frame. The ligation reaction was carried out in 20 µl for 12 h at 16° C. using 100 ng of both insert and vector, and one unit of T4 DNA ligase. The ligation mixture was used to transform competent DH5α *E. coli* cells (prepared by the calcium chloride method, according to Sambrook et al, 1989), and transformants were selected on L-broth plates that contained 50 µg/µl Kanamycin. Alkaline minipreparations of recombinant clones were analyzed for the correct restriction pattern. One of these plasmids, designated pTiDES3, was used for further experiments.

This plasmid was electroporated (according to Mersereau and Pazour, 1990) into *Agrobacterium tumefaciens* strain R1000 which carries an Ri plasmid. The transformed bacteria were selected on kanamycin LB plates for 2 days at 30° C. DNA minipreparations of several recombinant bacteria were performed and analyzed as described above to verify the presence of the construct.

Young flowering stems of wild type and the fad3 mutant of *Arabidopsis* were sterilized for 30 min in 10% commercial bleach, 0.02% Triton X100, and 2-cm explants that contained the flowering stem were infected with R1000 (pTiDES3) This was performed by dipping the sectioned extremity in a drop of an overnight culture of the appropriate *Agrobacterium* that was grown from a single colony in LB medium supplemented with 50 ug/ml Kanamycin.

The infected stems were cultured for two days on solid MSO medium (Gibco MS salts plus Gamborg B5 vitamins, 3% sucrose and 0.8% agar). At this time the stem segments were transferred for 5 weeks to MSO medium containing 200 µg/ml cefotaxime to kill the bacterium. After approximately two weeks, most of the stem explants had developed rooty tumors resulting from transfer of parts of the Ri plasmid into cells of the stem explants. In order to identify the rooty tumors which had also received the binary Ti plasmid pTiDES3, approximately 24 rooty tumors from each treatment were transferred to MSO medium containing 50 µg/ml of kanamycin to select for the growth of those roots which had been cotransformed with the binary Ti plasmid; the medium contained also 200 µg/ml of cefotaxime to inhibit bacterial growth. Following a further period of growth for 2 weeks, fatty acid methyl esters were prepared (as described above) from the roots for analysis by gas chromatography. The results of these analyses are presented in Table 2.

TABLE 2

| | Genotype | | | |
|---|---|---|---|---|
| mol % Fatty acid | wildtype pBI121 | fad 3 pBI121 | wildtype pTiDES3 | fad3 pTiDES3 |
| 16:0 | 22.0 ± 2.9 | 21.2 ± 1.6 | 21.1 ± 0.9 | 21.3 ± 2.3 |
| 16:1 | 2.5 ± 0.7 | 1.6 ± 0.8 | 2.0 ± 0.1 | 1.5 ± 0.2 |
| 18:0 | 2.3 ± 1.9 | 2.3 ± 1.9 | 1.9 ± 0.2 | 1.6 ± 0.4 |
| 18:1 | 3.8 ± 1.3 | 5.9 ± 2.6 | 7.7 ± 2.0 | 9.1 ± 2.0 |
| 18:2 | 37.3 ± 3.7 | 62.2 ± 5.9 | 15.7 ± 11.7 | 24.4 ± 14.9 |
| 18:3 | 31.9 ± 4.5 | 6.7 ± 0.7 | 51.3 ± 10.9 | 42.1 ± 15.5 |

Table 2 shows the fatty acid composition of transgenic roots. The transgenic roots resulting from infection of wild type or the fad3 mutant with *A. tumefaciens* R1000 carrying the vector (pBI121) or the plasmid pTiDES3 were grown in the presence of kanamycin (50 g/ml) for three weeks to identify the roots which had been cotransformed with one of these plasmids. The fatty acid composition of the roots was determined as previously described (Browse et al., 1986). The abbreviations used in Table 2 are as follows: 16:0, palmitic acid; 16:1, palmitoleic acid; 18:0, stearic acid; 18:1, oleic acid; 18:2, linoleic acid; 18:3, linolenic acid. The values presented are the mean ±SD (n=12).

From these results it can be seen that the production of rooty tumors containing pBI121 on wild type *Arabidopsis* or the fad3 mutant had no effect on the fatty acid composition over non-pBI121 containing wild type *Arabidopsis* or fad3 mutant. By contrast, transformation of the fad3 mutant with the plasmid pTiDES3 resulted in large increases in the content of linolenic acid. In contrast to the linolenic acid content of 6.7+/−0.7% in the fad3 mutant transformed with pBI121, the presence of pTiDES3 resulted in accumulation of 42.1% of the fatty acids as linolenic acid. The increased content of linolenic acid was accompanied by a decrease of corresponding magnitude in the content of linoleic acid. Thus, it is clear that the fad3 gene encodes a linoleic acid desaturase. Introduction of the fad3 gene into wild type tissues also resulted in significantly increased accumulation of linolenic acid and a corresponding decrease in linoleic acid (Table 2). Thus, it is apparent from these results that the linoleic acid content of plant tissues can be increased by high level expression of a linoleic acid desaturase. In the present embodiment, the fad3 gene was placed under transcriptional control of the constitutive high level CaMV 35S promoter carried on pBI121. The implication from these results is that expression from this promoter raised the level of expression of the fad3 gene to levels higher than are normally achieved by expression from the endogenous fad3 promoter. The results presented here indicate that the fad3 gene has significant utility in genetic modification of higher plants to elevate linolenic acid levels.

EXAMPLE 2

Antisense Expression of Fad3 Gene to Decrease Linolenic Acid Levels

In order to decrease the linoleic acid desaturase activity by genetic engineering methodology, the cDNA insert of pBNDES3 was cloned into plant expression cassettes in an antisense orientation. A 959 bp BglII restriction fragment of pBNDES3 was used in the antisense expression vectors. The fragment is from 152 nucleotides downstream of the initiating methionine codon of the cDNA to a second BglII restriction site that is located near the C-terminus of the coding region. 189 nucleotides of the coding region are excluded from this fragment. Triple ligations were performed with the fad3 gene fragment to construct two separate plant expression cassettes.

A seed specific expression cassette was constructed by insertion of the BglII fragment of pBNDES3 in an antisense orientation behind the soybean promoter for the α' subunit of β-conglycinin (7S promoter). A 975 bp HindIII to BglII fragment containing the 7S promoter derived from pMON529 was prepared by digesting with BglII for 30 min at 37° C. followed by addition of Calf Intestinal Alkaline Phosphatase (CIAP) (Boehringer Mannheim). The reaction was allowed to proceed for 20 min followed by purification of the linearized DNA using the GeneClean (Bio 101) purification system. The DNA was then digested with HindIII. A fragment derived from pMON999 containing the Nopaline synthase 3' region and the pUC vector backbone was prepared by digestion with BamHI and treatment with CIAP. The DNA was purified by the GeneClean procedure and digested with HindIII. The fragment of pBNDES3 was prepared by digestion with BglII. The three fragments were purified by agarose gel electrophoresis and the GeneClean procedure. 50 to 200 ng of the purified fragments were ligated for one hour at room temperature followed by transformation into the *E. coli* strain JM101. Resulting transformant colonies were used for plasmid preparation and restriction digestion analysis. Double digestion with BglII and NcoI was used to screen for transformants containing the fad3 gene in an antisense orientation. One clone was designated as correct and named pMON13801.

A second expression cassette was constructed to allow for constitutive expression of the antisense message in plants. A fragment containing the enhanced 35S promoter was prepared from pMON999 by restriction digestion with HindIII and BglII followed by treatment with CIAP as above. The correct sized fragment was obtained by agarose gel electrophoresis and the GeneClean procedure. The BglII to HindIII vector fragment and the BglII fragment of pBNDES3 which were purified above were used in this construction. Ligation, transformation and screening of clones were as described above. One clone was designated as correct and named pMON13802.

Figure 8:
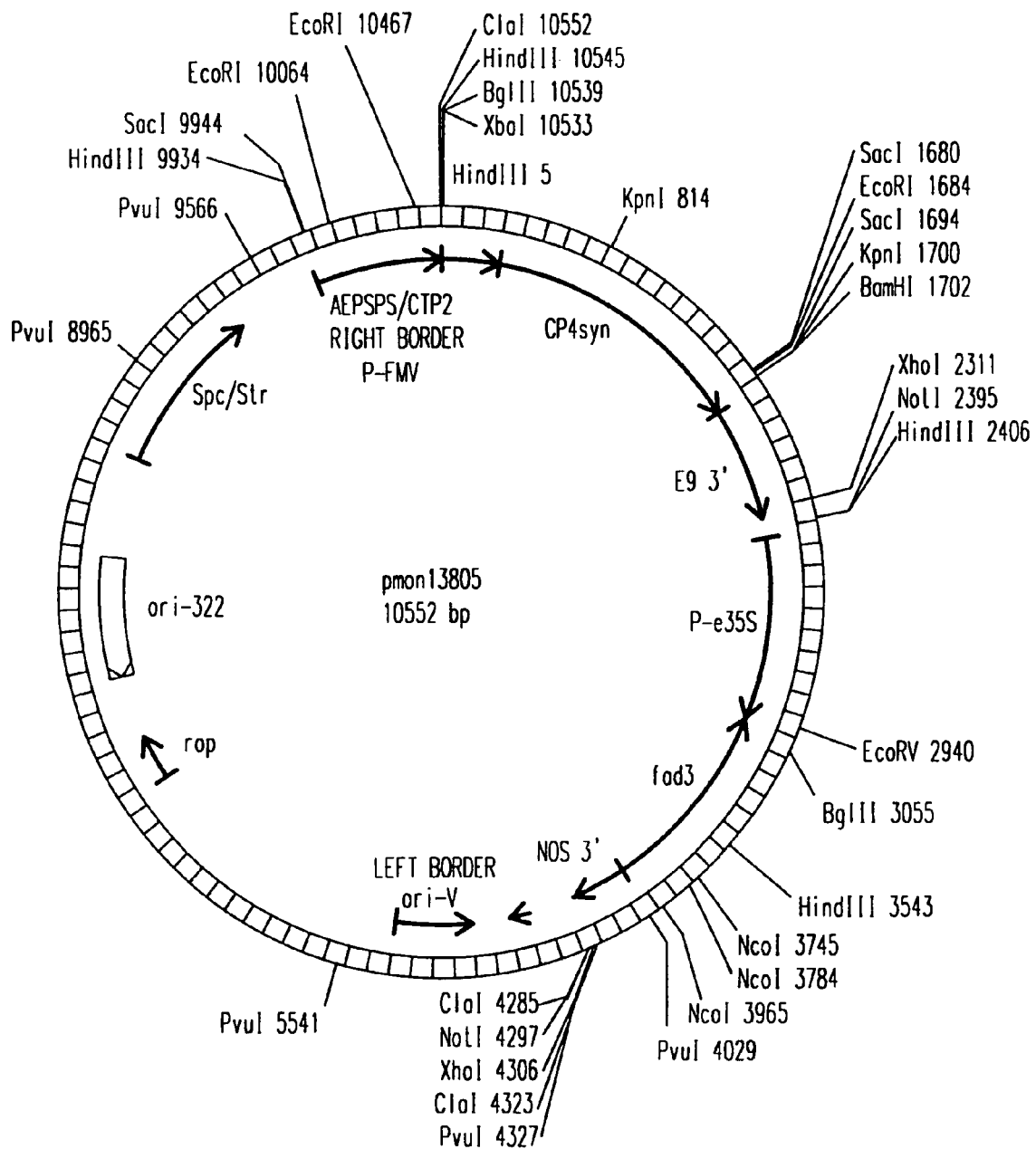
FIG. 8 shows the map of the plant transformation vector pMON13805.

In both pMON13801 and pMON13802, the promoter, fad3 gene and the Nos 3' region can be isolated on a NotI restriction fragment. These fragments can then be inserted into a unique NotI site of the vector pMON17227 to construct glyphosate selectable plant transformation vectors. The vector DNA is prepared by digestion with NotI followed by treatment with CIAP. The fad3 containing fragments are prepared by digestion with NotI, agarose gel electrophoresis and purification with GeneClean. Ligations are performed with approximately 10 ng of vector and 200 ng of insert DNA for 1.5 hours at room temperature. Following transformation into the *E. coli* strain LE392, transformants were screen by restriction digestion to identify clones containing the fad3 expression cassettes. Clones in which transcription from the fad3 cassette is in the same direction as transcription from the selectable marker were designated as correct and named pMON13804 (FMV/CP4/E9, 7S/anti fad3/NOS) (FIG. 8) and pMON13805 (FMV/CP4/E9, E35S/anti fad3/NOS) (FIG. 9).

In preparation for transforming canola cells, pMON13804 and pMON13805 were mated into *Agrobacterium* ABI by a triparental mating with the helper plasmid pRK2013.

Seeds from the plants produced by transformation were analyzed for alterations in fatty acid profile. Fatty acid methyl esters (FAMES) were prepared from seed tissue and analyzed by capillary gas chromatography (Browse et al, 1986). For initial screening of plants, six seeds were pooled together from an individual plant. The seeds were crushed and FAMES extracts were made. Control plants, plants transformed with the selectable marker only (pMON17227), were also analyzed using the identical procedure. From the initial screen on pooled seed samples, several lines were identified which displayed a decreased level of linolenic acid. Lines with decreased levels of linolenic acid were reanalyzed by determining fatty acid profiles from individual seeds. Four to twenty individual seed were analyzed from candidate lines and from selected control plants. The results of the FAMES analysis is summarized in FIG. 9.

Figure 9A:
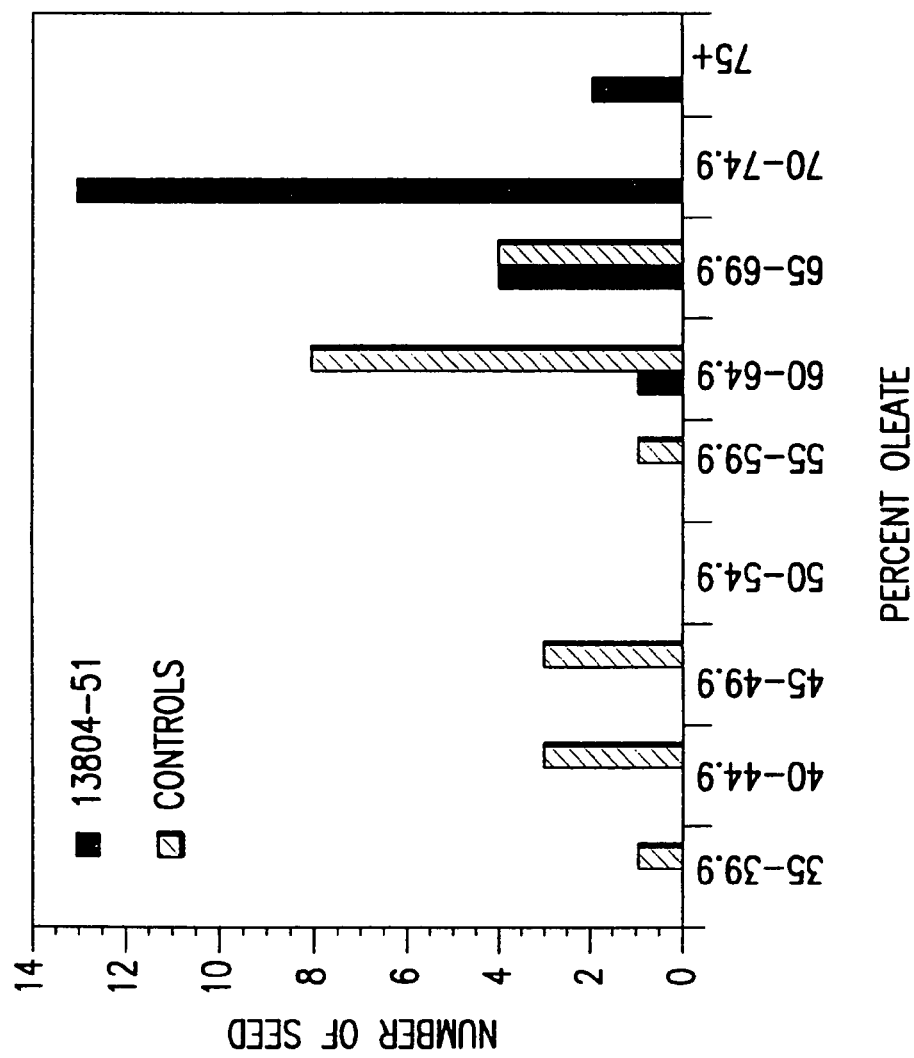
FIG. 9 shows the oil content of control and transformed canola seed in accordance with the present invention.
Figure 9B:
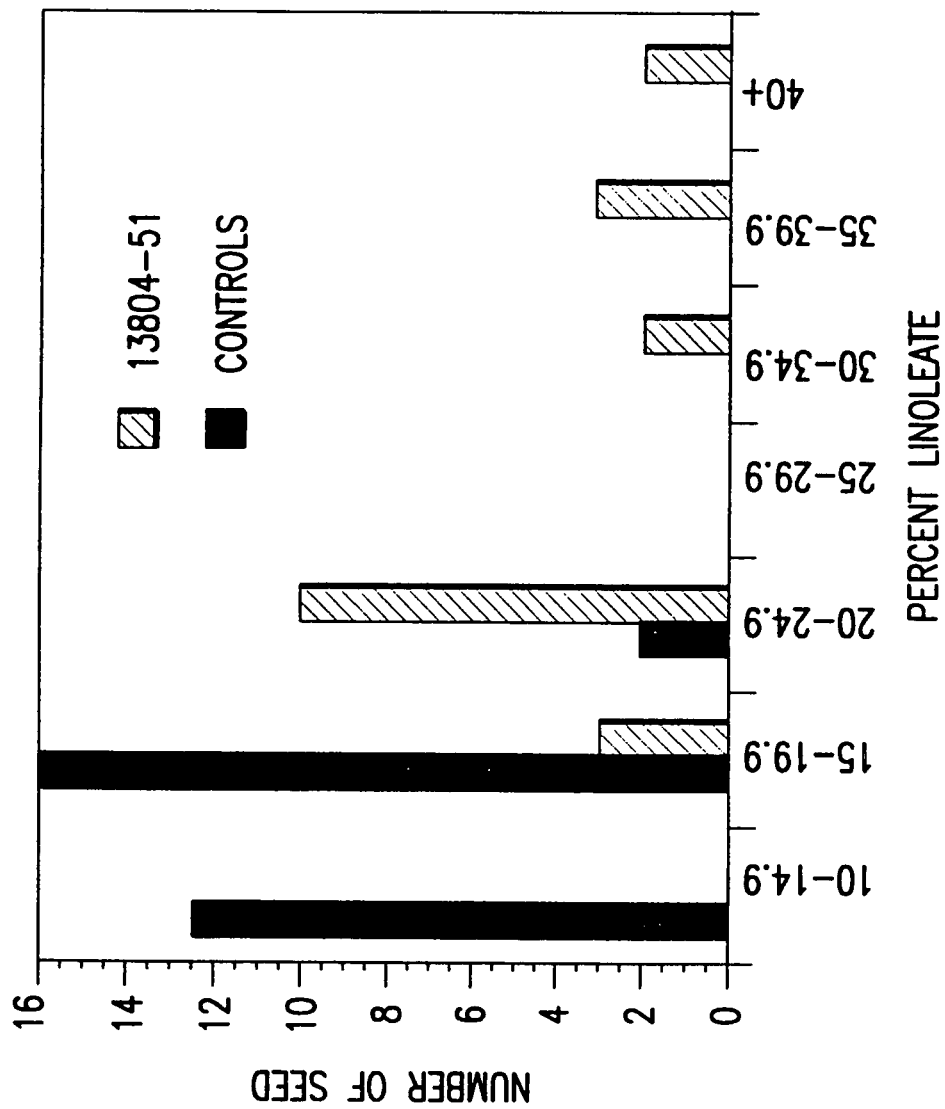
Figure 9C:
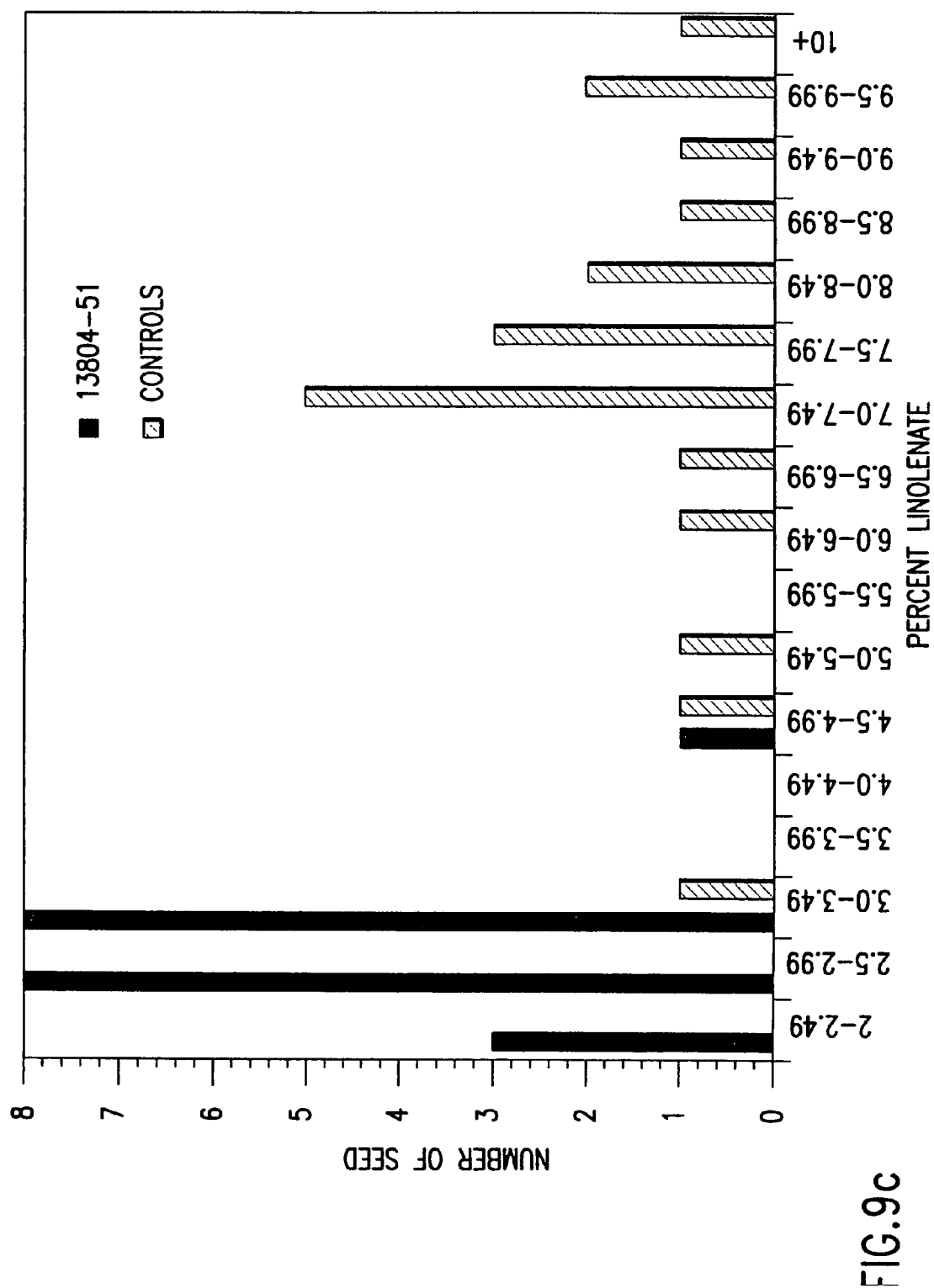

FIG. 9 shows the levels of fatty acids expressed in molar percent of twenty individual seed of the transgenic line 13804-51 as compared to control seed. Panel A discloses oleic acid, panel B discloses linoleic acid and panel C discloses linolenic acid.

The data in FIG. 9 demonstrate that antisense expression of a linoleic acid desaturase has significantly altered the fatty acid profile of the resulting seed tissue. The percent of linolenic acid has been reduced to a little over 2% of the total fatty acid in the seed tissue. The percent of linoleic acid has been reduced slightly and surprisingly, the percent of oleic acid in the seed has been increased to approximately 70%. This demonstrates the applicability of utilizing the fad3 gene to manipulate the fatty acid profile of crop plants.

In order to demonstrate that the alteration in the fatty acid profile of the FAMES extracted from total seed tissue would be reflected in the seed oil fraction, triglycerides from seeds of fad3 antisense plants were characterized. Total lipid extracts were made by pooling ten seeds and grinding in 2 ml of methanol:chloroform:water (4:2:1). The homogenate was allowed to stand for 20 min and then debris was pelleted and discarded. To the supernatant 400 µl of chloroform:methanol (2:1), 640 µl of chloroform and 740% of water was added and vortexed. Phases were separated by centrifugation and the chloroform phase was recovered and dried under nitrogen. Samples were resuspended in 100 µl of chloroform and 10 µl was applied to silica gel G thin layer chromatography plates for separation. Two identical plates were prepared with one being charred after development to allow for alignment and location of spots to be analyzed on the other plate. Plates were developed three times in petroleum ether:diethyl ether:acetic acid (90:10:1). One plate was sprayed with 50% sulfuric acid and heated in an oven at 90° C. to allow for detection of lipids. Triglyceride fractions were identified as comigrating on the plate with purchased lipid standards (Sigma Chemical Co, cat #178-13). The charred plate was aligned with the identical plate and the triglyceride fractions were scraped from the plate. The fatty acids were transesterified to produce FAMES extracts for GC analysis by the same procedure as above. The fatty acid profiles of the triglyceride fractions are shown in Table 3 and demonstrate that this fraction have decreased linolenic acid.

TABLE 3

| Transgenic line | Mol % 18:1 | 18:2 | 18:3 |
| --- | --- | --- | --- |
| 17227-10 | 44 | 30 | 15.3 |
| 17227-493 | 65 | 17 | 6.9 |
| 13804-47 | 58 | 21 | 4.3 |
| 13804-50 | 67 | 20 | 2.8 |
| 13804-76 | 59 | 19 | 5.0 |
| 13804-117 | 62 | 21 | 4.0 |

Table 3 compares the fatty acid molar percentages of triglyceride fractions from control and transgenic lines. These above results provide clear evidence that the fad3 gene can be used to decrease the levels of linolenic acid in the storage oil of plants. The gene provides a tool for the manipulation of the fatty acid profile of seed storage oil to improve the products derived from the oil.

A surprising result of this Example 2 is the effect the antisense fad3 gene has on the oleic acid content. The precise mechanism by which antisense expression of a gene exerts an effect on the activity of an endogenous gene is unclear but is obviously a function of the homology of the sense and antisense gene products. Based upon the above experimental result, it would not be unreasonable to predict that the portion of the fad3 gene antisense message used contained a certain degree of homology with the genes providing the activity of one or more oleate desaturases. Therefore, a further advantage of the above invention is that it is possible that expression of a linoleic acid desaturase antisense message may exert an effect on oleate desaturase activity.

The unexpected nature of the reduction in oleic acid desaturase activity from the antisense fad3 plants is most apparent when one compares the fatty acid profiles from the antisense plants and the fad3 mutant of *Arabidopsis*. The levels of linoleic acid in the fad3 mutant plants increased when linoleic acid desaturase activity was eliminated by mutation. This indicates that the activity of the oleate desaturase was not highly effected by the loss of linoleic acid desaturase activity or by the accumulation of linoleic acid. In the fad3 mutant of *Arabidopsis* the level of linoleic acid increased when the level of linolenic acid decreased. However, a different pattern occurred in the antisense fad3 plants. In plants which exhibit a decreased percent of linolenic acid there is no corresponding increase, and is often a decrease, in the percent of linoleic acid. There is an increase in the percent of oleate in the antisense fad3 plants. This would indicate that oleate desaturase activity is depressed in these plants. The effects on the fatty acid profile by the fad3 mutation and the fad3 antisense expression are not equivalent, indicating that antisense expression of a linoleic acid desaturase can depress an oleate desaturase activity in plants.

EXAMPLE 3

Modification of Linolenic Acid Levels in Soybean

The isolation of the fad3 gene from *B. napus* provides a tool to those with ordinary skill in the art to isolate the corresponding gene or cDNA from other plant species. There are many examples in which genes from one plant species have been used to isolate the homologous genes from another plant species. One such plant which could be improved upon by the modification of the level of linolenic acid is soybean.

Soybean oil typically contains linolenic acid at a level of 7-9% of the fatty acid in the oil. This level is undesirable because it promotes instability upon heating and imparts rancidity to the finished product. The levels of linolenic acid can be lowered by the expression of the soybean fad3 gene or cDNA in an antisense orientation in the developing seed. The following example describes one method for the isolation of a fad3 cDNA from soybean. However, similar procedures could be followed to isolate a genomic clone which could also be used to decrease the level of linoleic acid desaturase activity by antisense expression of a portion or all of the gene.

The fad3 gene from *B. napus* is used as a probe to screen a cDNA library constructed from soybean mRNA. In order to isolate a cDNA to be used in decreasing linolenic acid in seed, the optimal tissue to use for the isolation of mRNA is developing seed. There is, however, flexibility in the choice of methods and vectors which can be used in the construction and analysis of cDNA libraries (Sambrook et al, 1989). Procedures for the construction of cDNA libraries are available from manufacturers of cloning materials or from laboratory handbooks such as Sambrook et. al, 1989. Once a suitable cDNA library has been constructed from soybean, all or a portion of the fad3 cDNA from *B. napus* is labeled and used as a probe of the library. DNA fragments can be labeled for radioactive or non-radioactive screening procedures. The library is screened under suitable stringency. Conditions are dependent upon the degree of homology between the fad3 gene of *B. napus* and soybean. Probe positive clones are plaque purified by standard procedures and characterized by restriction enzyme mapping and DNA sequence analysis. Clones are concluded to be soybean fad3 based upon data obtained from the sequence analysis or by expression in plants.

The entire clone or a portion thereof is placed down stream of a promoter sequence in an antisense orientation. Suitable promoters include seed specific promoters, such as the 7S (β-conglycinin) a'-subunit promoter, or less tissue specific promoters, such as the CaMV 35S promoter. An appropriate 3' non-translated region is placed downstream of the antisense cDNA to allow for transcription termination and for the addition of polyadenylated nucleotides to the 3' end of the RNA sequence. This expression cassette is then combined with a selectable or scorable marker gene and soybean cells are transformed by free DNA delivery (Christou et al, 1990) or an *Agrobacterium* based method of plant transformation (Hinchee et al, 1988). Plants recovered are allowed to set seed and mature seed are used for the production of FAMES by the procedures outlined above. The FAMES extracts are analyzed by gas chromatography to identify plant lines with reduced levels of linolenic acid in the seed.

Alternatives to the above methods may include but are not limited to the use of degenerate oligonucleotides as probes to screen the library. Degenerate oligonucleotide probes would be most optimally designed by choosing short segments of the fad3 amino acid sequence where the degeneracy of the genetic code is limited or by choosing sequences which appear to be highly conserved between the fad3 gene of *B. napus* and other known linoleic acid desaturases, such as the desaturase from the cyanobacterium *Synechocystis*. The oligonucleotides could be labeled and used to probe a soybean cDNA library. Alternatively, degenerate oligonucleotides could be used as primers for the isolation of a portion or all of the soybean cDNA by PCR amplification.

Similar procedures could be used to isolate the homologous genes from other plant species. Another preferred plant species which could be improved upon by the modification of the level of linolenic acid is flax. Flax oil typically contains linolenic acid at a level of 45-65% of the fatty acid in the oil. This level is undesirable because it promotes instability upon heating and imparts rancidity to the finished product.

EXAMPLE 4

Sense Expression of Fad3 to Obtain Reduced Levels of Linolenic Acid

The cloning of the fad3 gene also provides a tool to decrease the levels of linolenic acid via the mechanism of co-suppression. The molecular mechanism of co-suppression occurs when plants are transformed with a gene that is identical or highly homologous to an allele found in the plants genome (Bird and Ray, 1991). There are several examples where expression of a chimeric gene in plants can result in a reduction of the gene product from both the chimeric gene and the endogenous gene(s). Therefore the fad3 gene product of *B. napus* may be reduced by transformation of *B. napus* with all or a portion of the fad3 cDNA which has been isolated. The resulting plant has reduced linoleic acid desaturase activity in tissues where the chimeric gene is expressed. The phenotype of reducing the linoleic acid desaturase activity is a reduction in the levels of linolenic acid. The mechanism of co-suppression could be applied to any plant species from which the fad3 gene is cloned and the plant species is transformed with fad3 in a sense orientation.

In order to reduce levels of linolenic acid by the mechanism of co-suppression, a plant transformation construct is assembled with the fad3 gene or cDNA in a sense orientation. The entire clone or a portion thereof is placed downstream of a promoter sequence in a sense orientation. Suitable promoters include seed specific promoters, such as the 7S (β-conglycinin) a'-subunit promoter, or less tissue specific promoters, such as the CaMV 35S promoter. An appropriate 3' non-translated region is placed downstream of the fad3 gene to allow for transcription termination and for the addition of polyadenylated nucleotides to the 3' end of the RNA sequence. This expression cassette is then combined with a selectable marker gene and *B. napus* cells are transformed by an *Agrobacterium* based method of plant transformation. Plants recovered are allowed to set seed and mature seed are used for the production of FAMES which are analyzed by gas chromatography to identify plant lines with reduced levels of linolenic acid in the seed.

EXAMPLE 5

Isolation of a Chloroplast Delta 15 Desaturase from *Arabidopsis*

A fragment of 959 bp was excised from the fad3 cDNA insert using the restriction endonuclease BglII, and labeled radioactively according to Feinberg and Vogelstein (1983). This fragment was used to probe a cDNA library from *Arabidopsis thaliana* as described above (Example 1) except that the hybridization temperature was 52° C. Several cDNA clones were positive, and one of them (pVA1) was further characterized. Its deduced amino acid sequence exhibited a strong homology with fad3 except at the N-terminus. The cDNA insert was placed under the control of the 35S promoter in the Ti vector pBI121, and the resulting construct, pBIVA12 was electroporated into *Agrobacterium* (C58 pGV3101). The bacterium was used to transform the *Arabidopsis* mutant fadD. For transformation, plants were grown at 22° C. with a light intensity of $100/\mu E/cm^{-2}$, until bolting (approximately 2 and ½ weeks). The stems (1 mm-10 mm long) were removed and the plants were inoculated with a drop of an overnight culture of the bacterium. The same operation was repeated 7 days afterwards.

The plants were then allowed to set seeds. The seeds were plated (2500 seeds per 150 mm petri dish) on MSO plates that contained 50 μl/ml kanamycin to select for plants that had integrated the construct. One transformant plant was obtained, and the fatty acids from its leaves were analyzed by gas chromatography (Table 4). The results obtained show that the pBIVA12 construct is able to reestablish the levels of linolenic and hexadecatrienoic acids in the fadD mutant at a level equal to or superior to the wild type. This demonstrates that pVA12 encodes the fadD gene.

TABLE 4

| fatty acid | fadD | WT | FadD pBIVA12 |
|---|---|---|---|
| 16:0 | 13.0 | 14.0 | 14.9 |
| 16:1 | 4.9 | 4.3 | 4.2 |
| 16:2 | 8.7 | 0.5 | 0.3 |
| 16:3 | 3.0 | 13.2 | 9.5 |
| 18:1 | 3.3 | 2.3 | 1.2 |
| 18:2 | 36.4 | 10.9 | 5.8 |
| 18:3 | 30.8 | 54.6 | 63.7 |

Table 4 shows the complementation of the fadD mutant. Fatty acids were extracted from leaves of *Arabidopsis* according to Browse et al (1986) and were quantified (mol %) by gas chromatography. WT stands for the Columbia wild type.

EXAMPLE 6

Isolation of a Second Chloroplast Delta 15 Desaturase from *Arabidopsis*

A fragment of 959 bp was excised from the cDNA insert using the restriction endonuclease BglII, and labelled radioactively according to Feinberg and Vogelstein (1983). This fragment was used to probe a cDNA library from *Arabidopsis*, exactly as described above (Example 5). Among the several positive clones obtained, the cDNA pVA34 was further characterized. Its deduced amino acid sequence exhibited 71.8% and 79.5% homology with fad3 and fadD, respectively. The N-terminus resembled a chloroplast transit peptide, meaning that this protein is likely to be localized to the chloroplast. The strong homology with fad3 and fadD suggests that the protein is also a delta 15 desaturase. Aside from fad3 and fadD, the only locus known to control delta 15 desaturation is the fadE locus, which controls a temperature-induced delta 15 desaturase. Therefore, it is likely that the cDNA contained within the clone pVA34 corresponds to the fadE locus.

EXAMPLE 7

Linoleic Desaturase Homology to Plant Oleic Desaturases

The linoleic desaturase genes are the first plant desaturases isolated whose proteins enzymatically perform the desaturation of an unsaturated fatty acid precursor. The reaction that linoleic desaturase performs and the cofactors it uses are likely to be very similar for the oleic desaturase reaction. Given the similar reactions, similar substrates and probably similar cofactors, it is likely that the oleic desaturase genes and proteins have homology to the linoleic desaturase genes and proteins. That the genes share homology is supported by the finding that antisense expression of the linoleic acid desaturase message results in higher oleic acids levels, which experimentally indicates homology between the linoleic and oleic desaturases. These factors indicate that the linoleic desaturase protein and nucleic acid sequences provide useful information for isolating other lipid desaturase genes, particularly oleic desaturase genes.

a. Identification of Unknown cDNA Sequences in Databases.

Random cDNA sequencing generates a large number of sequenced clones but provides no information about the function of the encoded proteins. Homology to known proteins is the quickest method for identifying the protein function encoded in the sequenced cDNA. However, homology searches are informative only when a homology with a previously characterized protein are found. A cDNA sequence that is not homologous to any known protein remains in the unknown function category. Thus the results functionally identifying the linoleic desaturases by sequence and by their ability to complement mutations in plant desaturase genes now provides a method for identifying the function and identity of random cDNA clones by their homology to the linoleic desaturases. Additionally oleic desaturases are identified by their homology with linoleic desaturases.

A TFASTA search of the GenBank and EMBL public data bases for genes encoding proteins homologous to the protein sequence of the linoleic desaturase fad3 has identified both linoleic desaturases and a second class of plant lipid desaturases likely to be oleic desaturases. In particular, sequences found in GenBank and EMBL and identified as T04093 and T12950 show significant homology to linoleic desaturases but show less homology than other linoleic desaturases. These sequences have 30% homology to fad3 and 56% similarity to fad3 linoleic desaturase (TABLE 5). The full length clone of these cDNAs is obtained by standard methods and is inserted into plant gene expression and transformation vectors and transformed into fad2 *Arabidopsis* mutants to confirm the identity of the oleic desaturase by genetic complementation as was described in the example with linoleic desaturase.

TABLE 5

Comparison of Fad3 and T04093 Protein Sequences

```
Percent Similarity: 52.381%    Percent Identity: 30.476% fad3   101 GHGSFSDIPLLNSVVGHILHSFILVPYHGWRISHRTHHQNHGHVENDESW 150
           |:|||:||||  :|:.|||  ||  |  | :|.|| :
T04093   1 ..............LIFHSFLLVPYFSWKYSHRRHHSNTGSLERDEVF   34

151 VPLPEKLYKNLP.....HSTRMLRYTVPLPMLAYPIYLWYRSPGKEGSHF 195
           ||  ...  |  ..    .|::..||.: :|::|:||  :. .|:   .:
        35 VPKQKSAIKWYGKYLNNPLGRIMMLTVQF.VLGWPLYLAFNVSGR...PY  80

196 NPYSSLFAPSERKLIATSTTCWSIMLATLVYLSFLVDPVTVLKVYGVPYI 245
           :.:.:  |  |...   .   . :.  ::  .:
        81 DGFACHFFPNAPIYNDRERSRYTSLMRVF*....................110
``` b. Isolation of a Oleic Desaturase cDNA.

The protein sequence of plant linoleic desaturases can be used to isolate oleic desaturases. The conserved regions between the linoleic desaturases and the DesA oleic desaturase are functionally important and are conserved in the plant oleic desaturase proteins as well. These conserved amino acid sequences provide a method of isolating plant oleic desaturases. There are several regions of the linoleic desaturase fad3 that are conserved in fadD, fadE and DesA. The consensus amino acid sequence is shown in Table 6, with the amino acids identical in all four proteins shown in capital letters. As described below, oligonucleotides designed to encode the amino acids sequences in the conserved regions are used to identify and isolate plant oleic desaturases.

TABLE 6

Fad3 Protein Sequence and Peptide Targets

```
MVVAMDQRSNVNGDSGARKEEGFDPSAQPPFKIGDIRAAIPKHCWVKSPLRSMSYVTRD
v.tplttp ...spseed..erfdpgapppf.laDIraaiPKhcwvKnpwksmsyVvrd
                                    DIraaiPKhCwvK
                           (1a) DIraaiP
                                (1b) aiPKhC
                                     (1c) KhCwvK
```

TABLE 6-continued

Fad3 Protein Sequence and Peptide Targets

```
IFAVAALAMAAVYFDSWFLWPLYWVAQGTLFWAIFVLGHDCGHGSFSDIPLLNSVVGHIL
va.vfalaa.aayfnnW.lwPlyW.aqGTmfwalFVlGHDCGHgSFsndp.lNsvvGH.l
             WflwPlyWvaqGT        FVlGHDCGHqSF
        (2a) WflwPlyW        (3a) FVlGHD
        (2b) WflwP            (3b) VlGHDC
          (2c) wPlyW            (3c) GHDCGH
             (2d) WvaqGT           (3d) CGHgSF HSFILVPYHGWRISHRTHHQNHGHVENDESWVPLPEKLYKNLPHSTRMLRYTVPLPMLAY
hssilvPyHgWRisHrtHHqnhghvEnDesWhpl.ekiyknlpk.trmfrftlplpmlay
        PyHgWRisHrtHH       EnDesWvP
    (4a) PyHgW           (5a) EnDesW
      (4b) HgWRisH         (5b) DesWvP
        (4c) WRisHrtHH
        (4d) WRisH
           (4e) HrtHH PIYLWYRSPGKEGSHFNPYSSLFAPSERKLIATSTTCWSIMLAT.LVYLSFLVDPVTVLK
pfylw.rspgk.gShyhpds.lF.pkerkdvltStacwtamaAl.lvcLnft.gpiqmlK VYGVPYIIFVMWLDAVTYLHHHGHDEKLPWYRGKEWSYLRGGL.TTIDRDYG.IFNNIH
lygiPywifvmWldfvTylHHhghedklpwyrgkeWSylrggL.tTldrDYg.winnih
            WldavTylHH             WSylrggL.tTidrDY
       (6a) WldavT          (7a) WSylrggL
           (6b) TylHH              (7b) L tTidrD
                                     (7c) TidrDY HDIGTHVIHHLFPQIPHYHLVDATRAAKHVLGRYYREPKTSGAIPIHLVESLVASIK
    HDIgtHviHHLfpqIPhYhLveAteaaKpvlGkyyrEpk.sgplplhLlesl.ksik
    HDIgtHviHHLfpqIPhY
(8a) HDIgtH
    (8b) HviHHL
       (8c) HHLfpqI
          (8d) HLfpqIP
            (8e) LfpqIPhY KDHYVSDTGDIVFYETDPDLYVYASDKSKIN*
.dhyvsdtGdvvyYeadp.lyg..s*
``` c. Isolation of the fadC (Fad6) Gene from *Arabidopsis thaliana*

The fadC gene (also referred to as fad6) encodes a chloroplastic omega-6 desaturase.

The deduced amino acid sequences of the fad3 gene from *Brassica napus* and the fadD and fadE genes from *Arabidopsis thaliana* were compared with the DesA gene from *Synechocystis* (*Nature*, 347:200, 1990). The sequence GHDCGH was determined to represent the most highly conserved region of these proteins. Consequently, a degenerate oligomer was designed that contains all the possible condons for the sequence GHDCGH. This oligomer has the following sequence: GGNCAYGAYTGYGGNCA.

An *Arabidopsis thaliana* cDNA phage library obtained from the laboratory of Dr. Ron Davis (*PNAS*, 88: 1731-1735) was used to screen for desaturase genes. This library was made using material from all above ground plant parts.

Approximately 120,000 phage from the library were plated onto three plates and hybondN+ was then used to prepare three filters from each plate (*Molecular Cloning—A Laboratory Manual,* 2nd Edition. Eds. J. Sambrook, E. F. Fritsch, and T. Maniatis, Cold Spring Harbor Laboratory Press, Cold Spring Harbor, N.Y. 1989, hereafter "Sambrook"). Two filters from each plate were probed using the degenerate consensus oligomer which had been end-labelled with (32)P using T4 polynucleotide kinase. The hybridizations were performed in a solution that contained high amounts of tetramethylammonium chloride in order to minimize differences in the melting temperatures of the oligomers that together comprise the degenerate consensus oligomer. The hybridization solution had the following composition: 3 M tetramethylammonium chloride, 10 mM sodium phosphate pH 6.8, 1.25 mM EDTA, 0.5% SDS, 0.5% milk. Hybridization was carried out overnight at a temperature of 44° C. Filters were then washed four times, 20 minutes each time, with 6×SSC+0.15% SDS at room temperature. Filters were then washed one time, for 30 minutes, with 4×SSC+0.1% SDS at room temperature. The filters were then exposed to film for two days.

The third set of filters that were made from each phage-containing plate were probed using DNA sequences from the three *Arabidopsis* desaturase genes that had already been identified: fad3, fadD and fadE. The fad3, fadD and fadE genes were labelled with (32)P and hybridized to the third set of phage filters in the following hybridization solution: 0.2 M NaCl, 20 mM sodium phosphate pH 7.7, 2 mM EDTA, 1% SDS, 0.5% milk, 10% dextran sulfate, 0.1% sodium pyrophosphate. Hybridization was carried out overnight at 65° C. Filters were washed four times, 30 minutes per time, in 2×SSC+0.15% SD at room temperature and then for 45 minutes with 1×SSC+0.1% SDS at 65° C. The filters were then exposed to film for approximately two hours.

The two sets of filters that were probed with the degenerate consensus oligomer showed about 60 positive phage per plate (or about 180 total positive phage). Results from the third set of filters that were probed with the fad3, fadD and fadE genes indicated that only a small percentage of the phage that hybridized to the consensus of oligomer contained the fad3, fadD or fade genes.

Seventy-six of the phage that hybridized to the consensus oligomer, but not to the fad3, fadD or fadE genes, were plaque purified. The purified phage were then spotted onto bacteria growing on solid media on plates and allowed to form plaques. Several duplicate filters were then made of these plates (Sambrook). One of these filters was probed with the consensus oligomer, as described above. A second filter was probed with a mixture of the *Arabidopsis thaliana* fad3, fadD and fadE genes, as described above.

In order to determine which of the 76 phage contained the same cDNA inserts as which other phage, some of the filters were probed with cDNA inserts from some of the phage. In order to perform this experiment, the cDNA inserts from most of the phage were isolated by using oligomers that bound to DNA flanking the cDNA cloning site in the phage vector to isolate the cDNA sequences using the polymerase chain reaction (PCR). These cDNA sequences were labelled with (32)P (random hexamer labelling) and hybridized to the filters using the following hybridization solution: 30% formamide, 0.2M NaCl, 20 mM sodium phosphate pH 7.7, 2 mM EDTA, 1% SDS, 0.5% milk, 0.1% sodium pyrophosphate. The hybridizations were carried out for 14 hours at 65° C. The filters were washed four times 15 minutes per wash, with 2×SSC+0.15% SDS at room temperature and were then exposed to film.

The combination of the high formamide concentration in the hybridization solution and the high hybridization temperature meant that only DNA sequences that were virtually identical would hybridize, allowing us to distinguish between nearly identical sequences. Several rounds of hybridizations using cDNA inserts from different phage were carried out until it had been determined which phage contained the same, or at least extremely similar, cDNA inserts. On the basis of these experiments, we determined that all of the 76 phage contained one of four cDNA inserts. Sequence data was obtained from each of these four cDNAs. None of these cDNAs was found to be homologous to known desaturase genes, and so we feel that none of these four cDNAs is likely to encode a desaturase.

Since the number of phage that hybridized to the consensus oligomer was quite high (about 180 phage hybridized in the initial screen described above), we were not able to analyze all of the positive phage in the initial experiments. So, an attempt was made to identify phage that hybridized to the consensus oligomer but that did not contain the fad3, fadD of fadE genes or one of the four non-desaturase encoding clones that were identified in the first screen. In order to do this, between 500,000 and 1,000,000 phage from the library described above were plated onto 10 plates. Three filters were made from each plate (Sambrook). Two of these three sets of filters were then hybridized with (32) P labelled consensus oligomer as described above except that hybridization was carried out at 42° C. instead of at 44° C. The third set of filters were hybridized with (32)P labelled DNA from the *Arabidopsis* fad3, fadD and fadE genes together with DNA from each of the four cDNA's identified in the first round of screening as hybridizing to the consensus oligomer but not encoding desaturases. This third set of filters were hybridized in: 30% formamide, 0.2 M NaCl, 20 mM sodium phosphate pH 7.7, 2 mM EDTA, 1% SDA, 0.5% milk, 0.1% sodium pyrophosphate at 65° C. All three sets of filters were hybridized for 12 hours and then washed several times with 2×SSC+0.15% SDS at room temperature. The filters were then exposed to film.

Approximately 200 phage from each plate hybridized to the consensus oligomer. 50-60% of these phage also hybridized to fad3, fadD, fadE or to one of the four clones identified in the first screen. About 58 phage that hybridized to the consensus oligomer, but not to fad3, fadD, fadE or one of the four previously identified clones, were plaque purified. The purified phage were then spotted onto a bacterial lawn growing on solid media on a petri plate and the phage were allowed to form plaques. Several filters were prepared from these plates and hybridized with (32)P labelled cDNA inserts from various of the newly purified phage, as described above. In this manner, all of the phage identified in this second round of screening were found to contain one of eight different cDNA inserts.

Sequence data was obtained from each of the eight cDNA's. One of the cDNA's, which was contained within only one of the phage, was found to have some sequence similarity of a known desaturase gene from cyanobacteria, the DesA gene. Further sequence information was obtained for this clone. This additional sequence showed very significant sequence similarity to the DesA gene, confirming that the clone contained a desaturase gene. The remainder of the cDNA contained within the clone was sequenced and compared with the sequences of other known desaturases. The new desaturase was 53.0% identical to DesA at the nucleotide level and 43.9%, 45.6% and 47.0% identical to *B. napus* fad3, *Arabidopsis* fadD and *Arabidopsis* fadE, respectively. As the gene contained within the clone was significantly more similar in sequence to the DesA gene (which is a delta-12 desaturase) than to fad3, fadD or fadE (which are omega-3 desaturases), the new desaturase was expected to be a delta-12 (=Omega-6) desaturase.

The additional sequence data also indicated that this new desaturase gene contains a region that has only a one base pair mismatch to the desaturase consensus sequence described above. This mismatch means that the new desaturase has the sequence GHDCAH instead of GHDCGH.

A clone containing a full length cDNA for this gene was isolated and completely sequenced. This full length cDNA was sub-cloned into the plant transformation vector pBI121 such that the gene is transcribed under the control of the 35S promoter. This construct was then used to complement the phenotype of a fadC mutant (*Plant Phys.* 90: 522-529, 1989) of *Arabidopsis thaliana*, indicating that the gene encodes a chloroplastic omega-6 desaturase.

d. Proposed Isolation of fad2

The most highly conserved peptide regions in the linoleic desaturases and the DesA desaturase were chosen as regions likely to be conserved in oleic desaturases. These 8 conserved regions are shown in TABLE 6. These regions were chosen on the following basis: These regions have areas highly conserved between the 3 linoleic desaturases and DesA, with at least 4 identical amino acids over a 10 amino acid span. Once a region was identified as conserved, the fad3 linoleic desaturase sequence was used as the amino acid sequence for the source of homology to identify oleic desaturases. This is because both fad3 and the non-plastid oleic desaturases are thought to be localized to the endoplasmic reticulum and are most likely to contain similar amino acid sequences.

Several peptide endpoints in each conserved area were chosen as the basis to subsequently design oligonucleotide probes for identifying the oleic desaturase gene. The peptide endpoints were chosen to be between 5 and 9 amino acids in length. The peptide end points were chosen to end on the conserved (identical) amino acids, and most often to begin on conserved amino acids. The rationale is that within the larger conserved area, some amino acid portions are more highly conserved than others, that 15 to 27 (5 to 9 amino acids) nucleotides is a good primer size for PCR, and that for PCR it is important that the 3' end of the primer matches the target, with the conserved (identical) amino acids the most likely to be present in the oleic desaturases. These 28 "oleic desaturase" peptide targets (Table 6) are the basis oligonucleotides that are designed for hybridizing to the oleic desaturase cDNA sequences to identify and isolate the oleic desaturase cDNA clone.

Several possible methods for designing oligonucleotides and isolating the genes encoding the target peptide regions are known. For a discussion of designing degenerate oligonucleotides see *PCR Protocols—A Guide to Methods and Applications*, Eds M. A. Innis, D. H. Gelfand, J J Sninsky and T. J. White, Academic Press, San Diego, Calif., 1990; and SanXXXXX The two most common screening methods using the oligonucleotides are screening cDNA libraries and PCR amplification of specific cDNAs. Gene probes from fad3, fadD and fadE are used under stringent hybridization conditions to identify these cDNAs and discard them in the screen for oleic desaturase cDNA clones. The method for using degenerate oligonucleotides to screen a cDNA library has been described in the example above demonstrating the isolation of the fadC oleic desaturase gene. An immature plant seed active in oil biosynthesis, generally 2 to 5 weeks after pollination, preferably about 3 to 4 weeks after pollination, of a plant such as *Arabidopsis* or canola is used as the source of mRNA for making cDNA. First strand cDNA is made from the isolated mRNA and hybridized under stringent conditions in solution to an excess of biotinylated fad3, fadD and fadE cloned cDNAs. The hybrids and biotinylated nucleic acids are removed with strepavidin and a second round of substraction is done to remove any remaining fad3, fadD and fadE sequences. The cDNA remaining in solution is used for PCR reactions. (For 5' RACE, see below, a polyA tail is added to the first strand cDNA 3' end).

A method that can readily evaluate a number of degenerate oligonucleotides probes is degenerate PCR (See chapters by Compton and by Lee and Caskey in *PCR Protocols*, cited above). In this method a degenerate set of oligonucleotides encompassing all the possible codon choices for the target peptide is synthesized (such degenerate targets (Table 6) are the basis oligonucleotides that are designed for hybridizing to the oleic desaturase cDNA sequences to identify and isolate the oleic desaturase cDNA clone.

Several possible methods for designing oligonucleotides and isolating the genes encoding the target peptide regions are known. For a discussion of designing degenerate oligonucleotides see *PCR Protocols—A Guide to Methods and Applications*, Eds M. A. Innis, D. H. Gelfand, J J Sninsky and T. J. White, Academic Press, San Diego, Calif., 1990; and Sambrook. The two most common screening methods using the oligonucleotides are screening cDNA libraries and PCR amplification of specific cDNAs. Gene probes from fad3, fadD and fadE are used under stringent hybridization conditions to identify these cDNAs and discard them in the screen for oleic desaturase cDNA clones. The method for using degenerate oligonucleotides to screen a cDNA library has been described in the example above demonstrating the isolation of the fadC oleic desaturase gene. An immature plant seed active in oil biosynthesis, generally 1 to 5 weeks after pollination, preferably about 2 to 4 weeks after pollination, of a plant such as *Arabidopsis* or canola is used as the source of mRNA for making cDNA. First strand cDNA is made from the isolated mRNA and hybridized under stringent conditions in solution to an excess of biotinylated fad3, fadD and fadE cloned cDNAs. The hybrids and biotinylated nucleic acids are removed with strepavidin and a second round of substraction is done to remove any remaining fad3, fadD and fadE sequences. The cDNA remaining in solution is used for PCR reactions. (For 5' RACE, see below, a polyA tail is added to the first strand cDNA 3' end).

A method that can readily evaluate a number of degenerate oligonucleotides probes is degenerate PCR (See chapters by Compton and by Lee and Caskey in *PCR Protocols*, cited above). In this method a degenerate set of oligonucleotides encompassing all the possible codon

TABLE 7

Peptide Targets for Fad2 cloning

| | Peptide sequence | Oligo sequence 5' - 3' |
|---|---|---|
| 1a | DIRAAIP | GAYATHMGNGCNGCNATHCC |
| 1b | AIPKHC | GCNATHCCNAARCAYTG |
| 1c | KHCWVK | AARCAYTGYTGGGTNAA |
| 2a | WFLWPLYW | TGGTTYYTNTGGCCNYTNTAYTGG |
| 2b | WFLWP | TGGTTYYTNTGGCCN |
| 2c | WPLYW | TGGCCNYTNTAYTGG |
| 2d | WVAQGT | TGGGTNGCNCARGGNAC |
| 3a | FVLGHD | TTYGTNYTNGGNCAYGA |
| 3b | VLGHDC | GTNYTNGGNCAYGAYTG |
| 3c | GHDCGH | GGNCAYGAYTGYGGNCA |
| 3d | CGHGSF | TGYGGNCAYGGNWSNTT |
| 4a | PYHGW | CCNTAYCAYGGNTGG |
| 4b | HGWRISH | CAYGGNTGGMGNATHWSNCA |
| 4c-1 | WRISHRTHH | TGGMGNATHTCNCAYMGNACNCAYCA* |
| 4c-2 | | TGGMGNATHAGYCAYMGNACNCAYCA* |
| 4d | WRISH | TGGMGNATHWSNCAY |
| 4e | HRTHH | CAYMGNACNCAYCAY |
| 5a | ENDESW | GARAAYGAYGARWSNTGG |
| 5b | DESWVP | GAYGARWSNTGGGTNCC |
| 6a | WLDAVT | NGTNACNGCRTCNARCCA |
| 6b | TYLHH | RTGRTGNARRTANGT |
| 7a-1 | WSYLRGGL | ARNCCNCCNCKNARRTARCTCCA* |
| 7a-2 | | ARNCCNCCNCKNARRTANGACCA* |
| 7b | LTTIDRD | RTCNCKRTCDATNGTNGTNA |
| 7c | TIDRDY | RTARTCNCKRTCDATNGT |
| 8a | HDIGTH | RTGNGTNCCDATRTCRTG |
| 8b | HVIHHL | NARRTGRTGDATNACRTG |
| 8c | HHLFPQI | DATYTGNGGRAANARRTGRTG |
| 8d | HLFPQIP | GGDATYTGNGGRAANARRTG |
| 8e | LFPQIPHY | RTARTGNGGDATYTGNGGRAANA |

* synthesize 4c and 7a in two pools each to limit the degeneracy
Oligos for 6a - 8e are the complement of the coding sequence

TABLE 8

Table of Oligomers for PCR RACE of fad2

| Peptide # | Oligo Length | Fold Degeneracy | Similarity with L26296 | Similarity in Last 10 n.t. |
|---|---|---|---|---|
| 1a | 20 | 384 | 75% | 80% |
| 1b | 17 | 192 | 88 | 80 |
| 1c | 17 | 32 | 65 | 80 |
| 2a | 24 | 64 | 79 | 100 |
| 2b | 15 | 48 | 73 | 80 |
| 2c | 15 | 48 | 100 | 100 |
| 2d | 17 | 128 | 76 | 90 |
| 3a | 17 | 384 | 76 | 70 |
| 3b | 17 | 384 | 82 | 80 |
| 3c | 17 | 128 | 88 | 90 |
| 3d | 17 | 384 | 82 | 70 |
| 4a | 15 | 64 | 80 | 70 |
| 4b | 20 | 192 | 75 | 90 |
| 4c | 26 | 96* | 81 | 80 |
| 4d | 15 | 216 | 87 | 90 |
| 4e | 15 | 192 | 87 | 80 |
| 5a | 18 | 96 | 72 | 80 |
| 5b | 17 | 96 | 76 | 80 |
| 6a | 18 | 256 | 78 | 80 |
| 6b | 15 | 192 | 93 | 100 |
| 7a | 23 | 256* | 78 | 60 |
| 7b | 20 | 384 | 90 | 80 |
| 7c | 18 | 192 | 94 | 90 |
| 8a | 18 | 384 | 72 | 70 |
| 8b | 18 | 192 | 89 | 80 |
| 8c | 21 | 384 | 81 | 100 |
| 8d | 20 | 192 | 80 | 90 |
| 8e | 23 | 192 | 83 | 70 |

*done in two oligo pools

Table 7 shows the 28 peptide targets from the eight conserved regions and the 30 degenerate oligonucleotides derived from the peptide sequences. The degeneracy was kept to less than 516 fold, for those instances where more degeneracy occurred, by the use of deoxyinosine (Sambrook et al.) and by not including the last nucleotide in the last codon, and in two cases by the use of two subpools. Table 8 shows the amount of degeneracy for each designed oligonucleotide sequence and the amount of homology of the oligonucleotides to the *Arabidopsis* oleic desaturase fad2 (Accession No. L26296). Also shown in Table 8 is the percent homology in the last 10 nucleotides on the 3' end of each primer, since this region is most important for annealing and elongation under PCR conditions. It is expected that both 10 of 10 and 9 of 10 homology matches, and probably 8 of 10 homology matches in the 3' primer regions will serve as efficient PCR primers. Note that for oligonucleotide sets 1a through 5b (for 3' RACE) the strand direction is the same as the mRNA while for oligonucleotide sets 6a through 8e (for 5' RACE) the direction is opposite of the mRNA. Four oligonucleotides have a 10 of 10 match in the 3' position, 6 oligonucleotides match 9 of 10 in the 3' position and 12 match in 8 of 10 nucleotides in the 3' position. Oligonucleotides corresponding to peptides 2a, 2c, 2d, 3c, 4b, 4d, 6b, 7c, 8c, and 8d show 90% or greater homology in their last 10 nucleotides and anneal to the oleic desaturase gene and serve as primers to this gene. This demonstrates the validity of using the conserved regions of the plant linoleic desaturases and DesA to identify and isolate plant oleic desaturases.

The first round of PCR products are subjected to two rounds of subtraction using biotinylated fad3, fadD and fadE cloned cDNA to remove any hybridizing fad3, fadD and fadE sequences with strepavidin. This subtracted DNA is greatly enriched for fad2 sequences and depleted of fad3, fadD and fadE sequences. These 30 samples are run on agarose gels, blotted and hybridized with pools of probe from the 30 samples. Pools of 5 of each of the 30 PCR samples are labeled with random primers and hybridized to the blots of the 30 samples, for a total of 6 blots hybridized with 6 pools of 5 probes. Additionally, a pool of fad3, fadD and fadE probe is hybridized to a duplicate blot. Bands that do not hybridize strongly to fad3, fadD and fadE but do cross hybridize to probe made from a different sample are strong candidates for fad2 as fad2 is likely to be the only DNA amplified in two or more independent PCR reactions. Positively hybridizing lanes identify samples to amplify by PCR using the same primers as in the initial reaction for 5 to 10 cycles and the PCR products are cloned into plasmid vectors. The same probe that recognized the sample on the blot is used to screen the library and identify the hybridizing clone. Positive clones are sequenced and identified as fad2 clones by their homology but non-identity with fad3, and further characterized as described below.

In the event that fad2 sequences are not sufficiently enriched in one round of PCR to be identified, a second round of PCR is performed. If the lack of detection is due to insufficient amplification of fad2, then another round of PCR using the same primers on the subtracted PCR first round samples and the same simple screen as described above will identify fad2. If there are too many competing non-specific reactions then a second round of PCR using a different primer combination will remove non-specific amplifications and enrich for fad2. To further enrich for fad2 sequences each of the initial 30 PCR samples (one for each oligonucleotide in Table 7) after subtraction as described above, is subjected to a second round of PCR reactions using a different primer combination than the first reaction. One of the primers would be the same degenerate oligonucleotide primer as in the first PCR reaction. The second primer would now be from one of the 30 primers in Table 7 from the opposite class, ie, primers from 1a to 5b form matched sets with primers from 6a to 8e (primers 1a to 5b are in the sense direction while primers 6a to 8e are in the antisense direction). For example, if oligonucleotide 1a was used initially, it is used again as one of the two primers and the second primer is each of the 6a to 8e oligonucleotides for a total of 11 separate PCR reactions. In total the 30 initial reactions result in 418 second cycle PCR reactions, a number easily handled by PCR technology. Essentially this second PCR cycle accomplishes a "nested" or sequential PCR reaction step after removing all the linoleic desaturases by the subtraction step. This increases the amplification as well as the specificity. Identification of samples containing fad2 are performed similarly as described above, with the 418 samples dot blotted onto 22 filters and probed with 21 pools of 20 samples and with a pool of fad3, fadD and fadE. Again, any sample that cross hybridizes with an independent probe sample and does not hybridize to fad3, fadD and fadE is a candidate for containing fad2 in the sample. If fad3, fadD and fadE hybridization is still present, another biotinylation/stepavidin subtraction should remove it. Positively hybridizing samples are run on gels, the band identified by hybridization and isolated for cloning. This second set of PCR reactions produces PCR products of a predictable size since both primers are within the coding region where little variation in size is expected. Thus the presence of a band of the expected size on a gel is diagnostic of fad2, particularly if hybridization of a blot of such a gel with a fad3, fadD and fadE probe indicates the band is not due to fad3, fadD and fadE contamination. After cloning the inserts in *E. coli*, the resulting plasmids containing the insert are identified by hybridization. They are sequenced and identified as oleic desaturases by their homology but non-identity with the linoleic desaturases, as in the examples described previously. The full length clone of these cDNAs is obtained by standard methods and inserted into plant gene expression and transformation vectors and transformed into *Arabidopsis* fad2 mutants to confirm the identity of the oleic desaturase by genetic complemention as was described in the example with linoleic desaturase.

Thus in this approach to isolating the plant oleic desaturases, the total number of peptide regions is 8, comprised of 28 smaller peptide targets. This leads to set of 30 degenerate oligonucleotides, that are used in the PCR amplification and screening of the PCR products. Subtraction of interfering fad3, fadD and fadE sequences is used at several points. If necessary a second round of PCR reactions with paired internal primers gives extra amplification and specificity. This approach identifies the plant oleic desaturases, and the sequence of the isolated clones should confirm their identity by their homology to the plant linoleic desaturases as described. Thus a defined approach to isolating the plant oleic desaturases from the information about linoleic desaturases is presented here. The example given here is for *Arabidopsis* or canola oleic desaturases, but the approach is not limited to those plants as the oleic desaturases are probably highly conserved in most plants. Thus once one plant oleic desaturase is isolated, the sequence information is used to isolate the genes from other plant species by direct hybridization or by an approach similar to the one described here.

The following documents, which are cited in the above application, are hereby incorporated by reference.

Ammirato, P. V., et al. Handbook of Plant Cell Culture—Crop Species. Macmillan Publ. Co. (1984).

Bartlett, S. G., A. R. Grossman, & N. H. Chua. (1982) In Methods in Chloroplast Molecular Biology. Elsevier Biomedical Press, New York, pp 1081-1091.

Beachy, R. N., Chen, Z. L., Horsch, R. B., Rogers, S. G., Hoffmann, N.J., and Fraley, R. T. (1985) EMBO J, 4:3047-3053.

Benfey, P., Ren, L., and Chua, N. H. (1989) EMBO J, Vol. 5, no. 8, pp 2195-2202.

Bevan, M. (1984) Nucleic Acids Res. 12 (22): 8711-8721.

Bird, Q. R., and Ray, J. A. (1991) Biotech. Gen. Engin. Rev. 9:207-227.

Bray, E. A., Naito, S., Pan, N. S., Anderson, E., Dube, P., and Beachy, R. N. (1987) Planta 172:364-370.

Browse J., McCourt P., Somerville C. R. (1985) Science 227:763-65.

Browse, J., P. J. McCourt, C. R. Somerville. (1986) Anal. Biochem. 152:141-146.

Browse, J., P. McCourt, C. R. Somerville. (1986b) Plant Physiol. 81:859-864.

Browse, J. A., Slack, C. R. (1981.) FEBS Lett. 131:111-14

Browse, J., Somerville, C. R. (1991) Ann. Rev. Plant Physiol. Mol. Biol. 42:467-506.

Chang, C., Bowman, J. L., DeJohn, A. W., Lander, E. S., Meyerowitz, E. M. (1988) Proc Natl Acad Sci USA 85:6856-6860

Christou, P., McCabe, D. E., Martinell, B. J., and Swain, W. F. (1990) Trends Biotechnol 8:145-151.

Church, G. M., and Gilbert, W. (1984) Genomic sequencing. Proc Natl Acad Sci USA 81:1991-1995

Doyle, J. J., Schuler, M. A., Godette, W. D., Zenger, V., and Beachy, R. N. (1986). J Biol Chem 261:9228-9238.

Farmer, E. E., and Ryan, C. A. (1992) Plant Cell 4:129-134.

Fromm, M., (1990) UCLA Symposium on Molecular Strategies for Crop Improvement, Apr. 16-22, 1990. Keystone, CO.

Grill, E., and C. R. Somerville (1991) Molec. Gen. Genet., 226:484-490.

Harwood, J. L. (1988) Annu Rev Plant Physiol. 39:101-38

Herrera-Estrella, L., et al. (1983) Nature 303:209

Hinchee, M. A. W., Connor-Ward, D. V., Newell, C. A., McDonnell, R. E., Sato, S. J., Gasser, C. S., Fischoff, D. A., Re, D. B., Fraley, R. T., Horsch, R. B. (1988) Bio/Technology 6:915-922.

Horsch, R. B. and H. Klee. (1986) Proc. Natl. Acad. Sci. U.S.A. 83:4428-32.

Hugly, S., Kunst, L., and Somerville, C. R. (1991) J. Hered. 82:484-488.

Hugly, S., and Somerville, C. R. (1992) Plant Physiol. 99:197-202.

Katagiri, F., E. Lam and N. Chua. (1989) Nature 340:727-730.

Kearns, E. V., S. Hugly, C. R. Somerville (1991) Arch. Biochem. Biophys., 284:431-436.

Klee, H. J., et al. (1985) Bio/Technology 3:637-42.

Knutson, D. S., Thompson, G. A., Radke, S. E., Johnson, W. B., Knauf, V. C., and Kridl, J. C. (1992) Proc. Natl. Acad. Sci. USA 89:2624-2628.

Lemieux, B. M. Miquel, C. R. Somerville, J. (1990) Theor. Appl. Genet., 80:234-240.

Lipman, D. J., and Pearson, W. R. (1985) Science 227:1435-1441.

McKeon T. A., Stumpf, P. K. (1982) J. Biol. Chem. 257: 12141-47

McCourt, P., Kunst, L., Browse, J., Somerville, C. R. (1987) Plant Physiol. 84:353-361.

McSheffrey, S. A., McHughen A. and Devine, M. D., (1992) Theor. Appl. Genet., 84:480-486.

Meinke, D. W., Chen, J., and Beachy, R. N. (1981) Planta 153:130-139.

Mersereau, M., Pazour, J., and Das, A. (1990) Gene 90:149-151.

Rogers, S., et al. (1987) In 153 Methods in Enzymology. Edited by H. Weissbach and A. Weissbach. 253: Academic Press.

Samac, D. A., C. M. Hironaka, P. E. Yallaly and D. M. Shah (1990) Plant Physiol. 93:907-914.

Sambrook, J., Fritsch, E. F., and Maniatis, T. (1989) Molecular Cloning: A Laboratory Manual, Cold Spring Harbor Press, Cold Spring Harbor, N.Y.

Shanklin, J., C. R. Somerville. (1991) Proc. Natl. Acad. Sci. USA 88:2510-2514.

Schilperoot et al, EPO publication 120,516

Schmidhauser, T. J. and D. R. Helinski. (1985) J. Bacteriol. 164: 155.

Schmidt, H., Heinz, E. (1990a) Plant Physiol. 94:214-20

Schmidt, H., Heinz, E. (1990b) Proc. Natl. Acad. Sci. USA. 87:9477-9480.

Sherman, F., Fink, J., and Hicks, J. B. (1986) Laboratory Course Manual for Methods in Yeast Genetics. Cold Spring Harbor Laboratory Press, Cold Spring Harbor, N.Y.

Shimamoto, K. et al. (1989) Nature 338:274-276.

Steponkus, P. L., Lynch, D. V., and Vemura, M. (1990) Phil. Trans. Roy. Soc. Lond. B. 326:571-583.

Sukumaran, N. P. and Weiser, C. J. (1972) HortScience 7:467-468.

Vasil, V., F. Redway and I. Vasil. (1990) Bio/Technology 8:429-434.

Wada, H., Gombos, Z., Murata, N. (1990) Nature 347:200-203.

Vollrath, D., Davis, R. W. (1987) Nucleic Acids Res 15:7865-7876.

Ward, E. R., Jen, G. C. (1990) Plant Mol Biol 14:561-568.

The invention claimed:

1. A genetically transformed plant which has an elevated linolenic acid content relative to non-transformed plants of the same species, comprising a recombinant, double-stranded DNA molecule comprising:
   (i) a promoter that functions in plant cells to cause the production of an RNA sequence, said promoter operably linked to;
   (ii) a structural coding sequence comprising a sequence encoding the protein SEQ ID NO:2 or 12, wherein said protein has linoleic acid desaturase activity; and
   (iii) a 3' non-translated region that functions in plant cells to promote polyadenylation of the 3' end of said RNA sequence.

2. The plant of claim 1 in which the sequence encoding SEQ ID NO:2 is comprised within SEQ ID NO:1.

3. The plant of claim 1 in which the sequence encoding SEQ ID NO:12 is comprised within SEQ ID NO:11.

4. The plant of claim 1 in which the promoter of (i) is an endogenous plant linoleic acid desaturase promoter.

5. The plant of claim 1 in which the structural coding sequence of (ii) encodes a protein consisting of SEQ ID NO:2 or 12.

6. The plant of claim 1, which is sunflower, safflower, cotton, corn, wheat, rice, peanut, canola/oilseed rape, barley, sorghum, soybean, flax, tomato, almond, cashew or walnut.

7. A method of producing a genetically transformed plant which has an elevated linolenic acid content relative to non-transformed plants of the same species, comprising:
   (a) inserting into the genome of a plant cell a recombinant, double-stranded DNA molecule comprising:
      (i) a promoter that functions in plant cells to cause the production of an RNA sequence, said promoter operably linked to;
      (ii) a structural coding sequence comprising a sequence encoding the protein SEQ ID NO:2 or 12, wherein said protein has linoleic acid desaturase activity; and (iii) a 3' non-translated region that functions in plant cells to promote polyadenylation of the 3' end of said RNA sequence;

(b) obtaining a transformed plant cell; and (c) regenerating from the transformed plant cell a genetically transformed plant which has an elevated linolenic acid content.

8. The method of claim 7 in which the sequence encoding SEQ ID NO:2 is comprised within SEQ ID NO:1.

9. The method of claim 7 in which the sequence encoding SEQ ID NO:12 is comprised within SEQ ID NO:11.

10. The method of claim 7 in which the structural coding sequence of (ii) encodes a protein consisting of SEQ ID NO:2 or 12.

11. The method of claim 7, wherein the transformed plant is sunflower, safflower, cotton, corn, wheat, rice,, peanut, canola/oilseed rape, barley, sorghum, soybean, flax, tomato, almond, cashew or walnut.

12. A DNA construct comprising:

(i) a promoter that functions in plant cells to cause the production of an RNA sequence, said promoter operably linked to;

(ii) a structural coding sequence comprising a sequence encoding the protein SEQ ID NO:2 or 12, wherein said protein has linoleic acid desaturase activity; and (iii) a 3' non-translated region that functions in plant cells to promote polyadenylation of the 3' end of said RNA sequence.

13. The DNA construct of claim 12 in which the sequence encoding SEQ ID NO:2 is comprised within SEQ ID NO:1.

14. The DNA construct of claim 12 in which the sequence encoding SEQ ID NO:12 is comprised within SEQ ID NO:11.

15. The DNA construct of claim 12 in which the promoter of (i) is an endogenous plant linoleic acid desaturase promoter.

16. The DNA construct of claim 12 in which the structural coding sequence of (ii) encodes a protein consisting of SEQ ID NO:2 or 12.

17. A transformed plant cell comprising the DNA construct of claim 12.

18. The transformed plant cell of claim 17 which is sunflower, safflower, cotton, corn, wheat, rice, peanut, canola/oilseed rape, barley, sorghum, soybean, flax, tomato, almond, cashew or walnut.

* * * * *

SEQUENCE LISTING (1) GENERAL INFORMATION:

(iii) NUMBER OF SEQUENCES: 72

(2) INFORMATION FOR SEQ ID NO: 1:

(i) SEQUENCE CHARACTERISTICS:
      (A) LENGTH: 1353 base pairs
      (B) TYPE: nucleic acid
      (C) STRANDEDNESS: double
      (D) TOPOLOGY: linear (ii) MOLECULE TYPE: cDNA (ix) FEATURE:
      (A) NAME/KEY: CDS
      (B) LOCATION: 87..1238

(xi) SEQUENCE DESCRIPTION: SEQ ID NO: 1:

```
AATCCATCAA ACCTTTATTC ACCACATTTC ACTGAAAGGC CACACATCTA GAGAGAGAAA          60

CTTCGTCCAA ATCTCTCTCT CCAGCG ATG GTT GTT GCT ATG GAC CAG CGC AGC         113
                             Met Val Val Ala Met Asp Gln Arg Ser
                               1               5

AAT GTT AAC GGA GAT TCC GGT GCC CGG AAG GAA GAA GGG TTT GAT CCA          161
Asn Val Asn Gly Asp Ser Gly Ala Arg Lys Glu Glu Gly Phe Asp Pro
 10              15                  20                  25

AGC GCA CAA CCA CCG TTT AAG ATC GGA GAT ATA AGG GCG GCG ATT CCT          209
Ser Ala Gln Pro Pro Phe Lys Ile Gly Asp Ile Arg Ala Ala Ile Pro
                 30                  35                  40

AAG CAT TGC TGG GTG AAG AGT CCT TTG AGA TCT ATG AGC TAC GTC ACC          257
Lys His Cys Trp Val Lys Ser Pro Leu Arg Ser Met Ser Tyr Val Thr
             45                  50                  55

AGA GAC ATT TTC GCC GTC GCG GCT CTG GCC ATG GCC GCC GTG TAT TTT          305
Arg Asp Ile Phe Ala Val Ala Ala Leu Ala Met Ala Ala Val Tyr Phe
         60                  65                  70

GAT AGC TGG TTC CTC TGG CCA CTC TAC TGG GTT GCC CAA GGA ACC CTT          353
Asp Ser Trp Phe Leu Trp Pro Leu Tyr Trp Val Ala Gln Gly Thr Leu
     75                  80                  85

TTC TGG GCC ATC TTC GTT CTT GGC CAC GAC TGT GGA CAT GGG AGT TTC          401
Phe Trp Ala Ile Phe Val Leu Gly His Asp Cys Gly His Gly Ser Phe
 90                  95                 100                 105

TCA GAC ATT CCT CTG CTG AAC AGT GTG GTT GGT CAC ATT CTT CAT TCA          449
Ser Asp Ile Pro Leu Leu Asn Ser Val Val Gly His Ile Leu His Ser
                110                 115                 120

TTC ATC CTC GTT CCT TAC CAT GGT TGG AGA ATA AGC CAT CGG ACA CAC          497
Phe Ile Leu Val Pro Tyr His Gly Trp Arg Ile Ser His Arg Thr His
            125                 130                 135

CAC CAG AAC CAT GGC CAT GTT GAA AAC GAC GAG TCT TGG GTT CCG TTG          545
His Gln Asn His Gly His Val Glu Asn Asp Glu Ser Trp Val Pro Leu
        140                 145                 150

CCA GAA AAG TTG TAC AAG AAC TTG CCC CAT AGT ACT CGG ATG CTC AGA          593
Pro Glu Lys Leu Tyr Lys Asn Leu Pro His Ser Thr Arg Met Leu Arg
    155                 160                 165

TAC ACT GTC CCT CTG CCC ATG CTC GCT TAC CCG ATC TAT CTG TGG TAC          641
Tyr Thr Val Pro Leu Pro Met Leu Ala Tyr Pro Ile Tyr Leu Trp Tyr
170                 175                 180                 185

AGA AGT CCT GGA AAA GAA GGG TCA CAT TTT AAC CCA TAC AGT AGT TTA          689
Arg Ser Pro Gly Lys Glu Gly Ser His Phe Asn Pro Tyr Ser Ser Leu
                190                 195                 200

TTT GCT CCA AGC GAG AGG AAG CTT ATT GCA ACT TCA ACT ACT TGC TGG          737
```

```
                Phe Ala Pro Ser Glu Arg Lys Leu Ile Ala Thr Ser Thr Thr Cys Trp
                                205                 210                 215

TCC ATA ATG TTG GCC ACT CTT GTT TAT CTA TCG TTC CTC GTT GAT CCA              785
Ser Ile Met Leu Ala Thr Leu Val Tyr Leu Ser Phe Leu Val Asp Pro
            220                 225                 230

GTC ACA GTT CTC AAA GTC TAT GGC GTT CCT TAC ATT ATC TTT GTG ATG              833
Val Thr Val Leu Lys Val Tyr Gly Val Pro Tyr Ile Ile Phe Val Met
            235                 240                 245

TGG TTG GAC GCT GTC ACG TAC TTG CAT CAT CAT GGT CAC GAT GAG AAG              881
Trp Leu Asp Ala Val Thr Tyr Leu His His His Gly His Asp Glu Lys
250                 255                 260                 265

TTG CCT TGG TAC AGA GGC AAG GAA TGG AGT TAT TTA CGT GGA GGA TTA              929
Leu Pro Trp Tyr Arg Gly Lys Glu Trp Ser Tyr Leu Arg Gly Gly Leu
                270                 275                 280

ACA ACT ATT GAT AGA GAT TAC GGA ATC TTC AAC AAC ATC CAT CAC GAC              977
Thr Thr Ile Asp Arg Asp Tyr Gly Ile Phe Asn Asn Ile His His Asp
            285                 290                 295

ATT GGA ACT CAC GTG ATC CAT CAT CTT TTC CCA CAA ATC CCT CAC TAT             1025
Ile Gly Thr His Val Ile His His Leu Phe Pro Gln Ile Pro His Tyr
            300                 305                 310

CAC TTG GTC GAT GCC ACG AGA GCA GCT AAA CAT GTG TTA GGA AGA TAC             1073
His Leu Val Asp Ala Thr Arg Ala Ala Lys His Val Leu Gly Arg Tyr
            315                 320                 325

TAC AGA GAG CCG AAG ACG TCA GGA GCA ATA CCG ATT CAC TTG GTG GAG             1121
Tyr Arg Glu Pro Lys Thr Ser Gly Ala Ile Pro Ile His Leu Val Glu
330                 335                 340                 345

AGT TTG GTC GCA AGT ATT AAA AAA GAT CAT TAC GTC AGT GAC ACT GGT             1169
Ser Leu Val Ala Ser Ile Lys Lys Asp His Tyr Val Ser Asp Thr Gly
                350                 355                 360

GAT ATT GTC TTC TAC GAG ACA GAT CCA GAT CTC TAC GTT TAT GCT TCT             1217
Asp Ile Val Phe Tyr Glu Thr Asp Pro Asp Leu Tyr Val Tyr Ala Ser
            365                 370                 375

GAC AAA TCT AAA ATC AAT TAACTTTCT TCCTAGCTCT ATTAGGAATA                     1265
Asp Lys Ser Lys Ile Asn
            380

AACACTCCTT CTCTTTTACT TATTTGTTTC TGCTTAAGT TTAAAATGTA CTCGTGAAAC            1325

CTTTTTTTTA TTAATGTATT TACGTTAC                                              1353

(2) INFORMATION FOR SEQ ID NO: 2:

(i) SEQUENCE CHARACTERISTICS:
        (A) LENGTH: 383 amino acids
        (B) TYPE: amino acid
        (D) TOPOLOGY: linear (ii) MOLECULE TYPE: protein (xi) SEQUENCE DESCRIPTION: SEQ ID NO: 2:

Met Val Val Ala Met Asp Gln Arg Ser Asn Val Asn Gly Asp Ser Gly
1               5                   10                  15

Ala Arg Lys Glu Glu Gly Phe Asp Pro Ser Ala Gln Pro Pro Phe Lys
                20                  25                  30

Ile Gly Asp Ile Arg Ala Ala Ile Pro Lys His Cys Trp Val Lys Ser
            35                  40                  45

Pro Leu Arg Ser Met Ser Tyr Val Thr Arg Asp Ile Phe Ala Val Ala
        50                  55                  60

Ala Leu Ala Met Ala Ala Val Tyr Phe Asp Ser Trp Phe Leu Trp Pro
65              70                  75                  80

Leu Tyr Trp Val Ala Gln Gly Thr Leu Phe Trp Ala Ile Phe Val Leu
```

```
                85                  90                  95
Gly His Asp Cys Gly His Gly Ser Phe Ser Asp Ile Pro Leu Leu Asn
            100                 105                 110
Ser Val Val Gly His Ile Leu His Ser Phe Ile Leu Val Pro Tyr His
            115                 120                 125
Gly Trp Arg Ile Ser His Arg Thr His His Gln Asn His Gly His Val
            130                 135                 140
Glu Asn Asp Glu Ser Trp Val Pro Leu Pro Glu Lys Leu Tyr Lys Asn
145                 150                 155                 160
Leu Pro His Ser Thr Arg Met Leu Arg Tyr Thr Val Pro Leu Pro Met
                165                 170                 175
Leu Ala Tyr Pro Ile Tyr Leu Trp Tyr Arg Ser Pro Gly Lys Glu Gly
            180                 185                 190
Ser His Phe Asn Pro Tyr Ser Ser Leu Phe Ala Pro Ser Glu Arg Lys
            195                 200                 205
Leu Ile Ala Thr Ser Thr Thr Cys Trp Ser Ile Met Leu Ala Thr Leu
            210                 215                 220
Val Tyr Leu Ser Phe Leu Val Asp Pro Val Thr Val Leu Lys Val Tyr
225                 230                 235                 240
Gly Val Pro Tyr Ile Ile Phe Val Met Trp Leu Asp Ala Val Thr Tyr
                245                 250                 255
Leu His His His Gly His Asp Glu Lys Leu Pro Trp Tyr Arg Gly Lys
            260                 265                 270
Glu Trp Ser Tyr Leu Arg Gly Gly Leu Thr Thr Ile Asp Arg Asp Tyr
            275                 280                 285
Gly Ile Phe Asn Asn Ile His His Asp Ile Gly Thr His Val Ile His
            290                 295                 300
His Leu Phe Pro Gln Ile Pro His Tyr His Leu Val Asp Ala Thr Arg
305                 310                 315                 320
Ala Ala Lys His Val Leu Gly Arg Tyr Tyr Arg Glu Pro Lys Thr Ser
                325                 330                 335
Gly Ala Ile Pro Ile His Leu Val Glu Ser Leu Val Ala Ser Ile Lys
            340                 345                 350
Lys Asp His Tyr Val Ser Asp Thr Gly Asp Ile Val Phe Tyr Glu Thr
            355                 360                 365
Asp Pro Asp Leu Tyr Val Tyr Ala Ser Asp Lys Ser Lys Ile Asn
            370                 375                 380

(2) INFORMATION FOR SEQ ID NO: 3:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 3:

GGCGATGCTG TCGGAATGGA CGATA                                           25

(2) INFORMATION FOR SEQ ID NO: 4:

(i) SEQUENCE CHARACTERISTICS:
        (A) LENGTH: 27 base pairs
        (B) TYPE: nucleic acid
        (C) STRANDEDNESS: single
        (D) TOPOLOGY: linear
```

(ii) MOLECULE TYPE: cDNA (xi) SEQUENCE DESCRIPTION: SEQ ID NO: 4:

CTTGGAGCCA CTATCGACTA CGCGATC                                              27

(2) INFORMATION FOR SEQ ID NO: 5:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 5:

CCGATCTCAA GATTACGGAA T                                                    21

(2) INFORMATION FOR SEQ ID NO: 6:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 6:

TTCCTAATGC AGGAGTCGCA TAAG                                                 24

(2) INFORMATION FOR SEQ ID NO: 7:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 7:

AGGAGTCGCA TAAGGGAG                                                        18

(2) INFORMATION FOR SEQ ID NO: 8:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 8:

GGGAAGTGAA TGGAGAC                                                         17

(2) INFORMATION FOR SEQ ID NO: 9:

(i) SEQUENCE CHARACTERISTICS:
            (A) LENGTH: 1645 base pairs
            (B) TYPE: nucleic acid
            (C) STRANDEDNESS: double
            (D) TOPOLOGY: linear (ii) MOLECULE TYPE: cDNA (ix) FEATURE:

(A) NAME/KEY: CDS
(B) LOCATION: 125..1465

(xi) SEQUENCE DESCRIPTION: SEQ ID NO: 9:

```
GGAAAACACA AGTTTCTCTC ACACACATTA TCTCTTTCTC TATTACCACC ACTCATTCAT      60

AACAGAAACC CACCAAAAAA TAAAAGAGA GACTTTTCAC TCTGGGGAGA GAGCTCAAGT      120

TCTA ATG GCG AAC TTG GTC TTA TCA GAA TGT GGT ATA CGA CCT CTC CCC      169
     Met Ala Asn Leu Val Leu Ser Glu Cys Gly Ile Arg Pro Leu Pro
      1               5                  10                  15

AGA ATC TAC ACA ACA CCC AGA TCC AAT TTC CTC TCC AAC AAC AAC AAA      217
Arg Ile Tyr Thr Thr Pro Arg Ser Asn Phe Leu Ser Asn Asn Asn Lys
                 20                  25                  30

TTC AGA CCA TCA CTT TCT TCT TCT TCT TAC AAA ACA TCA TCA TCT CCT      265
Phe Arg Pro Ser Leu Ser Ser Ser Ser Tyr Lys Thr Ser Ser Ser Pro
             35                  40                  45

CTG TCT TTT GGT CTG AAT TCA CGA GAT GGG TTC ACG AGG AAT TGG GCG      313
Leu Ser Phe Gly Leu Asn Ser Arg Asp Gly Phe Thr Arg Asn Trp Ala
         50                  55                  60

TTG AAT GTG AGC ACA CCA TTA ACG ACA CCA ATA TTT GAG GAG TCT CCA      361
Leu Asn Val Ser Thr Pro Leu Thr Thr Pro Ile Phe Glu Glu Ser Pro
 65                  70                  75

TTG GAG GAA GAT AAT AAA CAG AGA TTC GAT CCA GGT GCG CCT CCT CCG      409
Leu Glu Glu Asp Asn Lys Gln Arg Phe Asp Pro Gly Ala Pro Pro Pro
 80                  85                  90                  95

TTC AAT TTA GCT GAT ATT AGA GCA GCT ATA CCT AAG CAT TGT TGG GTT      457
Phe Asn Leu Ala Asp Ile Arg Ala Ala Ile Pro Lys His Cys Trp Val
                 100                 105                 110

AAG AAT CCA TGG AAG TCT TTG AGT TAT GTC GTC AGA GAC GTC GCT ATC      505
Lys Asn Pro Trp Lys Ser Leu Ser Tyr Val Val Arg Asp Val Ala Ile
             115                 120                 125

GTC TTT GCA TTG GCT GCT GGA GCT GCT TAC CTC AAC AAT TGG ATT GTT      553
Val Phe Ala Leu Ala Ala Gly Ala Ala Tyr Leu Asn Asn Trp Ile Val
         130                 135                 140

TGG CCT CTC TAT TGG CTC GCT CAA GGA ACC ATG TTT TGG GCT CTC TTT      601
Trp Pro Leu Tyr Trp Leu Ala Gln Gly Thr Met Phe Trp Ala Leu Phe
 145                 150                 155

GTT CTT GGT CAT GAC TGT GGA CAT GGT AGT TTC TCA AAT GAT CCG AAG      649
Val Leu Gly His Asp Cys Gly His Gly Ser Phe Ser Asn Asp Pro Lys
 160                 165                 170                 175

TTG AAC AGT GTG GTC GGT CAT CTT CTT CAT TCC TCA ATT CTG GTC CCA      697
Leu Asn Ser Val Val Gly His Leu Leu His Ser Ser Ile Leu Val Pro
                 180                 185                 190

TAC CAT GGC TGG AGA ATT AGT CAC AGA ACT CAC CAC CAG AAC CAT GGA      745
Tyr His Gly Trp Arg Ile Ser His Arg Thr His His Gln Asn His Gly
             195                 200                 205

CAT GTT GAG AAT GAC GAA TCT TGG CAT CCT ATG TCT GAG AAA ATC TAC      793
His Val Glu Asn Asp Glu Ser Trp His Pro Met Ser Glu Lys Ile Tyr
         210                 215                 220

AAT ACT TTG GAC AAG CCG ACT AGA TTC TTT AGA TTT ACA CTG CCT CTC      841
Asn Thr Leu Asp Lys Pro Thr Arg Phe Phe Arg Phe Thr Leu Pro Leu
 225                 230                 235

GTG ATG CTT GCA TAC CCT TTC TAC TTG TGG GCT CGA AGT CCG GGG AAA      889
Val Met Leu Ala Tyr Pro Phe Tyr Leu Trp Ala Arg Ser Pro Gly Lys
 240                 245                 250                 255

AAG GGT TCT CAT TAC CAT CCA GAC AGT GAC TTG TTC CTC CCT AAA GAG      937
Lys Gly Ser His Tyr His Pro Asp Ser Asp Leu Phe Leu Pro Lys Glu
                 260                 265                 270

AGA AAG GAT GTC CTC ACT TCT ACT GCT TGT TGG ACT GCA ATG GCT GCT      985
Arg Lys Asp Val Leu Thr Ser Thr Ala Cys Trp Thr Ala Met Ala Ala
```

-continued

```
              275                 280                 285
CTG CTT GTT TGT CTC AAC TTC ACA ATC GGT CCA ATT CAA ATG CTC AAA    1033
Leu Leu Val Cys Leu Asn Phe Thr Ile Gly Pro Ile Gln Met Leu Lys
        290                 295                 300

CTT TAT GGA ATT CCT TAC TGG ATA AAT GTA ATG TGG TTG GAC TTT GTG    1081
Leu Tyr Gly Ile Pro Tyr Trp Ile Asn Val Met Trp Leu Asp Phe Val
    305                 310                 315

ACT TAC CTG CAT CAC CAT GGT CAT GAA GAT AAG CTT CCT TGG TAC CGT    1129
Thr Tyr Leu His His His Gly His Glu Asp Lys Leu Pro Trp Tyr Arg
320                 325                 330                 335

GGC AAG GAG TGG AGT TAC CTG AGA GGA GGA CTT ACA ACA TTG GAT CGT    1177
Gly Lys Glu Trp Ser Tyr Leu Arg Gly Gly Leu Thr Thr Leu Asp Arg
                340                 345                 350

GAC TAC GGA TTG ATC AAT AAC ATC CAT CAT GAT ATT GGA ACT CAT GTG    1225
Asp Tyr Gly Leu Ile Asn Asn Ile His His Asp Ile Gly Thr His Val
            355                 360                 365

ATA CAT CAT CTT TTC CCG CAG ATC CCA CAT TAT CAT CTA GTA GAA GCA    1273
Ile His His Leu Phe Pro Gln Ile Pro His Tyr His Leu Val Glu Ala
        370                 375                 380

ACA GAA GCA GCT AAA CCA GTA TTA GGG AAG TAT TAC AGG GAG CCT GAT    1321
Thr Glu Ala Ala Lys Pro Val Leu Gly Lys Tyr Tyr Arg Glu Pro Asp
    385                 390                 395

AAG TCT GGA CCG TTG CCA TTA CAT TTA CTG GAA ATT CTA GCG AAA AGT    1369
Lys Ser Gly Pro Leu Pro Leu His Leu Leu Glu Ile Leu Ala Lys Ser
400                 405                 410                 415

ATA AAA GAA GAT CAT TAC GTG AGC GAC GAA GGA GAA GTT GTA TAC TAT    1417
Ile Lys Glu Asp His Tyr Val Ser Asp Glu Gly Glu Val Val Tyr Tyr
                420                 425                 430

AAA GCA GAT CCA AAT CTC TAT GGA GAG GTC AAA GTA AGA GCA GAT TGA    1465
Lys Ala Asp Pro Asn Leu Tyr Gly Glu Val Lys Val Arg Ala Asp
            435                 440                 445

AATGAAGCAG GCTTGAGATT GAAGTTTTTT CTATTTCAGA CCAGCTGATT TTTTGCTTAC    1525

TGTATCAATT TATTGTGTCA CCCACCAGAG AGTTAGTATC TCTGAATACG ATCGATCAGA    1585

TGGAAACAAC AAATTTGTTT GCGATACTGA AGCTATATAT ACCATAAAAA AAAAAAAAAA    1645

(2) INFORMATION FOR SEQ ID NO: 10:

(i) SEQUENCE CHARACTERISTICS:
        (A) LENGTH: 446 amino acids
        (B) TYPE: amino acid
        (D) TOPOLOGY: linear (ii) MOLECULE TYPE: protein (xi) SEQUENCE DESCRIPTION: SEQ ID NO: 10:

Met Ala Asn Leu Val Leu Ser Glu Cys Gly Ile Arg Pro Leu Pro Arg
 1               5                  10                  15

Ile Tyr Thr Thr Pro Arg Ser Asn Phe Leu Ser Asn Asn Asn Lys Phe
                20                  25                  30

Arg Pro Ser Leu Ser Ser Ser Tyr Lys Thr Ser Ser Ser Pro Leu
        35                  40                  45

Ser Phe Gly Leu Asn Ser Arg Asp Gly Phe Thr Arg Asn Trp Ala Leu
    50                  55                  60

Asn Val Ser Thr Pro Leu Thr Thr Pro Ile Phe Glu Glu Ser Pro Leu
65                  70                  75                  80

Glu Glu Asp Asn Lys Gln Arg Phe Asp Pro Gly Ala Pro Pro Phe
                85                  90                  95

Asn Leu Ala Asp Ile Arg Ala Ala Ile Pro Lys His Cys Trp Val Lys
```

```
                100               105               110
Asn Pro Trp Lys Ser Leu Ser Tyr Val Val Arg Asp Val Ala Ile Val
            115                 120                 125

Phe Ala Leu Ala Ala Gly Ala Ala Tyr Leu Asn Asn Trp Ile Val Trp
130                 135                 140

Pro Leu Tyr Trp Leu Ala Gln Gly Thr Met Phe Trp Ala Leu Phe Val
145                 150                 155                 160

Leu Gly His Asp Cys Gly His Gly Ser Phe Ser Asn Asp Pro Lys Leu
                165                 170                 175

Asn Ser Val Val Gly His Leu Leu His Ser Ser Ile Leu Val Pro Tyr
            180                 185                 190

His Gly Trp Arg Ile Ser His Arg Thr His His Gln Asn His Gly His
            195                 200                 205

Val Glu Asn Asp Glu Ser Trp His Pro Met Ser Glu Lys Ile Tyr Asn
        210                 215                 220

Thr Leu Asp Lys Pro Thr Arg Phe Phe Arg Phe Thr Leu Pro Leu Val
225                 230                 235                 240

Met Leu Ala Tyr Pro Phe Tyr Leu Trp Ala Arg Ser Pro Gly Lys Lys
                245                 250                 255

Gly Ser His Tyr His Pro Asp Ser Asp Leu Phe Leu Pro Lys Glu Arg
            260                 265                 270

Lys Asp Val Leu Thr Ser Thr Ala Cys Trp Thr Ala Met Ala Ala Leu
        275                 280                 285

Leu Val Cys Leu Asn Phe Thr Ile Gly Pro Ile Gln Met Leu Lys Leu
        290                 295                 300

Tyr Gly Ile Pro Tyr Trp Ile Asn Val Met Trp Leu Asp Phe Val Thr
305                 310                 315                 320

Tyr Leu His His His Gly His Glu Asp Lys Leu Pro Trp Tyr Arg Gly
                325                 330                 335

Lys Glu Trp Ser Tyr Leu Arg Gly Gly Leu Thr Thr Leu Asp Arg Asp
            340                 345                 350

Tyr Gly Leu Ile Asn Asn Ile His His Asp Ile Gly Thr His Val Ile
            355                 360                 365

His His Leu Phe Pro Gln Ile Pro His Tyr His Leu Val Glu Ala Thr
370                 375                 380

Glu Ala Ala Lys Pro Val Leu Gly Lys Tyr Tyr Arg Glu Pro Asp Lys
385                 390                 395                 400

Ser Gly Pro Leu Pro Leu His Leu Leu Glu Ile Leu Ala Lys Ser Ile
                405                 410                 415

Lys Glu Asp His Tyr Val Ser Asp Glu Gly Glu Val Val Tyr Tyr Lys
            420                 425                 430

Ala Asp Pro Asn Leu Tyr Gly Glu Val Lys Val Arg Ala Asp
            435                 440                 445

(2) INFORMATION FOR SEQ ID NO: 11:

(i) SEQUENCE CHARACTERISTICS:
        (A) LENGTH: 1525 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 61..1368
```

(xi) SEQUENCE DESCRIPTION: SEQ ID NO: 11:

```
AGAGAGTGCA AATAGAACGA CAGAGACTTT TTCCTCTTTT CTTCTTGGGA AGAGGCTCCA        60

ATG GCG AGC TCG GTT TTA TCA GAA TGT GGT TTT AGA CCT CTC CCC AGA         108
Met Ala Ser Ser Val Leu Ser Glu Cys Gly Phe Arg Pro Leu Pro Arg
 1               5                  10                  15

TTC TAC CCT AAA CAC ACA ACC TCT TTT GCC TCT AAC CCT AAA CCC ACT         156
Phe Tyr Pro Lys His Thr Thr Ser Phe Ala Ser Asn Pro Lys Pro Thr
                20                  25                  30

TTC AAA TTC AAT CCA CCA CTT AAA CCT CCT TCT TCT CTT CTC AAT TCC         204
Phe Lys Phe Asn Pro Pro Leu Lys Pro Pro Ser Ser Leu Leu Asn Ser
             35                  40                  45

CGA TAT GGA TTC TAC TCT AAA ACC AGG AAC TGG GCA TTG AAT GTG GCA         252
Arg Tyr Gly Phe Tyr Ser Lys Thr Arg Asn Trp Ala Leu Asn Val Ala
         50                  55                  60

ACA CCT TTA ACA ACT CTT CAG TCT CCA TCC GAG GAA GAC ACG GAG AGA         300
Thr Pro Leu Thr Thr Leu Gln Ser Pro Ser Glu Glu Asp Thr Glu Arg
 65                  70                  75                  80

TTC GAC CCA GGT GCG CCT CCT CCC TTC AAT TTG GCG GAT ATA AGA GCA         348
Phe Asp Pro Gly Ala Pro Pro Pro Phe Asn Leu Ala Asp Ile Arg Ala
                 85                  90                  95

GCC ATA CCT AAG CAT TGT TGG GTT AAG AAT CCA TGG ATG TCT ATG AGT         396
Ala Ile Pro Lys His Cys Trp Val Lys Asn Pro Trp Met Ser Met Ser
                100                 105                 110

TAT GTT GTC AGA GAT GTT GCT ATC GTC TTT GGA TTG GCT GCT GTT GCT         444
Tyr Val Val Arg Asp Val Ala Ile Val Phe Gly Leu Ala Ala Val Ala
            115                 120                 125

GCT TAC TTC AAC AAT TGG CTT CTC TGG CCT CTC TAC TGG TTC GCT CAA         492
Ala Tyr Phe Asn Asn Trp Leu Leu Trp Pro Leu Tyr Trp Phe Ala Gln
        130                 135                 140

GGA ACC ATG TTC TGG GCT CTC TTT GTC CTT GGC CAT GAC TGC GGA CAT         540
Gly Thr Met Phe Trp Ala Leu Phe Val Leu Gly His Asp Cys Gly His
145                 150                 155                 160

GGT AGC TTC TCG AAT GAT CCG AGG CTG AAC AGT GTG GCT GGT CAT CTT         588
Gly Ser Phe Ser Asn Asp Pro Arg Leu Asn Ser Val Ala Gly His Leu
                165                 170                 175

CTT CAT TCC TCA ATT CTG GTC CCT TAC CAT GGC TGG AGG ATT AGC CAC         636
Leu His Ser Ser Ile Leu Val Pro Tyr His Gly Trp Arg Ile Ser His
            180                 185                 190

AGA ACT CAC CAC CAG AAC CAT GGT CAT GTC GAG AAT GAC GAA TCA TGG         684
Arg Thr His His Gln Asn His Gly His Val Glu Asn Asp Glu Ser Trp
        195                 200                 205

CAT CCT TTG CCT GAA AGC ATC TAC AAG AAT TTG GAA AAG ACG ACT CAA         732
His Pro Leu Pro Glu Ser Ile Tyr Lys Asn Leu Glu Lys Thr Thr Gln
    210                 215                 220

ATG TTT AGG TTT ACA CTG CCT TTT CCA ATG CTC GCA TAC CCT TTC TAC         780
Met Phe Arg Phe Thr Leu Pro Phe Pro Met Leu Ala Tyr Pro Phe Tyr
225                 230                 235                 240

TTG TGG AAC AGA AGT CCA GGG AAA CAA GGT TCT CAT TAT CAT CCG GAC         828
Leu Trp Asn Arg Ser Pro Gly Lys Gln Gly Ser His Tyr His Pro Asp
                245                 250                 255

AGT GAC TTG TTT CTT CCA AAA GAG AAG AAA GAT GTT CTG ACA TCA ACT         876
Ser Asp Leu Phe Leu Pro Lys Glu Lys Lys Asp Val Leu Thr Ser Thr
            260                 265                 270

GCC TGT TGG ACT GCA ATG GCT GCT TTG CTT GTT TGT CTC AAC TTT GTC         924
Ala Cys Trp Thr Ala Met Ala Ala Leu Leu Val Cys Leu Asn Phe Val
        275                 280                 285

ATG GGT CCA ATC CAG ATG CTC AAA CTA TAT GGC ATC CCT TAT TGG ATA         972
Met Gly Pro Ile Gln Met Leu Lys Leu Tyr Gly Ile Pro Tyr Trp Ile
```

-continued

```
         290                 295                 300
TTT GTA ATG TGG TTG GAC TTC GTC ACT TAC TTG CAC CAC CAT GGA CAT     1020
Phe Val Met Trp Leu Asp Phe Val Thr Tyr Leu His His His Gly His
305                 310                 315                 320

GAA GAC AAG CTC CCT TGG TAT CGT GGA AAG GAA TGG AGT TAC CTG AGA     1068
Glu Asp Lys Leu Pro Trp Tyr Arg Gly Lys Glu Trp Ser Tyr Leu Arg
                325                 330                 335

GGA GGG CTC ACA ACA TTA GAT CGT GAC TAC GGA TGG ATC AAT AAC ATC     1116
Gly Gly Leu Thr Thr Leu Asp Arg Asp Tyr Gly Trp Ile Asn Asn Ile
            340                 345                 350

CAC CAC GAT ATT GGA ACT CAT GTG ATA CAT CAT CTT TTC CCG CAG ATC     1164
His His Asp Ile Gly Thr His Val Ile His His Leu Phe Pro Gln Ile
        355                 360                 365

CCA CAT TAT CAT CTA GTA GAA GCA ACA GAA GCA GCT AAA CCA GTA CTA     1212
Pro His Tyr His Leu Val Glu Ala Thr Glu Ala Ala Lys Pro Val Leu
    370                 375                 380

GGA AAG TAC TAC AGA GAA CCG AAA AAC TCT GGA CCT CTG CCA CTT CAC     1260
Gly Lys Tyr Tyr Arg Glu Pro Lys Asn Ser Gly Pro Leu Pro Leu His
385                 390                 395                 400

TTA CTG GGA AGC CTC ATA AAG AGT ATG AAA CAA GAC CAT TTC GTA AGC     1308
Leu Leu Gly Ser Leu Ile Lys Ser Met Lys Gln Asp His Phe Val Ser
                405                 410                 415

GAT ACA GGA GAT GTC GTG TAC TAT GAG GCA GAT CCA AAA CTC AAT GGA     1356
Asp Thr Gly Asp Val Val Tyr Tyr Glu Ala Asp Pro Lys Leu Asn Gly
            420                 425                 430

CAA AGA ACA TGAGGACATA CTGCAGTGAA CCAGGCAGAC AAGTTACATA             1405
Gln Arg Thr
        435

AATTCATCTT GGCCCATTCA TTATGTTCTT TTTGTTTTGG TGTAAAGCCT TTCGAGATT    1465

AAAAAAGCAT TAATTTGTAG AAACCTGTGG TAAAACTCTC GATCAAATGA AATAAGATAT   1525

(2) INFORMATION FOR SEQ ID NO: 12:

(i) SEQUENCE CHARACTERISTICS:
        (A) LENGTH: 435 amino acids
        (B) TYPE: amino acid
        (D) TOPOLOGY: linear (ii) MOLECULE TYPE: protein (xi) SEQUENCE DESCRIPTION: SEQ ID NO: 12:

Met Ala Ser Ser Val Leu Ser Glu Cys Gly Phe Arg Pro Leu Pro Arg
1               5                   10                  15

Phe Tyr Pro Lys His Thr Thr Ser Phe Ala Ser Asn Pro Lys Pro Thr
                20                  25                  30

Phe Lys Phe Asn Pro Pro Leu Lys Pro Ser Ser Leu Leu Asn Ser
            35                  40                  45

Arg Tyr Gly Phe Tyr Ser Lys Thr Arg Asn Trp Ala Leu Asn Val Ala
        50                  55                  60

Thr Pro Leu Thr Thr Leu Gln Ser Pro Ser Glu Glu Asp Thr Glu Arg
65                  70                  75                  80

Phe Asp Pro Gly Ala Pro Pro Phe Asn Leu Ala Asp Ile Arg Ala
                85                  90                  95

Ala Ile Pro Lys His Cys Trp Val Lys Asn Pro Trp Met Ser Met Ser
            100                 105                 110

Tyr Val Val Arg Asp Val Ala Ile Val Phe Gly Leu Ala Ala Val Ala
        115                 120                 125

Ala Tyr Phe Asn Asn Trp Leu Leu Trp Pro Leu Tyr Trp Phe Ala Gln
```

-continued

```
                130                 135                 140
Gly Thr Met Phe Trp Ala Leu Phe Val Leu Gly His Asp Cys Gly His
145                 150                 155                 160

Gly Ser Phe Ser Asn Asp Pro Arg Leu Asn Ser Val Ala Gly His Leu
                165                 170                 175

Leu His Ser Ser Ile Leu Val Pro Tyr His Gly Trp Arg Ile Ser His
                180                 185                 190

Arg Thr His His Gln Asn His Gly His Val Glu Asn Asp Glu Ser Trp
                195                 200                 205

His Pro Leu Pro Glu Ser Ile Tyr Lys Asn Leu Glu Lys Thr Thr Gln
210                 215                 220

Met Phe Arg Phe Thr Leu Pro Phe Pro Met Leu Ala Tyr Pro Phe Tyr
225                 230                 235                 240

Leu Trp Asn Arg Ser Pro Gly Lys Gln Gly Ser His Tyr His Pro Asp
                245                 250                 255

Ser Asp Leu Phe Leu Pro Lys Glu Lys Asp Val Leu Thr Ser Thr
                260                 265                 270

Ala Cys Trp Thr Ala Met Ala Ala Leu Leu Val Cys Leu Asn Phe Val
                275                 280                 285

Met Gly Pro Ile Gln Met Leu Lys Leu Tyr Gly Ile Pro Tyr Trp Ile
290                 295                 300

Phe Val Met Trp Leu Asp Phe Val Thr Tyr Leu His His Gly His
305                 310                 315                 320

Glu Asp Lys Leu Pro Trp Tyr Arg Gly Lys Glu Trp Ser Tyr Leu Arg
                325                 330                 335

Gly Gly Leu Thr Thr Leu Asp Arg Asp Tyr Gly Trp Ile Asn Asn Ile
                340                 345                 350

His His Asp Ile Gly Thr His Val Ile His His Leu Phe Pro Gln Ile
                355                 360                 365

Pro His Tyr His Leu Val Glu Ala Thr Glu Ala Ala Lys Pro Val Leu
                370                 375                 380

Gly Lys Tyr Tyr Arg Glu Pro Lys Asn Ser Gly Pro Leu Pro Leu His
385                 390                 395                 400

Leu Leu Gly Ser Leu Ile Lys Ser Met Lys Gln Asp His Phe Val Ser
                405                 410                 415

Asp Thr Gly Asp Val Val Tyr Tyr Glu Ala Asp Pro Lys Leu Asn Gly
                420                 425                 430

Gln Arg Thr
        435
```

(2) INFORMATION FOR SEQ ID NO: 13:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO: 13:

GAYATHMGNG CNGCNATHCC                                      20

(2) INFORMATION FOR SEQ ID NO: 14:

(i) SEQUENCE CHARACTERISTICS:
        (A) LENGTH: 17 base pairs

```
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO: 14:

GCNATHCCNA ARCAYTG                                                    17

(2) INFORMATION FOR SEQ ID NO: 15:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO: 15:

AARCAYTGYT GGGTNAA                                                    17

(2) INFORMATION FOR SEQ ID NO: 16:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO: 16:

TGGTTYYTNT GGCCNYTNTA YTGG                                            24

(2) INFORMATION FOR SEQ ID NO: 17:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO: 17:

TGGTTYYTNT GGCCN                                                      15

(2) INFORMATION FOR SEQ ID NO: 18:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO: 18:

TGGCCNYTNT AYTGG                                                      15

(2) INFORMATION FOR SEQ ID NO: 19:

(i) SEQUENCE CHARACTERISTICS:
        (A) LENGTH: 17 base pairs
        (B) TYPE: nucleic acid
        (C) STRANDEDNESS: single
        (D) TOPOLOGY: linear
```

(ii) MOLECULE TYPE: DNA (synthetic)

(xi) SEQUENCE DESCRIPTION: SEQ ID NO: 19:

TGGGTNGCNC ARGGNAC                                                      17

(2) INFORMATION FOR SEQ ID NO: 20:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: DNA (synthetic)

(xi) SEQUENCE DESCRIPTION: SEQ ID NO: 20:

TTYGTNYTNG GNCAYGA                                                      17

(2) INFORMATION FOR SEQ ID NO: 21:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: DNA (synthetic)

(xi) SEQUENCE DESCRIPTION: SEQ ID NO: 21:

GTNYTNGGNC AYGAYTG                                                      17

(2) INFORMATION FOR SEQ ID NO: 22:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: DNA (synthetic)

(xi) SEQUENCE DESCRIPTION: SEQ ID NO: 22:

GGNCAYGAYT GYGGNCA                                                      17

(2) INFORMATION FOR SEQ ID NO: 23:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: DNA (synthetic)

(xi) SEQUENCE DESCRIPTION: SEQ ID NO: 23:

TGYGGNCAYG GNWSNTT                                                      17

(2) INFORMATION FOR SEQ ID NO: 24:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (ii) MOLECULE TYPE: DNA (synthetic)

(xi) SEQUENCE DESCRIPTION: SEQ ID NO: 24:

```
CCNTAYCAYG GNTGG                                                        15

(2) INFORMATION FOR SEQ ID NO: 25:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (ii) MOLECULE TYPE: DNA (synthetic)

(xi) SEQUENCE DESCRIPTION: SEQ ID NO: 25:

CAYGGNTGGM GNATHWSNCA                                                   20

(2) INFORMATION FOR SEQ ID NO: 26:

(i) SEQUENCE CHARACTERISTICS:
          (A) LENGTH: 26 base pairs
          (B) TYPE: nucleic acid
          (C) STRANDEDNESS: single
          (D) TOPOLOGY: linear (ii) MOLECULE TYPE: DNA (synthetic)

(xi) SEQUENCE DESCRIPTION: SEQ ID NO: 26:

TGGMGNATHT CNCAYMGNAC NCAYCA                                            26

(2) INFORMATION FOR SEQ ID NO: 27:

(i) SEQUENCE CHARACTERISTICS:
          (A) LENGTH: 26 base pairs
          (B) TYPE: nucleic acid
          (C) STRANDEDNESS: single
          (D) TOPOLOGY: linear (ii) MOLECULE TYPE: DNA (synthetic)

(xi) SEQUENCE DESCRIPTION: SEQ ID NO: 27:

TGGMGNATHA GYCAYMGNAC NCAYCA                                            26

(2) INFORMATION FOR SEQ ID NO: 28:

(i) SEQUENCE CHARACTERISTICS:
          (A) LENGTH: 15 base pairs
          (B) TYPE: nucleic acid
          (C) STRANDEDNESS: single
          (D) TOPOLOGY: linear (ii) MOLECULE TYPE: DNA (synthetic)

(xi) SEQUENCE DESCRIPTION: SEQ ID NO: 28:

TGGMGNATHW SNCAY                                                        15

(2) INFORMATION FOR SEQ ID NO: 29:

(i) SEQUENCE CHARACTERISTICS:
          (A) LENGTH: 15 base pairs
          (B) TYPE: nucleic acid
          (C) STRANDEDNESS: single
          (D) TOPOLOGY: linear (ii) MOLECULE TYPE: DNA (synthetic)

(xi) SEQUENCE DESCRIPTION: SEQ ID NO: 29:

CAYMGNACNC AYCAY                                                        15

(2) INFORMATION FOR SEQ ID NO: 30:
```

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO: 30:

GARAAYGAYG ARWSNTGG                                                    18

(2) INFORMATION FOR SEQ ID NO: 31:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO: 31:

GAYGARWSNT GGGTNCC                                                     17

(2) INFORMATION FOR SEQ ID NO: 32:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO: 32:

NGTNACNGCR TCNARCCA                                                    18

(2) INFORMATION FOR SEQ ID NO: 33:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO: 33:

RTGRTGNARR TANGT                                                       15

(2) INFORMATION FOR SEQ ID NO: 34:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO: 34:

ARNCCNCCNC KNARRTARCT CCA                                              23

(2) INFORMATION FOR SEQ ID NO: 35:

(i) SEQUENCE CHARACTERISTICS:
        (A) LENGTH: 23 base pairs
        (B) TYPE: nucleic acid (C) STRANDEDNESS: single
                (D) TOPOLOGY: linear (ii) MOLECULE TYPE: DNA (synthetic)

(xi) SEQUENCE DESCRIPTION: SEQ ID NO: 35:

ARNCCNCCNC KNARRTANGA CCA                                        23

(2) INFORMATION FOR SEQ ID NO: 36:

(i) SEQUENCE CHARACTERISTICS:
                (A) LENGTH: 20 base pairs
                (B) TYPE: nucleic acid
                (C) STRANDEDNESS: single
                (D) TOPOLOGY: linear (ii) MOLECULE TYPE: DNA (synthetic)

(xi) SEQUENCE DESCRIPTION: SEQ ID NO: 36:

RTCNCKRTCD ATNGTNGTNA                                            20

(2) INFORMATION FOR SEQ ID NO: 37:

(i) SEQUENCE CHARACTERISTICS:
                (A) LENGTH: 18 base pairs
                (B) TYPE: nucleic acid
                (C) STRANDEDNESS: single
                (D) TOPOLOGY: linear (ii) MOLECULE TYPE: DNA (synthetic)

(xi) SEQUENCE DESCRIPTION: SEQ ID NO: 37:

RTARTCNCKR TCDATNGT                                              18

(2) INFORMATION FOR SEQ ID NO: 38:

(i) SEQUENCE CHARACTERISTICS:
                (A) LENGTH: 18 base pairs
                (B) TYPE: nucleic acid
                (C) STRANDEDNESS: single
                (D) TOPOLOGY: linear (ii) MOLECULE TYPE: DNA (synthetic)

(xi) SEQUENCE DESCRIPTION: SEQ ID NO: 38:

RTGNGTNCCD ATRTCRTG                                              18

(2) INFORMATION FOR SEQ ID NO: 39:

(i) SEQUENCE CHARACTERISTICS:
                (A) LENGTH: 18 base pairs
                (B) TYPE: nucleic acid
                (C) STRANDEDNESS: single
                (D) TOPOLOGY: linear (ii) MOLECULE TYPE: DNA (synthetic)

(xi) SEQUENCE DESCRIPTION: SEQ ID NO: 39:

NARRTGRTGD ATNACRTG                                              18

(2) INFORMATION FOR SEQ ID NO: 40:

(i) SEQUENCE CHARACTERISTICS:
                (A) LENGTH: 21 base pairs
                (B) TYPE: nucleic acid
                (C) STRANDEDNESS: single
                (D) TOPOLOGY: linear (ii) MOLECULE TYPE: DNA (synthetic)

(xi) SEQUENCE DESCRIPTION: SEQ ID NO: 40:

DATYTGNGGR AANARRTGRT G                                             21

(2) INFORMATION FOR SEQ ID NO: 41:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (synthetic)

(xi) SEQUENCE DESCRIPTION: SEQ ID NO: 41:

GGDATYTGNG GRAANARRTG                                               20

(2) INFORMATION FOR SEQ ID NO: 42:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: DNA (synthetic)

(xi) SEQUENCE DESCRIPTION: SEQ ID NO: 42:

RTARTGNGGD ATYTGNGGRA ANA                                           23

(2) INFORMATION FOR SEQ ID NO: 43:

(i) SEQUENCE CHARACTERISTICS:
            (A) LENGTH: 7 amino acids
            (B) TYPE: amino acid
            (D) TOPOLOGY: linear (ii) MOLECULE TYPE: peptide (xi) SEQUENCE DESCRIPTION: SEQ ID NO: 43:

Asp Ile Arg Ala Ala Ile Pro
1               5

(2) INFORMATION FOR SEQ ID NO: 44:

(i) SEQUENCE CHARACTERISTICS:
            (A) LENGTH: 6 amino acids
            (B) TYPE: amino acid
            (D) TOPOLOGY: linear (ii) MOLECULE TYPE: peptide (xi) SEQUENCE DESCRIPTION: SEQ ID NO: 44:

Ala Ile Pro Lys His Cys
1               5

(2) INFORMATION FOR SEQ ID NO: 45:

(i) SEQUENCE CHARACTERISTICS:
            (A) LENGTH: 6 amino acids
            (B) TYPE: amino acid
            (D) TOPOLOGY: linear (ii) MOLECULE TYPE: peptide (xi) SEQUENCE DESCRIPTION: SEQ ID NO: 45:

Lys His Cys Trp Val Lys
1               5

(2) INFORMATION FOR SEQ ID NO: 46:

(i) SEQUENCE CHARACTERISTICS:
           (A) LENGTH: 8 amino acids
           (B) TYPE: amino acid
           (D) TOPOLOGY: linear (ii) MOLECULE TYPE: peptide (xi) SEQUENCE DESCRIPTION: SEQ ID NO: 46:

Trp Phe Leu Trp Pro Leu Tyr Trp
1               5

(2) INFORMATION FOR SEQ ID NO: 47:

(i) SEQUENCE CHARACTERISTICS:
           (A) LENGTH: 5 amino acids
           (B) TYPE: amino acid
           (D) TOPOLOGY: linear (ii) MOLECULE TYPE: peptide (xi) SEQUENCE DESCRIPTION: SEQ ID NO: 47:

Trp Phe Leu Trp Pro
1               5

(2) INFORMATION FOR SEQ ID NO: 48:

(i) SEQUENCE CHARACTERISTICS:
           (A) LENGTH: 5 amino acids
           (B) TYPE: amino acid
           (D) TOPOLOGY: linear (ii) MOLECULE TYPE: peptide (xi) SEQUENCE DESCRIPTION: SEQ ID NO: 48:

Trp Pro Leu Tyr Trp
1               5

(2) INFORMATION FOR SEQ ID NO: 49:

(i) SEQUENCE CHARACTERISTICS:
           (A) LENGTH: 6 amino acids
           (B) TYPE: amino acid
           (D) TOPOLOGY: linear (ii) MOLECULE TYPE: peptide (xi) SEQUENCE DESCRIPTION: SEQ ID NO: 49:

Trp Val Ala Gln Gly Thr
1               5

(2) INFORMATION FOR SEQ ID NO: 50:

(i) SEQUENCE CHARACTERISTICS:
           (A) LENGTH: 6 amino acids
           (B) TYPE: amino acid
           (D) TOPOLOGY: linear (ii) MOLECULE TYPE: peptide (xi) SEQUENCE DESCRIPTION: SEQ ID NO: 50:

Trp Val Ala Gln Gly Thr
1               5

(2) INFORMATION FOR SEQ ID NO: 51:

(i) SEQUENCE CHARACTERISTICS:
    (A) LENGTH: 6 amino acids
    (B) TYPE: amino acid
    (D) TOPOLOGY: linear (ii) MOLECULE TYPE: peptide (xi) SEQUENCE DESCRIPTION: SEQ ID NO: 51:

Val Leu Gly His Asp Cys
1               5

(2) INFORMATION FOR SEQ ID NO: 52:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (xi) SEQUENCE DESCRIPTION: SEQ ID NO: 52:

Gly His Asp Cys Gly His
1               5

(2) INFORMATION FOR SEQ ID NO: 53:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (xi) SEQUENCE DESCRIPTION: SEQ ID NO: 53:

Cys Gly His Gly Ser Phe
1               5

(2) INFORMATION FOR SEQ ID NO: 54:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (xi) SEQUENCE DESCRIPTION: SEQ ID NO: 54:

Pro Tyr His Gly Trp
1               5

(2) INFORMATION FOR SEQ ID NO: 55:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (xi) SEQUENCE DESCRIPTION: SEQ ID NO: 55:

His Gly Trp Arg Ile Ser His
1               5

(2) INFORMATION FOR SEQ ID NO: 56:

(i) SEQUENCE CHARACTERISTICS:
        (A) LENGTH: 9 amino acids
        (B) TYPE: amino acid
        (D) TOPOLOGY: linear

```
        (ii) MOLECULE TYPE: peptide (xi) SEQUENCE DESCRIPTION: SEQ ID NO: 56:

Trp Arg Ile Ser His Arg Thr His His
1               5

(2) INFORMATION FOR SEQ ID NO: 57:

(i) SEQUENCE CHARACTERISTICS:
            (A) LENGTH: 5 amino acids
            (B) TYPE: amino acid
            (D) TOPOLOGY: linear (ii) MOLECULE TYPE: peptide (xi) SEQUENCE DESCRIPTION: SEQ ID NO: 57:

Trp Arg Ile Ser His
1               5

(2) INFORMATION FOR SEQ ID NO: 58:

(i) SEQUENCE CHARACTERISTICS:
            (A) LENGTH: 5 amino acids
            (B) TYPE: amino acid
            (D) TOPOLOGY: linear (ii) MOLECULE TYPE: peptide (xi) SEQUENCE DESCRIPTION: SEQ ID NO: 58:

His Arg Thr His His
1               5

(2) INFORMATION FOR SEQ ID NO: 59:

(i) SEQUENCE CHARACTERISTICS:
            (A) LENGTH: 6 amino acids
            (B) TYPE: amino acid
            (D) TOPOLOGY: linear (ii) MOLECULE TYPE: peptide (xi) SEQUENCE DESCRIPTION: SEQ ID NO: 59:

Glu Asn Asp Glu Ser Trp
1               5

(2) INFORMATION FOR SEQ ID NO: 60:

(i) SEQUENCE CHARACTERISTICS:
            (A) LENGTH: 6 amino acids
            (B) TYPE: amino acid
            (D) TOPOLOGY: linear (ii) MOLECULE TYPE: peptide (xi) SEQUENCE DESCRIPTION: SEQ ID NO: 60:

Asp Glu Ser Trp Val Pro
1               5

(2) INFORMATION FOR SEQ ID NO: 61:

(i) SEQUENCE CHARACTERISTICS:
            (A) LENGTH: 6 amino acids
            (B) TYPE: amino acid
            (D) TOPOLOGY: linear (ii) MOLECULE TYPE: peptide (xi) SEQUENCE DESCRIPTION: SEQ ID NO: 61:
```

```
Trp Leu Asp Ala Val Thr
 1               5
```

(2) INFORMATION FOR SEQ ID NO: 62:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (xi) SEQUENCE DESCRIPTION: SEQ ID NO: 62:

```
Thr Tyr Leu His His
 1               5
```

(2) INFORMATION FOR SEQ ID NO: 63:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (xi) SEQUENCE DESCRIPTION: SEQ ID NO: 63:

```
Trp Ser Tyr Leu Arg Gly Gly Leu
 1               5
```

(2) INFORMATION FOR SEQ ID NO: 64:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (xi) SEQUENCE DESCRIPTION: SEQ ID NO: 64:

```
Leu Thr Thr Ile Asp Arg Asp
 1               5
```

(2) INFORMATION FOR SEQ ID NO: 65:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (xi) SEQUENCE DESCRIPTION: SEQ ID NO: 65:

```
Thr Ile Asp Arg Asp Tyr
 1               5
```

(2) INFORMATION FOR SEQ ID NO: 66:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (xi) SEQUENCE DESCRIPTION: SEQ ID NO: 66:

```
His Asp Ile Gly Thr His
 1               5
```

(2) INFORMATION FOR SEQ ID NO: 67:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (xi) SEQUENCE DESCRIPTION: SEQ ID NO: 67:

```
His Val Ile His His Leu
1               5
```

(2) INFORMATION FOR SEQ ID NO: 68:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (xi) SEQUENCE DESCRIPTION: SEQ ID NO: 68:

```
His His Leu Phe Pro Gln Ile
1               5
```

(2) INFORMATION FOR SEQ ID NO: 69:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (xi) SEQUENCE DESCRIPTION: SEQ ID NO: 69:

```
His Leu Phe Pro Gln Ile Pro
1               5
```

(2) INFORMATION FOR SEQ ID NO: 70:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (xi) SEQUENCE DESCRIPTION: SEQ ID NO: 70:

```
Leu Phe Pro Gln Ile Pro His Tyr
1               5
```

(2) INFORMATION FOR SEQ ID NO: 71:

(i) SEQUENCE CHARACTERISTICS:
        (A) LENGTH: 1670 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 46..1302

(xi) SEQUENCE DESCRIPTION: SEQ ID NO: 71:

```
CAAACTCTCT CGGGGGGTCG CTTCTTCTGC ATTTTCTGCT TCCCA ATG GCT TCC       54
                                                Met Ala Ser
```

```
                    1
AGA ATT GCT GAT TCT CTC TTC GCC TTC ACG GGC CCA CAG CAA TGT CTT        102
Arg Ile Ala Asp Ser Leu Phe Ala Phe Thr Gly Pro Gln Gln Cys Leu
  5              10                  15

CCT AGG GTT CCT AAG CTT GCT GCT TCT TCT GCT CGT GTT TCT CCT GGT        150
Pro Arg Val Pro Lys Leu Ala Ala Ser Ser Ala Arg Val Ser Pro Gly
 20              25                  30                  35

GTA TAT GCT GTG AAG CCG ATT GAT CTT CTG TTA AAA GGA CGA ACT CAT        198
Val Tyr Ala Val Lys Pro Ile Asp Leu Leu Leu Lys Gly Arg Thr His
             40                  45                  50

CGA AGT AGA AGA TGT GTA GCT CCT GTG AAA AGG AGA ATT GGA TGT ATC        246
Arg Ser Arg Arg Cys Val Ala Pro Val Lys Arg Arg Ile Gly Cys Ile
             55                  60                  65

AAA GCG GTG GCT GCT CCA GTT GCA CCG CCT TCA GCT GAC AGT GCA GAA        294
Lys Ala Val Ala Ala Pro Val Ala Pro Pro Ser Ala Asp Ser Ala Glu
             70                  75                  80

GAC AGG GAA CAG TTA GCA GAA AGC TAT GGA TTC AGA CAA ATT GGA GAA        342
Asp Arg Glu Gln Leu Ala Glu Ser Tyr Gly Phe Arg Gln Ile Gly Glu
     85                  90                  95

GAT CTT CCT GAG AAT GTC ACC TTA AAA GAT ATC ATG GAT ACA CTT CCC        390
Asp Leu Pro Glu Asn Val Thr Leu Lys Asp Ile Met Asp Thr Leu Pro
100                 105                 110                 115

AAA GAG GTG TTT GAG ATT GAT GAT CTG AAA GCT TTG AAG TCT GTG TTG        438
Lys Glu Val Phe Glu Ile Asp Asp Leu Lys Ala Leu Lys Ser Val Leu
                120                 125                 130

ATA TCT GTG ACT TCA TAC ACT TTG GGG CTC TTC ATG ATT GCA AAA TCG        486
Ile Ser Val Thr Ser Tyr Thr Leu Gly Leu Phe Met Ile Ala Lys Ser
                135                 140                 145

CCG TGG TAT CTG CTA CCG TTG GCT TGG GCA TGG ACA GGA ACT GCA ATT        534
Pro Trp Tyr Leu Leu Pro Leu Ala Trp Ala Trp Thr Gly Thr Ala Ile
        150                 155                 160

ACC GGG TTC TTT GTG ATA GGT CAT GAT TGT GCA CAT AAG TCA TTT TCA        582
Thr Gly Phe Phe Val Ile Gly His Asp Cys Ala His Lys Ser Phe Ser
165                 170                 175

AAG AAC AAA TTG GTG GAA GAC ATT GTG GGT ACT CTC GCC TTC CTA CCA        630
Lys Asn Lys Leu Val Glu Asp Ile Val Gly Thr Leu Ala Phe Leu Pro
180                 185                 190                 195

CTT GTC TAC CCA TAT GAG CCA TGG CGG TTT AAG CAC GAC CGC CAT CAC        678
Leu Val Tyr Pro Tyr Glu Pro Trp Arg Phe Lys His Asp Arg His His
                200                 205                 210

GCC AAA ACC AAC ATG TTA CTT CAT GAC ACA GCT TGG CAG CCA GTT CCG        726
Ala Lys Thr Asn Met Leu Leu His Asp Thr Ala Trp Gln Pro Val Pro
        215                 220                 225

CCA GAG GAG TTT GAG TCA TCA CCC GTG ATG AGA AAG GCA ATC ATT TTT        774
Pro Glu Glu Phe Glu Ser Ser Pro Val Met Arg Lys Ala Ile Ile Phe
        230                 235                 240

GGA TAT GGC CCA ATT AGA CCT TGG TTG TCC ATA GCT CAC TGG GTG AAC        822
Gly Tyr Gly Pro Ile Arg Pro Trp Leu Ser Ile Ala His Trp Val Asn
        245                 250                 255

TGG CAC TTC AAT CTG AAA AAG TTC AGA GCG AGC GAG GTG AAT AGG GTG        870
Trp His Phe Asn Leu Lys Lys Phe Arg Ala Ser Glu Val Asn Arg Val
260                 265                 270                 275

AAG ATA AGT TTG GCT TGT GTT TTC GCC TTC ATG GCC GTT GGG TGG CCA        918
Lys Ile Ser Leu Ala Cys Val Phe Ala Phe Met Ala Val Gly Trp Pro
                280                 285                 290

CTG ATC GTA TAC AAA GTT GGT ATA TTG GGA TGG GTA AAA TTC TGG TTA        966
Leu Ile Val Tyr Lys Val Gly Ile Leu Gly Trp Val Lys Phe Trp Leu
        295                 300                 305

ATG CCA TGG TTG GGC TAT CAC TTC TGG ATG AGC ACA TTC ACA ATG GTT       1014
Met Pro Trp Leu Gly Tyr His Phe Trp Met Ser Thr Phe Thr Met Val
```

```
Met Pro Trp Leu Gly Tyr His Phe Trp Met Ser Thr Phe Thr Met Val
        310                 315                 320

CAT CAT ACG GCT CCG CAT ATA CCT TTC AAG CCT GCG GAT GAG TGG AAC   1062
His His Thr Ala Pro His Ile Pro Phe Lys Pro Ala Asp Glu Trp Asn
    325                 330                 335

GCG GCT CAG GCC CAG CTG AAT GGA ACT GTT CAT TGT GAC TAC CCT AGT   1110
Ala Ala Gln Ala Gln Leu Asn Gly Thr Val His Cys Asp Tyr Pro Ser
340                 345                 350                 355

TGG ATT GAA ATT CTC TGC CAT GAT ATC AAC GTT CAC ATC CCG CAT CAT   1158
Trp Ile Glu Ile Leu Cys His Asp Ile Asn Val His Ile Pro His His
                360                 365                 370

ATT AGC CCA AGA ATA CCG AGC TAC AAT CTC CGT GCA GCT CAT GAG TCT   1206
Ile Ser Pro Arg Ile Pro Ser Tyr Asn Leu Arg Ala Ala His Glu Ser
            375                 380                 385

ATA CAA GAG AAC TGG GGA AAG TAT ACA AAC TTG GCT ACA TGG AAC TGG   1254
Ile Gln Glu Asn Trp Gly Lys Tyr Thr Asn Leu Ala Thr Trp Asn Trp
        390                 395                 400

CGA TTG ATG AAG ACG ATA ATG ACT GTG TGT CAT GTC TAT GAC AAA TAG   1302
Arg Leu Met Lys Thr Ile Met Thr Val Cys His Val Tyr Asp Lys
    405                 410                 415

GAGAACTACA TTCCTTTTGA CCGGTTAGCC CCTGAAGAAT CTCAGCCAAT AACCTTCCTC   1362

AAGAAATCAA TGCCTAACTA CACAGCCTGA TTCGCCATGG TCTCAAACTA GTCTTTTGAA   1427

ATCTCAATAT CTTTTTGCAGT CGCCGATGT TATATGTAAG CTTTCCAAGC GATGAGCTTC   1487

TCTAACACTT CACCAACGCTT TATACTGTT ATCTTCTTTC CAATCTTATC AGAAGAGAGA   1547

AACTGGTCAA ATTATCTGAGC GATTGCAAT TCTTTTATCA GTTTCTTAGC TATAAGAAGA   1607

TTGAACAGTC TATATAGTTTG CAATGTACT GTAATGTGAT GAAAATTTAG TTGATGAGAA   1667

AAAAAAA                                                             1670

(2) INFORMATION FOR SEQ ID NO: 72:

(i) SEQUENCE CHARACTERISTICS:
        (A) LENGTH: 418 amino acids
        (B) TYPE: amino acid
        (D) TOPOLOGY: linear (ii) MOLECULE TYPE: protein (xi) SEQUENCE DESCRIPTION: SEQ ID NO: 72:

Met Ala Ser Arg Ile Ala Asp Ser Leu Phe Ala Phe Thr Gly Pro Gln
 1               5                  10                  15

Gln Cys Leu Pro Arg Val Pro Lys Leu Ala Ala Ser Ser Ala Arg Val
            20                  25                  30

Ser Pro Gly Val Tyr Ala Val Lys Pro Ile Asp Leu Leu Lys Gly
        35                  40                  45

Arg Thr His Arg Ser Arg Cys Val Ala Pro Val Lys Arg Ile
    50                  55                  60

Gly Cys Ile Lys Ala Val Ala Ala Pro Val Ala Pro Ser Ala Asp
65                  70                  75                  80

Ser Ala Glu Asp Arg Glu Gln Leu Ala Glu Ser Tyr Gly Phe Arg Gln
            85                  90                  95

Ile Gly Glu Asp Leu Pro Glu Asn Val Thr Leu Lys Asp Ile Met Asp
            100                 105                 110

Thr Leu Pro Lys Glu Val Phe Glu Ile Asp Asp Leu Lys Ala Leu Lys
        115                 120                 125

Ser Val Leu Ile Ser Val Thr Ser Tyr Thr Leu Gly Leu Phe Met Ile
    130                 135                 140
```

```
Ala Lys Ser Pro Trp Tyr Leu Leu Pro Leu Ala Trp Ala Trp Thr Gly
145                 150                 155                 160

Thr Ala Ile Thr Gly Phe Phe Val Ile Gly His Asp Cys Ala His Lys
                165                 170                 175

Ser Phe Ser Lys Asn Lys Leu Val Glu Asp Ile Val Gly Thr Leu Ala
                180                 185                 190

Phe Leu Pro Leu Val Tyr Pro Tyr Glu Pro Trp Arg Phe Lys His Asp
            195                 200                 205

Arg His His Ala Lys Thr Asn Met Leu Leu His Asp Thr Ala Trp Gln
        210                 215                 220

Pro Val Pro Pro Glu Glu Phe Glu Ser Ser Pro Val Met Arg Lys Ala
225                 230                 235                 240

Ile Ile Phe Gly Tyr Gly Pro Ile Arg Pro Trp Leu Ser Ile Ala His
                245                 250                 255

Trp Val Asn Trp His Phe Asn Leu Lys Lys Phe Arg Ala Ser Glu Val
                260                 265                 270

Asn Arg Val Lys Ile Ser Leu Ala Cys Val Phe Ala Phe Met Ala Val
        275                 280                 285

Gly Trp Pro Leu Ile Val Tyr Lys Val Gly Ile Leu Gly Trp Val Lys
        290                 295                 300

Phe Trp Leu Met Pro Trp Leu Gly Tyr His Phe Trp Met Ser Thr Phe
305                 310                 315                 320

Thr Met Val His His Thr Ala Pro His Ile Pro Phe Lys Pro Ala Asp
                325                 330                 335

Glu Trp Asn Ala Ala Gln Ala Gln Leu Asn Gly Thr Val His Cys Asp
                340                 345                 350

Tyr Pro Ser Trp Ile Glu Ile Leu Cys His Asp Ile Asn Val His Ile
            355                 360                 365

Pro His His Ile Ser Pro Arg Ile Pro Ser Tyr Asn Leu Arg Ala Ala
        370                 375                 380

His Glu Ser Ile Gln Glu Asn Trp Gly Lys Tyr Thr Asn Leu Ala Thr
385                 390                 395                 400

Trp Asn Trp Arg Leu Met Lys Thr Ile Met Thr Val Cys His Val Tyr
                405                 410                 415

Asp Lys
```